US012370232B2

(12) United States Patent
Mitchell et al.

(10) Patent No.: US 12,370,232 B2
(45) Date of Patent: Jul. 29, 2025

(54) USE OF POLYPHENOL CONTAINING SUGAR CANE EXTRACTS FOR PREVENTING, IMPROVING OR TREATING A SKIN CONDITION

(71) Applicant: Poly Gain Pte Ltd, Singapore (SG)

(72) Inventors: Shane Mitchell, Keysborough (AU); Barry Kitchen, Keysborough (AU); Gregor Macnab, Keysborough (AU); Julian Neoh, Keysborough (AU); Matthew Flavel, Keysborough (AU)

(73) Assignee: Poly Gain Pte Ltd, Singapore (SG)

(*) Notice: Subject to any disclaimer, the term of this patent is extended or adjusted under 35 U.S.C. 154(b) by 0 days.

(21) Appl. No.: 17/960,503

(22) Filed: Oct. 5, 2022

(65) Prior Publication Data

US 2023/0173012 A1 Jun. 8, 2023

Related U.S. Application Data

(62) Division of application No. 16/637,584, filed as application No. PCT/AU2018/050826 on Aug. 8, 2018, now abandoned.

(30) Foreign Application Priority Data

Aug. 9, 2017 (AU) .............................. 2017903170

(51) Int. Cl.
*A61K 36/899* (2006.01)
*A61K 8/9794* (2017.01)
*A61K 9/00* (2006.01)
*A61K 9/06* (2006.01)
*A61K 31/191* (2006.01)
*A61P 17/02* (2006.01)
*A61P 17/04* (2006.01)
*A61P 17/06* (2006.01)
*A61P 17/08* (2006.01)
*A61P 17/10* (2006.01)
*A61P 17/14* (2006.01)
*A61Q 7/00* (2006.01)
*A61Q 19/02* (2006.01)
*A61Q 19/08* (2006.01)

(52) U.S. Cl.
CPC .......... *A61K 36/899* (2013.01); *A61K 8/9794* (2017.08); *A61K 9/0014* (2013.01); *A61K 9/0019* (2013.01); *A61K 9/06* (2013.01); *A61K 31/191* (2013.01); *A61P 17/02* (2018.01); *A61P 17/04* (2018.01); *A61P 17/06* (2018.01); *A61P 17/08* (2018.01); *A61P 17/10* (2018.01); *A61P 17/14* (2018.01); *A61Q 7/00* (2013.01); *A61Q 19/02* (2013.01); *A61Q 19/08* (2013.01)

(58) Field of Classification Search
CPC ..... A61K 36/899; A61K 31/191; A61P 17/02; A61Q 19/08
See application file for complete search history.

(56) References Cited

U.S. PATENT DOCUMENTS

2013/0209592 A1    8/2013  Denstman
2014/0357583 A1*  12/2014  Ilag ....................... A23L 33/105
                                                               514/27

FOREIGN PATENT DOCUMENTS

| JP | 2002-161046 A | 6/2002 |
| JP | 2003-137803 A | 5/2003 |
| WO | 2012/106761 A1 | 8/2012 |
| WO | 2014/032100 A1 | 3/2014 |
| WO | 2005/117608 A1 | 12/2015 |

OTHER PUBLICATIONS

Bountiful Baskets Blog (http://blog.bountifulbaskets.org/2015/04/28/what-about-molasses/) Apr. 28, 2015 (Year: 2015).*
Door of Youth (https://doorofyouth.com/sugar-cane-the-secret-to-smooth-skin/) Mar. 6, 2014 (Year: 2014).*
U.S. Kadam et al., "Antioxidant activity in sugarcane juice and its protective role against radiation induced DNA damage", Science Direct, Food Chemistry 106: 1154-1160 (2008).
A. Ratz-Łyko et al., "Influence of Polyphenols on the Physiological Processes in the Skin", Phytotherapy Research, Phytother. Res. 29: 509-517 (2015).
Office Action for Indian Patent Application No. No/ 202017004201 (May 8, 2022).
International Search Report and Written Opinion of the International Searching Authority for International Patent Application No. PCT/AU2018/050826 mailed Sep. 11, 2018, 8 pages.
Chinese Office Action for Chinese Patent Application No. 201880065498.6 dated Jul. 2, 2021, 13 pages.
Mintel GNPD, "AM/PM Dynamic Renewal Cream", Record ID: 4912813, 4 pages, (Jun. 2017), [retrieved from internet on Aug. 21, 2018], Available at: http://www.gnpd.com/sinatra/home/.
Mintel GNPD, "Intensive Renewal Serum", Record ID: 4973195, 3 pages, (Jul. 2017), [retrieved from internet on Aug. 21, 2018], Available at: http://www.gnpd.com/sinatra/home.
Brand, J.C. et al., "An Outstanding Food Source of Vitamin", The Lancet, 2(8303): 873 (Oct. 1982).
Shang, R.F. et al., Synthesis and Biological Evaluation of New Pleuromutilin Derivatives as Antibacterial Agents, Molecules, 19(11): 19050-19065 (2014).

(Continued)

*Primary Examiner* — Terry A McKelvey
*Assistant Examiner* — Jacob A Boeckelman
(74) *Attorney, Agent, or Firm* — Merchant & Gould P.C.

(57) ABSTRACT

The present disclosure is in the field of the prevention, improvement or treatment of skin conditions, for example skin conditions associated with skin aging and/or skin pigmentation and/or wound healing and/or psoriasis and/or acne. The disclosure provides extracts derived from sugar cane comprising polyphenols for the prevention, improvement or treatment of skin conditions, including skin conditions associated with skin aging and/or skin pigmentation and/or wound healing and/or psoriasis and/or acne.

13 Claims, 31 Drawing Sheets

(56) References Cited

OTHER PUBLICATIONS

Taguri, T. et al., "Antimicrobial Activity of 10 Different Plant Polyphenols against Bacteria Causing Food-Borne Disease", Biol. Pharm. Bull., 27(12): 1965-1969 (2004).

Tan, A.C. et al., "Potential Antioxidant, Antiinflammatory, and Proapoptotic Anticancer Activities of Kakadu Plum and Illawarra Plum Polyphenolic Fractions", Nutrition and Cancer, 63(7): 1074-1084 (2011).

Ratz-Lyko, A. et al., "Influence of Polyphenols on the Physiological Process in the Skin", Phytotherapy Research, 29: 509-517 (2015). And Tumbull (https://plantbasedbride.com/blog/blackstrap-molasses) Feb. 2, 2016 (Year: 2016).

Bountiful Baskets Blog (https://blog.bountifulbaskes.org/2015/04/2//what-about-molasses/) Apr. 28, 2015 (Year: 2015).

(Effects of a mixture of fatty acids from sugar cane (*Saccarum officinarum* L.) wax oil in two models of inflammation: Zymosan-induced arthritis and mice tail test of psoriasis, Phytomedicine 14 (2007), 690-695) (Year: 2007).

Anna Ratz-Lyko et al., "Influence of Polyphenols on the Physioloical Processes in the Skin", Phytotherapy Research, Phytother. Res. 29: 509-517 (2015).

1st Office Action for Chinese Patent Application No. 201880065498.6 (Jul. 2, 2021).

2nd Office Action for Chinese Patent Application No. 201880065498.6 (Jun. 8, 2022).

\* cited by examiner

FIG. 12A
FIG. 12B
Before
After

FIG. 13A
FIG. 13B
Before
After

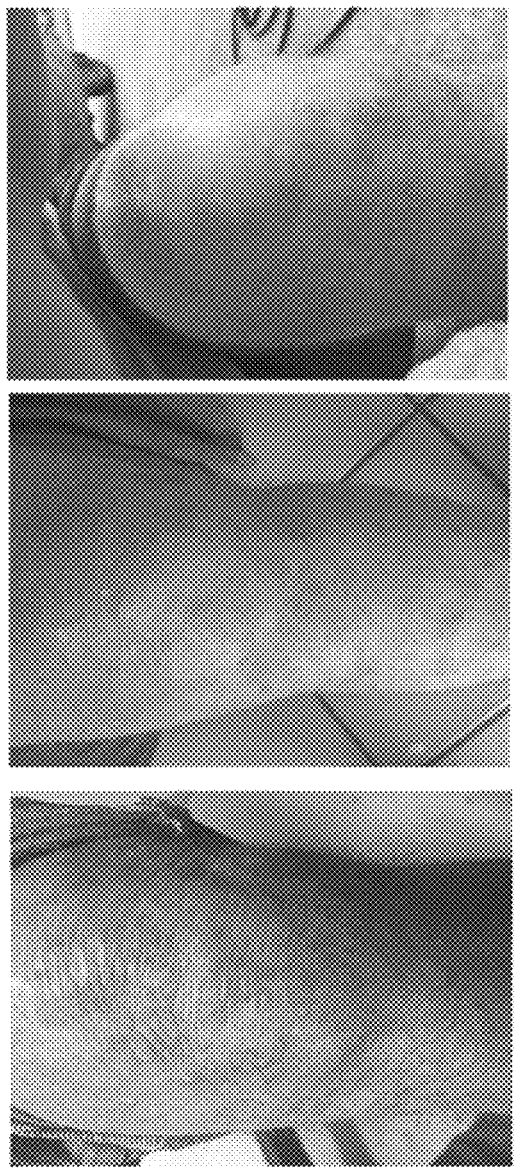

USE OF POLYPHENOL CONTAINING SUGAR CANE EXTRACTS FOR PREVENTING, IMPROVING OR TREATING A SKIN CONDITION

CROSS-REFERENCE TO RELATED APPLICATIONS

This application is a Divisional of U.S. patent application Ser. No. 16/637,584 filed on 7 Feb. 2020, which is a National Stage Application of PCT/AU2018/050826 filed on 8 Aug. 2018, which claims benefit of Australian Provisional Patent Application No 2017903170 filed on 9 Aug. 2017, the contents of which are incorporated herein by reference. To the extent appropriate, a claim of priority is made to each of the above disclosed applications.

TECHNICAL FIELD

The present disclosure is in the field of the prevention, improvement or treatment of skin conditions, for example skin conditions associated with skin aging and/or skin pigmentation and/or wound healing and/or psoriasis and/or acne. The disclosure provides extracts derived from sugar cane comprising polyphenols for the prevention, improvement or treatment of skin conditions, including skin conditions associated with skin aging and/or skin pigmentation and/or wound healing and/or psoriasis and/or acne.

BACKGROUND

The dermis layer of skin includes three crucial components: collagen, elastin, and glycosaminoglycans (GAGs). These components form the majority of the Extracellular Matrix (ECM). Proteoglycans are also present in the ECM.

Collagen is a structural protein found in connective tissues, such as skin, tendons, ligaments, cartilage, bones, teeth, heart valves, and the cornea. Collagen is composed of long fibres of protein and provides strength to the skin.

Elastin is a fibrous protein that is highly stretchy and resilient, providing elasticity to the skin. Elastin allows skin to resume its shape after stretching, contracting or pinching.

GAGs are polysaccharides. GAGs are water-binding substances and in combination with water, GAGs create a fluid that fills the space between the collagen and elastin fibers in the dermis, giving it turgidity (bounce). There are various GAGs in the dermis, the most common being: hyaluronic acid, chondroitin sulfate, keratin sulfate, dermatan sulfate, heparin sulfate, and heparin.

Deterioration of the physical appearance of skin (the skin's condition) typically appears as a result of aging processes. As skin ages, it becomes thinner and more easily damaged and its ability to heal itself is decreased. Among other things, skin aging is noted by a decrease in volume and elasticity.

As skin ages, quantitative and qualitative changes in collagen, elastin and GAGs in the skin occurs, leading to roughness, wrinkles and sagging of the skin. Melanin in the skin becomes unevenly distributed causing uneven tone, freckles and age spots. Sweat- and oil-secreting glands in the skin also decrease, leaving the skin dry and thin.

The effects of aging on the skin may also be promoted by habitual facial expressions, sun damage, smoking, poor hydration or nutrition, high stress levels, environmental pollution, alcohol or drug abuse, and various other factors.

Prevention, improvement and/or treatment methods for the deterioration of the physical appearance of skin may include sun protection, daily skin care routines, use of antioxidants, cessation of smoking and/or improved diet and the like. There are also cosmetic and/or therapeutic products and procedures for the physical appearance of skin available on the market. Examples of cosmetic products include products containing retinoids, vitamin C or alpha hydroxy acids. Examples of cosmetic procedures include Botox, chemical peels, dermabrasion, laser treatments and dermal fillers.

The cosmetic products and procedures available on the market have both some dangers and inadequacies for treating and/or ameliorating the aging and effects of aging of human skins. Additionally, the cosmetic procedures available are not suitable for self-administration and can add to increased costs associated with receiving treatment.

Other areas of cosmetic importance in relation to skin conditions include wound healing, psoriasis, acne and hair loss. Sufferers of psoriasis, acne and hair loss often suffer from embarrassment. Treatment of wounds can improve healing time, prevent infection and reduce scarring. Moreover, inflammation, which is associated with each of wound healing, psoriasis and acne causes skin redness, swelling and discomfort. Hence, reducing inflammation can therefore lead to improved wound healing, treatment of psoriasis and treatment of acne.

Accordingly, there is a need for improved formulations related to the treatment or management of skin aging and/or pigmentation and/or the treatment of wound healing and/or psoriasis and/or acne and/or hair loss.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In one aspect of the disclosure there is provided a method for preventing, improving or treating a skin condition in a subject, the method comprising topical or injection administration of a composition comprising from about 0.05 wt % to about 50 wt % of an extract derived from sugar cane to the subject, the extract comprising from about 10 catechin equivalent (CE) g/L to about 50 CE g/L of polyphenols or from about 100 CE mg/g to about 500 CE mg/g of polyphenols.

In another aspect of the disclosure there is provided use of an extract derived from sugar cane in the manufacture of a medicament for preventing, improving or treating a skin condition, the extract comprising from about 10 catechin equivalent (CE) g/L to about 50 CE g/L of polyphenols or from about 100 CE mg/g to about 500 CE mg/g of polyphenols, and wherein the medicament is formulated to be administered topically or by injection and comprises from about 0.05 wt % to about 50 wt % of the extract derived from sugar cane.

In another aspect of the disclosure there is provided a composition comprising from about 0.05 wt % to about 50 wt % of an extract derived from sugar cane for use in preventing, improving or treating a skin condition in a subject, the extract comprising from about 10 catechin equivalent (CE) g/L to about 50 CE g/L of polyphenols or from about 100 CE mg/g to about 500 CE mg/g of polyphenols, and wherein the use is topical or by injection.

In one embodiment, the composition comprises from about 0.05 wt % to about 10 wt % of the extract.

In one embodiment, the composition comprises from about 0.05 wt % to about 5 wt % of the extract.

In one embodiment, the skin condition is selected from the group consisting of atopic dermatitis, eczema, psoriasis, dry skin, oily skin, and pruritic skin.

In one embodiment, the skin condition is psoriasis.

In one embodiment, the skin condition is selected from the group consisting of wrinkles, fine lines, dark spots, age spots, mottled pigmentation, skin pigmentation, melasma, darkened skin, skin elasticity, dark circles under the eyes and changes associated with skin aging.

In one embodiment, the skin condition is selected from the group consisting of wrinkles, fine lines, skin elasticity, and changes associated with skin aging.

In one embodiment, the skin condition is selected from the group consisting of dark spots, age spots, mottled pigmentation, skin pigmentation, melasma, darkened skin, dark circles under the eyes and changes associated with skin aging.

In one embodiment, the skin condition is acne.

In one embodiment, the skin condition is wound healing.

In one embodiment, the skin condition is hair loss.

In one embodiment, the prevention, improvement or treatment of the skin condition provides skin moisturisation, skin exfoliation, skin lightening or colour reduction, skin pigmentation reduction, skin redness reduction, skin flushing reduction, inflammation reduction, fine line reduction, wrinkle reduction, wrinkle depth reduction, skin dryness reduction, skin roughness reduction, enhanced skin radiance, enhanced skin tone, enhanced skin clarity, enhanced skin firmness, enhanced skin tightness, enhanced skin elasticity, and/or enhanced overall skin appearance.

In one embodiment, the prevention, improvement or treatment of the skin condition provides skin moisturisation, skin exfoliation, skin redness reduction, skin flushing reduction, skin dryness reduction, enhanced skin radiance, enhanced skin tone, enhanced skin clarity, enhanced skin firmness, enhanced skin tightness, enhanced skin elasticity, and/or enhanced overall skin appearance.

In one embodiment, the prevention, improvement or treatment of the skin condition provides inflammation reduction.

In one embodiment, the prevention, improvement or treatment of the skin condition provides fine line reduction, wrinkle reduction, wrinkle depth reduction, enhanced skin elasticity, and/or skin roughness reduction.

In one embodiment, the prevention, improvement or treatment of the skin condition provides skin lightening or colour reduction and/or skin pigmentation reduction.

In one embodiment, the improvement or treatment of wound healing provides decreased formation of scar tissue, improved healing time, improved appearance of the healed skin, protection of the healing skin tissue from oxidative damage, and/or prevention or treatment of the wound from infection.

In another embodiment, the administration is topical.

In another embodiment, the administration is by injection.

In another embodiment, the composition is administered twice daily.

In another embodiment, the composition is administered once daily.

In one embodiment, the skin is on the face, neck, hands and/or back.

In one embodiment, the skin is on the face.

In one embodiment, the composition is in the form of a cream, serum or gel.

In one embodiment, the composition comprises the extract comprises from about 15 CE g/L to about 40 CE g/L of polyphenols or about 150 CE mg/g to about 400 CE mg/g of polyphenols.

In one embodiment, the extract comprises from about 20 CE g/L to about 30 CE g/L of polyphenols or from about 200 CE mg/g to about 300 CE mg/g of polyphenols.

In one embodiment, the extract is derived from a sugar cane derived product selected from the group consisting of molasses, massecuite, bagasse, first expressed juice, mill mud, clarified sugar juice, clarified syrup, treacle, golden syrup, field trash, cane strippings, dunder and combinations thereof.

In one embodiment, the sugar cane derived product is molasses.

In one embodiment, the composition comprises lactic acid and/or glycolic acid.

Any embodiment herein shall be taken to apply mutatis mutandis to any other embodiment unless specifically stated otherwise.

The present disclosure is not to be limited in scope by the specific embodiments described herein, which are intended for the purpose of exemplification only. Functionally-equivalent products, compositions and methods are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

BRIEF DESCRIPTION OF DRAWINGS

Whilst it will be appreciated that a variety of embodiments of the disclosure may be utilised, in the following, we describe a number of examples of the disclosure with reference to the following drawings:

FIGS. 12A and 12B exhibit a 58 year old subject over the 12 week trial. (FIG. 12A) It exhibits the subject's face before the 12 week trial. (FIG. 12B) After the 12 week trial the subject measured a 49% wrinkle reduction and a 65% reduction in skin roughness.

FIGS. 13A and 13B exhibit a 58 year old subject over the 12 week trial. (FIG. 13A) It exhibits the subject's face before the 12 week trial. (FIG. 13B) After the 12 week trial the subject measured a 37% wrinkle reduction.

FIGS. 14A, 14B, 14C and 14D exhibit a subject suffering from psoriasis over the 6 week trial. (FIG. 14A) It exhibits the subject's knee before the 6 week trial. (FIG. 14B) It exhibits the subject's knee after 2 weeks of continuous use of a composition comprising an extract derived from sugar cane of the present disclosure. (FIG. 14C) It exhibits the subject's knee after 4 weeks of continuous use of a composition comprising an extract derived from sugar cane of the present disclosure. (FIG. 14D) It exhibits the subject's knee after 6 of weeks of continuous use of a composition comprising an extract derived from sugar cane of the present disclosure.

FIGS. 15A, 15B and 15C exhibit a subject suffering from psoriasis over the 3 month trial. (FIG. 15A) It exhibits the subject's knee before the 3 month trial. (FIG. 15B) It exhibits the subject's knee after 1 month of continuous use of a composition comprising an extract derived from sugar cane of the present disclosure. (FIG. 15C) It exhibits the subject's knee after 3 months of continuous use of a composition comprising an extract derived from sugar cane of the present disclosure.

DETAILED DESCRIPTION

General Techniques and Definitions

Figure 1:
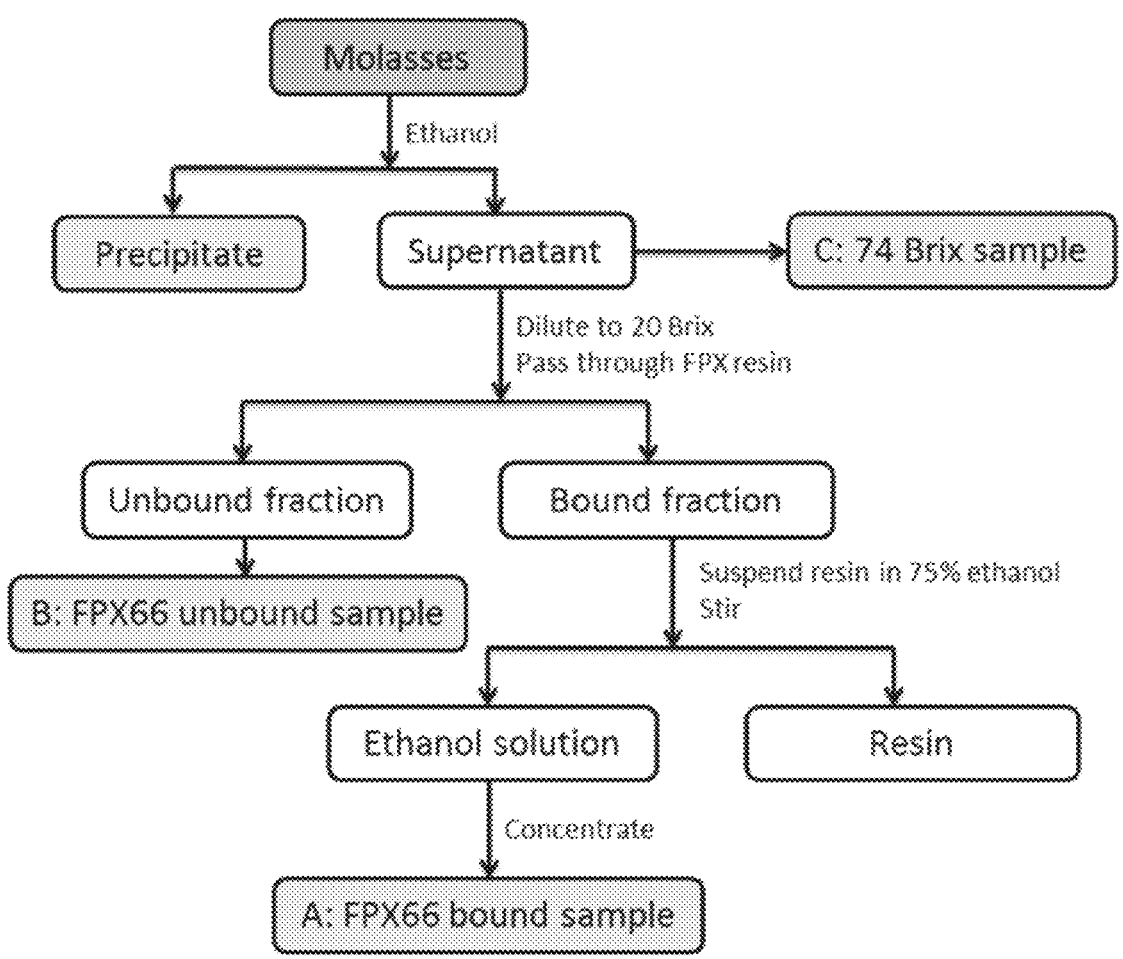
FIG. 1 exhibits an exemplary process for the preparation of extracts derived from molasses.

Unless specifically defined otherwise, all technical and scientific terms used herein shall be taken to have the same meaning as commonly understood by one of ordinary skill in the art (e.g., chemistry, biochemistry, cell culture, molecular biology, pharmacy, cosmetology, and dermatology). Further, unless otherwise required by context, singular terms shall include pluralities and plural terms shall include the singular. Thus, as used in this specification and the appended claims, the singular forms "a", "an" and "the" include plural referents unless the context clearly indicates otherwise. Thus, the term "an subject" means "one or more subjects" unless the context clearly indicates otherwise.

"Administering" as used herein is to be construed broadly and includes administering an extract or a composition comprising the extract as described herein to a subject as well as providing an extract or composition comprising the extract as described herein to a cell.

The phrase "an effective amount" as used herein, refers to an amount which is sufficient to elicit the biological or medical response of a tissue, system, animal or human that is being sought by the researcher, veterinarian, medical doctor or other clinician. Undesirable effects, e.g. side effects, are sometimes manifested along with the desired effect; hence, a practitioner balances the potential benefits against the potential risks in determining what an appropriate "effective amount" is. The exact amount required varies from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine experimentation. The effective amount in this context includes an amount required to treat or prevent or improve a skin condition. By "ameliorate" is included relieving of adverse symptoms, inducing a state of comfort or wellbeing or removing or reducing biochemical, physiological or clinical markers of the disease or the condition.

The terms "treating", "treat", "treatment", "improving", "improve" or "improvement", as used herein, include administering an effective amount of an extract of the present disclosure or a composition comprising the extract sufficient to reduce or delay the onset or progression of a specified condition, or to reduce or eliminate at least one symptom of the condition. As would be understood by those skilled in the art of treating or improving a skin condition, the term "treatment" includes that the skin condition is cured, however, it does not necessarily mean that the skin condition is completely cured.

The terms "preventing" or "prevent" as used herein, include administering an effective amount of an extract of the present disclosure or a composition comprising the extract sufficient to avoid the onset of a specified condition, or to avoid at least one symptom of the condition. As would be understood by those skilled in the art of preventing a skin condition, the term "preventing" includes that the skin condition is completely prevented, however, it does not necessarily mean that the skin condition is completely prevented.

"Subject" as used herein refers to an animal, such as mammal including a human who can benefit from the extracts derived from sugar cane, compositions containing the extracts and methods and uses described herein. There is no limitation on the type of animal that could benefit from the presently described extracts derived from sugar cane, compositions containing the extracts and methods and uses. A subject regardless of whether a human or non-human animal may be referred to as an individual, subject, animal, host or recipient as well as patient. of the present disclosure have applications in human medicine, human cosmetics, and veterinary medicine.

The term "about" as used herein refers to a range of +/−5% of the specified value.

The term "CE", or "catechin equivalent" as used herein is a measure of total polyphenolic content, expressed as mg catechin equivalents/g crude material or g catechin equivalents/L crude material.

The term "GAE", or "gallic acid equivalent" as used herein is a measure of total polyphenolic content, expressed as mg gallic acid equivalents/g extract derived from sugar cane or g gallic acid equivalents/L extract derived from sugar cane.

The term "free amino acids" as used herein refers to amino acids which are singular molecules and structurally not attached to peptide bonds which are attached to other amino acids.

The term "sugar cane derived product" as used herein refers to products of the sugar cane milling and refining processes including, but not limited to, sugar, molasses, massecuite, bagasse, first expressed juice, mill mud, clarified sugar cane juice, clarified syrup, treacle, golden syrup, field trash, cane strippings, leaves, growing tips, pulp and dunder and combinations thereof. Dunder is the residue produced when a product such as sugar or molasses is fermented to give, for example, ethanol. Sugar cane dunder is also referred to as biodunder, stillage or vinasse. As used herein, the terms "dunder", "bio-dunder", "stillage" and "vinasse" are equivalent and used interchangeably.

Throughout this specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 5, 5.5 and 6, unless where integers are required or implicit from context. This applies regardless of the breadth of the disclosed range. Where specific values are required, these will be indicated in the specification.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Extracts Derived from Sugar Cane to Prevent, Improve or Treat a Skin Condition

It has been previously demonstrated that sugar cane waste and sugar cane extracts provide various benefits to human beings and animals. For example, sugar cane waste has been used for feed for animals and for a source to the bio-fuel industry. It has also been reported that some sugar cane extracts containing phytochemicals may be used as a nutritional supplements to provide a boost of energy and that some sugar cane extracts containing phytochemicals have the ability to lower the glycaemic index (GI) of foods and beverages. Lowering the GI of foods and beverages has potential applications, such as in reducing the risk of, and regulating and/or managing, conditions such as obesity and diabetes.

Certain documents provide processes for producing sugar cane extracts and the use of such extracts in methods of lowering the available calorific value of foods and/or beverages, in treating or preventing diseases, and as a nutritional supplements, dietary supplements, food ingredients, food modifiers, sports nutrition products, food coatings and/or pharmaceutical products (e.g. WO/2014/032100, WO/2012/106761).

However, the use of extracts derived from sugar cane comprising a specific range of polyphenol content has not previously been described in the application of preventing, improving or treating a skin condition. The present inventors have surprisingly found that the polyphenol containing extracts derived from sugar cane of the present disclosure can be used to prevent, improve or treat various types of skin conditions.

The extracts derived from sugar cane of the present disclosure have been demonstrated to treat or to improve various types of skin conditions. The skin conditions include, for example, atopic dermatitis, acne, eczema, psoriasis, dry skin, oily skin, pruritic skin, wrinkles, fine lines, dark spots, age spots, mottled pigmentation, skin pigmentation, melasma, darkened skin, redness, flushing, inflammation, skin elasticity, dark circles under the eyes and changes associated with skin aging, hair loss and wound healing.

The effects of the treatment or improvement include skin lightening, fine line reduction, wrinkle reduction, wrinkle depth reduction, improvement of skin radiance, tone and clarity, skin inflammation reduction, improvement of skin firmness, tightness, and elasticity, skin moisturisation, improvement of skin's overall appearance, skin colour reduction, skin redness reduction, skin flushing reduction, skin dryness reduction and skin roughness reduction. The effects of the treatment or improvement also include reduced itchiness and flakiness. When the skin condition is wound healing, the effects of the treatment or improvement include reduced inflammation and therefore decreased formation of scar tissue, improved healing time and appearance of the healed skin, protection of the healing skin from oxidative damage and antibacterial properties which aid in the prevention of the wound from infection or treatment of the infection, which can delay the healing process.

Exemplary Processes for Producing Extracts Derived from Sugar Cane

A suitable process for producing the extract derived from sugar cane may be determined by one of ordinary skill in the art. Exemplary processes are provided below.

Feedstock for the Extraction Process

After being mechanically harvested, sugar cane is transported to a mill and crushed between serrated rollers. The crushed sugar cane is then pressed to extract raw sugar juice and leaves fibrous material known as bagasse (typically used as fuel). The raw juice is then heated to its boiling point to extract any impurities, then lime and bleaching agents are added and mill mud is removed. The raw juice is further heated under vacuum to concentrate and increase the Brix value. The concentrated syrup is seeded to produce bulk sugar crystals and a thick syrup known as molasses. The two are separated by a centrifuge and typically the molasses waste stream is collected for use as a low-grade animal feedstock.

The extracts produced according to the processes of the disclosure can be derived from any sugar cane derived product, including those produced during the sugar cane milling process, the sugar cane refining process and other processes using sugar cane products.

Accordingly, the term "sugar cane derived product" as used herein refers to products of the sugar cane milling and refining processes including, but not limited to, molasses, massecuite, bagasse, first expressed juice, mill mud, clarified sugar juice, clarified syrup, treacle, golden syrup, field trash, cane strippings, growing tips, pulp, dunder and combinations thereof. In one embodiment, the sugar can derived product is molasses or dunder. In another embodiment, the sugar can derived product is molasses. In another embodiment, the sugar can derived product is dunder. In another embodiment, the sugar cane derived product is a combination of molasses and dunder. In another embodiment, the sugar cane derived product is massecuite. In another embodiment, the sugar cane derived product is bagasse. In another embodiment, the sugar cane derived product is first expressed juice. In another embodiment, the sugar cane derived product is mill mud. In another embodiment, the sugar cane derived product is clarified sugar cane juice. In another embodiment, the sugar cane derived product is clarified syrup. In another embodiment, the sugar cane derived product is treacle. In another embodiment, the sugar cane derived product is golden syrup. In another embodiment, the sugar cane derived product is field trash. In another embodiment, the sugar cane derived product is cane strippings. In another embodiment, the sugar cane derived product is leaves. In another embodiment, the sugar cane derived product is growing tips. In another embodiment, the sugar cane derived product is pulp.

Sugar cane derived products generally comprise complex mixtures of substances including, but not limited to, polyphenols, phytosterols, monosaccharides, disaccharides, oligosaccharides, polysaccharides, organic acids, amino acids, peptides, proteins, vitamins, and minerals.

As would be understood by one of ordinary skill in the art, polyphenols are compounds characterized by the presence of multiple phenol structural units. Polyphenols may be classified into sub-groups by their chemical structure. Examples of sub-groups of polyphenols include, but are not limited to, flavonoids (including flavones, flavanols, flavonols), hydroxybenzoic acids, hydroxycinamic acids, catechins, proanthocyanidins, anthocyanidins, stilbenes, lignans, and phenolic acids. The polyphenols of sugar cane derived products also include conjugates such as, for example, glycosides, glucosides, galactosides, galacturonides, ethers, esters, arabinosides, sulphates, phosphates, aldopentoses (xylose, arabinose) and aldohexoses.

Exemplary Processes Involving an Extraction Step

One exemplary process with molasses as the sugar cane derived product is depicted in FIG. 1.

In one process for producing extracts of the disclosure, the sugar cane derived product is used as a feedstock and mixed with a suitable solvent such as ethanol to form an extraction mixture.

One of ordinary skill in the art will understand that in order to facilitate mixing of the sugar cane derived product with a suitable solvent such as ethanol, the sugar cane derived product may need to be mixed with a liquid, for example but not limited to water, and/or heated in order to achieve a desired viscosity. In one embodiment of the disclosure in which the sugar cane derived product is molasses, for example, the molasses may be mixed with a liquid, for example, water to achieve a desired viscosity. The sugar cane derived product, either mixed with a liquid or not, may be heated to decrease viscosity.

For sugar cane derived products comprising solid material such as bagasse, field trash and cane shippings, it is desirable that the product is first blended or homogenised with a liquid, for example but not limited to water, prior to mixing with ethanol to form the extraction mixture. The amount of a liquid with which the sugar cane derived product is blended or homogenised can be readily determined by one of ordinary skill in the art in order to achieve a sugar cane derived product having a suitable viscosity for mixing with ethanol to form an extraction mixture.

In one embodiment, the sugar cane derived product will have a viscosity less than or equal to about 100 centipoise. In another embodiment, the sugar cane derived product will have a viscosity of between about 50 to about 100 centipoise. In another embodiment, the sugar cane derived product will have a viscosity of between about 50 to about 80 centipoise.

The high viscosity of molasses is as a result of the high total solids (particularly soluble carbohydrates) and this is typically measured by determination of Brix degrees. In one embodiment, the sugar cane derived product may have about 10° to about 80° Brix. In another embodiment, the sugar cane derived product may have about 20° to about 70° Brix. In another embodiment, the sugar cane derived product may have about 20° to about 50° Brix. In another embodiment, the sugar cane derived product may have about 30° to about 60° Brix. In another embodiment, the sugar cane derived product may have about 40° to about 50° Brix.

Addition of Ethanol to the Sugar Cane Derived Product

To extract compounds such as polyphenols, the sugar cane derived product may be mixed with ethanol to form an extraction mixture. In one embodiment, the extraction mixture comprises at least about 50% v/v ethanol. In another embodiment, the extraction mixture comprises at least about 55%, 60%, 65%, 70%, 71%, 72%, 73%, 74%, 75%, 76%, 77%, 78%, 79%, 80%, 81%, 82%, 83%, 84% or 85% v/v ethanol.

The optimal concentration of ethanol in the extraction mixture for removing colour in the supernatant while minimising reduction in polyphenols is about 70% to about 85% v/v. In one embodiment, the extraction mixture comprises about 65% to about 75% v/v ethanol. In one embodiment, the extraction mixture comprises about 70% to about 80% v/v ethanol. In one embodiment, the extraction mixture comprises about 70% to about 75% v/v ethanol. In one embodiment, the extraction mixture comprises about 75% to about 80% v/v ethanol. In one embodiment, the extraction mixture comprises about 80% to about 85% v/v ethanol. In one embodiment, the extraction mixture comprises about 80% to about 83% v/v ethanol. In one embodiment, the extraction mixture comprises about 65% v/v ethanol. In another embodiment, the extraction mixture comprises about 70% v/v ethanol. In another embodiment, the extraction mixture comprises about 75% v/v ethanol. In another embodiment, the extraction mixture comprises about 80% v/v ethanol. In another embodiment, the extraction mixture comprises about 83% v/v ethanol. In another embodiment, the extraction mixture comprises about 85% v/v ethanol.

In the process of the disclosure, it may be desirable that extremes of pH be avoided in the extraction mixture. Extreme pH can have a deleterious effect on the components of the extraction mixture. Accordingly, in one embodiment the extraction mixture has a pH of about pH 4 to about pH 7.5. In another embodiment, the extraction mixture has a pH of about pH 4 to about pH 6. In another embodiment, the extraction mixture has a pH of about pH 4 to about pH 5.

Removal of Precipitate and Ethanol

Following the formation of precipitate in the extraction mixture, the precipitate may be removed from the mixture by any suitable method known in the art. For example the precipitate may be removed by centrifugation and the supernatant may be obtained. Alternatively, the precipitate may be allowed to settle for a time sufficient to allow the supernatant to be obtained while leaving precipitate behind, such as, for example, by sedimentation under gravity. One of ordinary skill in the art will understand that other techniques such as filtration can be used alone or in combination with centrifugation or sedimentation in order to produce the extract derived from sugar cane.

Once the supernatant has been obtained the ethanol is removed using techniques known in the art. By way of non-limiting example, the ethanol may be removed from the supernatant by evaporation, such as by using a rotary evaporator with a heating bath at approximately 45° C. or higher. In some instances it may be desirable to further remove water from the supernatant to increase the Brix value of the supernatant. In one embodiment the process provides an extract having at least about 60° Bx (degrees Brix). In some instances the Bx value of the extract derived from sugar cane is at least about 65° Bx. In some instances the Bx value of the extract derived from sugar cane is at least about 70° Bx. In some instances the Bx value of the extract derived from sugar cane is about 60-65° Bx. In some instances the Bx value of the extract derived from sugar cane is about 65-70° Bx. In some instances the Bx value of the extract derived from sugar cane is about 64-65° Bx. In some instances the Bx value of the extract derived from sugar cane is about 70-75° Bx.

Fractionation of the Extract Derived from Sugar Cane

In one embodiment of the process of the disclosure, the supernatant comprising ethanol, or the extract derived from sugar cane from which ethanol has been removed may be used without further processing. Optionally the supernatant comprising ethanol, or the extract derived from sugar cane from which ethanol has been removed may be subjected to purification or fractionation.

A purification step may remove impurities, such as pigments that contribute to the colour of the extract derived from sugar cane. By way of non-limiting example, the supernatant or the extract derived from sugar cane may be subject to a purification step which includes, one or more or of, membrane filtration, size exclusion chromatography, ion exchange chromatography, and/or hydrophobic interaction chromatography. In one embodiment, the supernatant or extract may be subjected to hydrophobic interaction chromatography.

There are several techniques known in the art for separating compounds based on size. For example, it is known in the art that components of a supernatant or extract falling within a specific molecular weight range may be separated by size exclusion processing methods such as gel permeation chromatography or ultrafiltration.

Separation of components in the supernatant and/or the extract derived from sugar cane may also be achieved using chromatographic techniques or combinations of techniques. In one embodiment, chromatographic techniques include, but are not limited to, ion exchange chromatography, hydrophobic interaction chromatography, liquid chromatography-mass spectrometry (LCMS) and/or HPLC. Appropriate stationary and mobile phases of any chromatographic technique used will be readily determined by one of ordinary skill in the art. Appropriate elution techniques will also be readily determined by one of ordinary skill in the art. Chromatographic techniques may utilise fractional elution by stepwise increase in pH or with suitable solvents.

In one embodiment, the supernatant and/or the extract derived from sugar cane is subjected to one or more chromatographic techniques. In one embodiment, the supernatant and/or the extract derived from sugar cane is subjected to hydrophobic interaction chromatography. In one embodiment, the supernatant and/or the extract derived from sugar cane is subjected to hydrophobic interaction chromatography with an XAD, sephadex LH-20 or FPX66 resin. In one embodiment, the supernatant and/or the extract derived from sugar cane is subjected to sephadex LH-20 resin. In one embodiment, the supernatant and/or the extract derived from sugar cane is subjected to XAD resin. In one embodiment, the supernatant and/or the extract derived from sugar cane is subjected to FPX66 resin.

The supernatant and/or the extract derived from sugar cane may also be processed by standard techniques such as, but not limited to, microfiltration, reverse osmosis, gel permeation, vacuum evaporation and freeze drying, spray drying and/or tunnel drying.

Exemplary Processes without an Extraction Step

Figure 2:
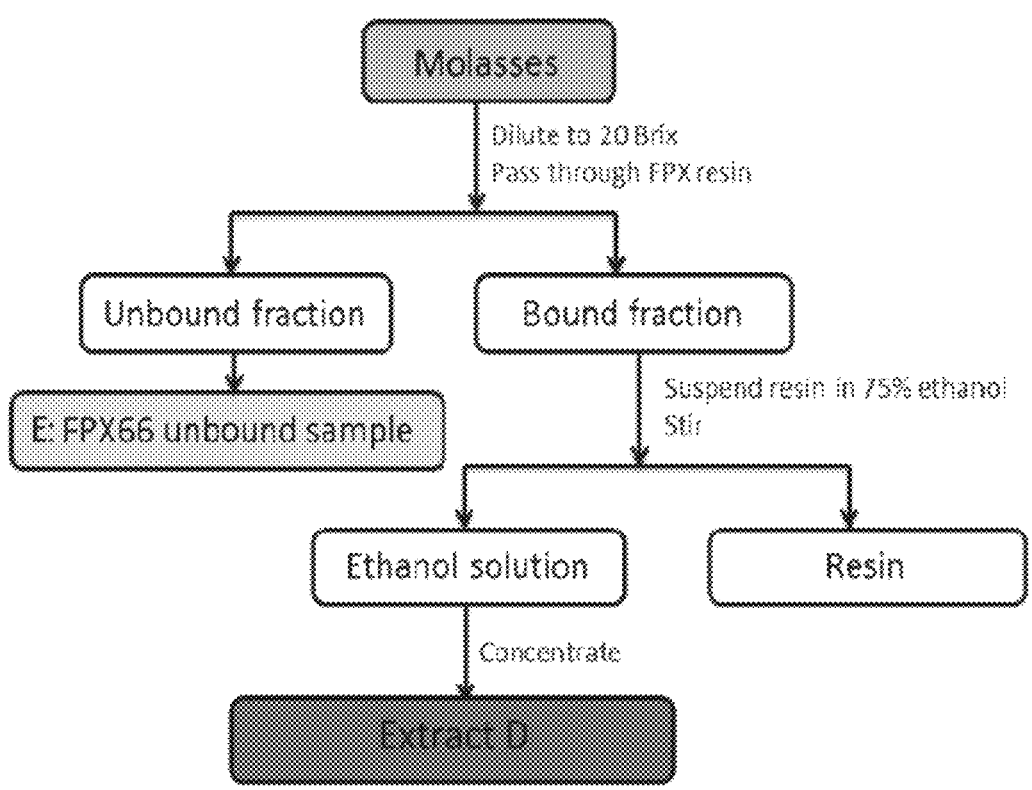
FIG. 2 exhibits another exemplary process for the preparation of extracts derived from molasses.

Another exemplary process with molasses as the sugar cane derived product is depicted in FIG. 2. In this process for producing extracts of the disclosure, the molasses and is not mixed with ethanol in a preliminary step. The extract derived from sugar cane may be obtained from a process without the addition of ethanol in the first step (FIG. 2).

To obtain the extract derived from sugar cane, molasses may first diluted in a liquid, for example but not limited to, water, to a desired Brix value. In one embodiment, the molasses is diluted to about 20° Bx with water. The components of the diluted solution may be subjected to one or more chromatographic techniques known in the art, for example by passing over a FPX66 ion exchange resin. A range of components from the molasses bind to the ion exchange resin beads and these components are collected later in the process as the bound fraction. The unbound fraction is eluted and may or may not be processed further. Once the unbound fraction has been removed from the system, ethanol may be used to elute the bound fraction. In one embodiment, 75% ethanol is used to elute the bound fraction. Following elution, the ethanol may be evaporated from the solution. Any method for removing the ethanol may be employed, including for example, heat exchange and evaporation. In one embodiment, ethanol is removed by evaporation.

Exemplary Processes with Multiple Filtration Steps

Figure 9:
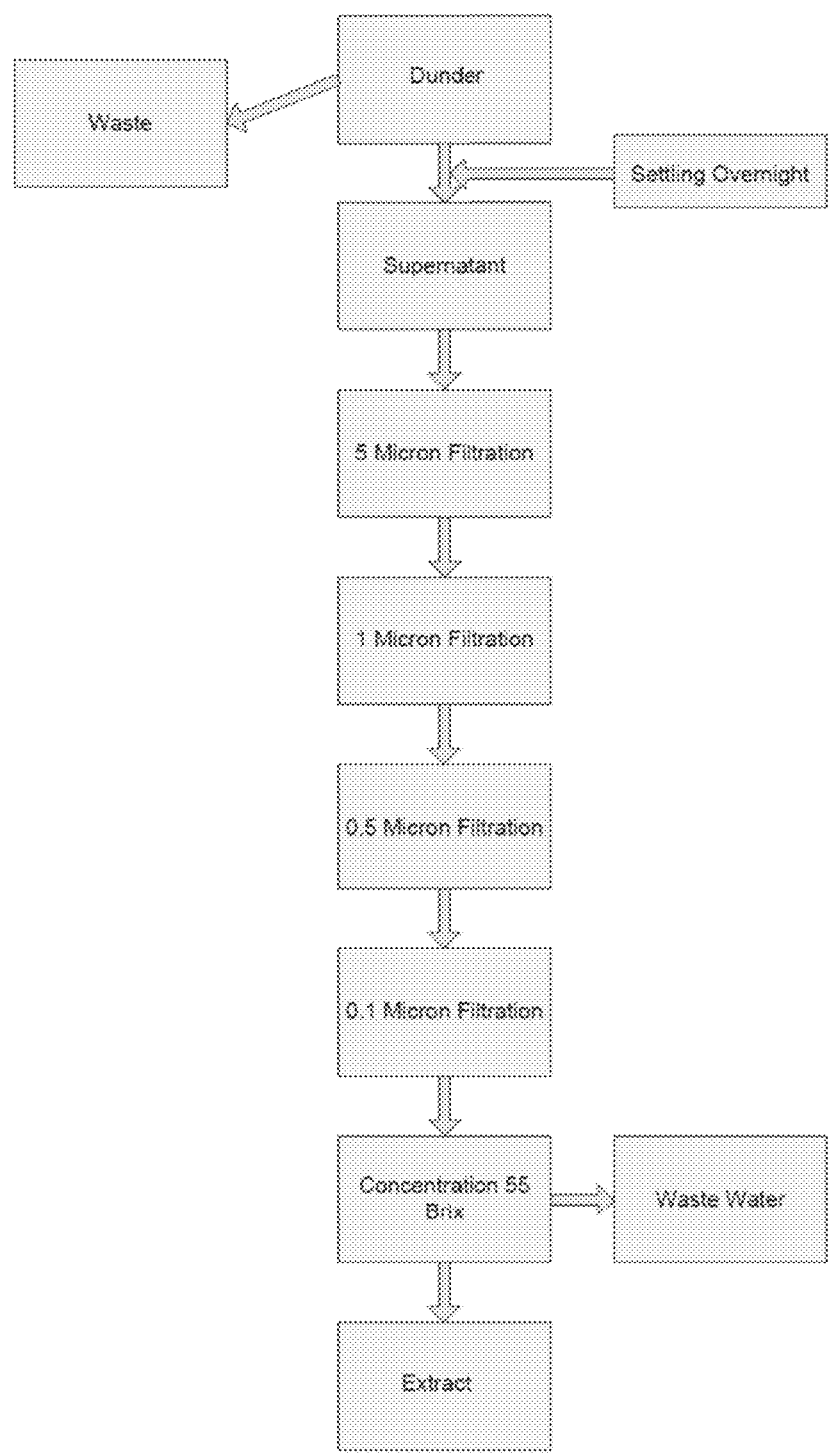
FIG. 9 exhibits a process for the preparation of extracts derived from dunder.

Another exemplary process for producing an extract according to the disclosure is described below. This exemplary process involves multiple filtration steps. This exemplary process with dunder as the sugar cane derived product is depicted in FIG. 9.

Sugar cane dunder is allowed to settled overnight (typically eight hours) in a V-bottom tank. The supernatant is then subjected to a number of filtration steps. The skilled person will understand that a variety of filtration steps (such as, for example, microfiltration or ultrafiltration) may be performed and the appropriate filtration steps will be readily determined by the skilled person.

In one embodiment, the supernatant is subjected to sequential microfiltration. In one embodiment the supernatant is sequentially filtered through: (i) a 5 micron filter; (ii) a 1 micron filter; (iii) a 0.5 micron filter; and (iv) a 0.1 micron filter. The skilled person would understand that a variety of filters could be used in the process to remove the desired sediment and undissolved matter. Exemplary filters are stainless steel filters, ceramic filters and cellulose filters.

The filtered supernatant is subsequently concentrated to remove water providing the extract. Any method for removing the water may be employed, including for example, heat exchange and evaporation. In one embodiment, the filtered supernatant is concentrated in a heat exchanger to remove water until the desired Brix level of the extract is achieved. In one embodiment, the process provides an extract having at least about 40° Bx. In one embodiment, the Bx value of the extract is at least about 50° Bx. In one embodiment, the Bx value of the extract is at least about 55° Bx. In one embodiment, the Bx value of the extract is at least about 60° Bx. In one embodiment, the Bx value of the extract is at least about 70° Bx. In one embodiment, the Bx value of the extract is about 45-55° Bx. In one embodiment, the Bx value of the extract is about 50° Bx. In one embodiment, the Bx value of the extract is about 50-55° Bx. In one embodiment, the Bx value of the extract is about 55-60° Bx. In one embodiment, the Bx value of the extract is about 50-70° Bx.

Exemplary Processes with Mixtures of Sugar Cane Derived Products

Figure 11:
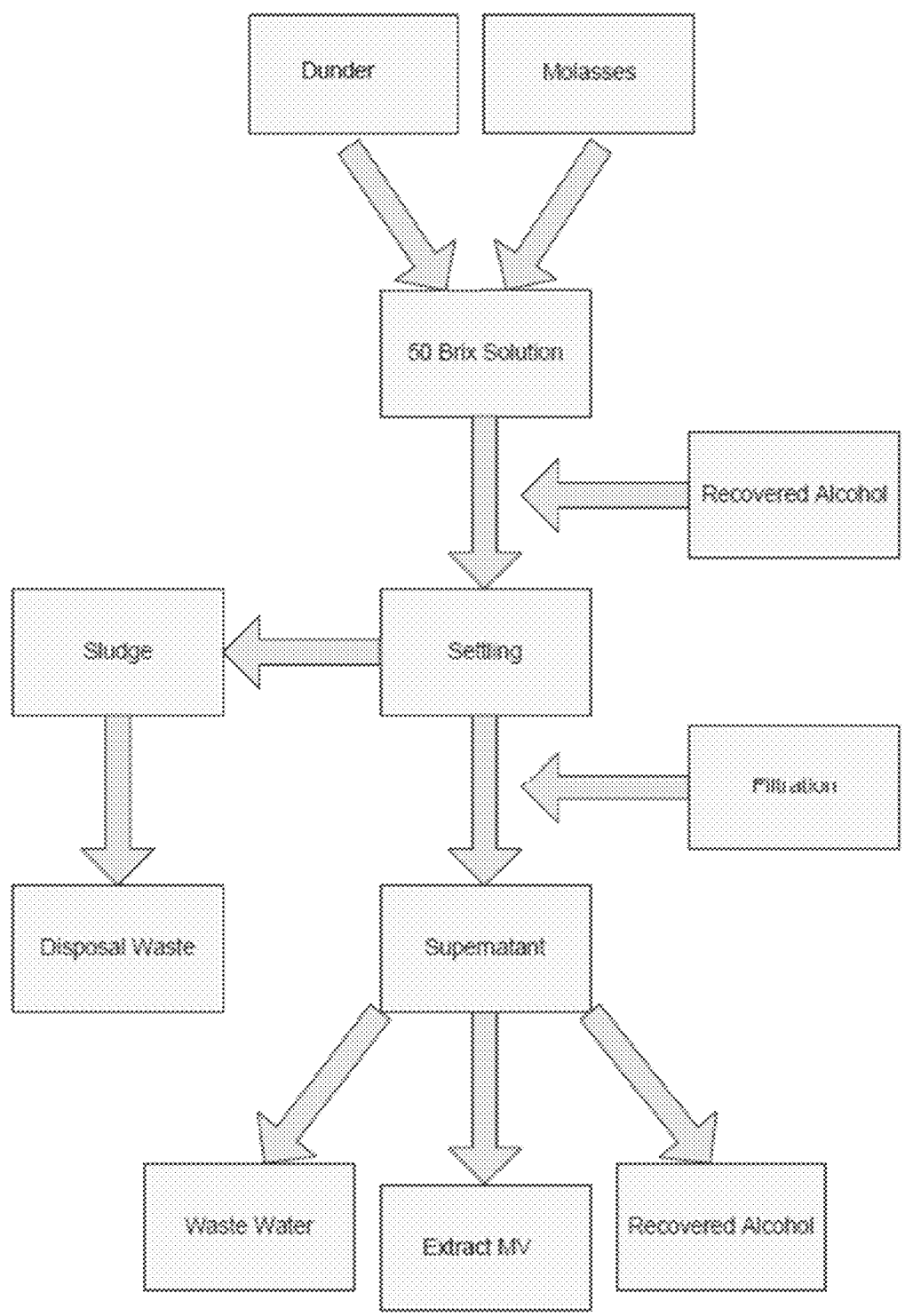
FIG. 11 exhibits a process for the preparation of extracts derived from dunder and molasses.

Another exemplary process for producing an extract according to the disclosure is described below. This exemplary process with a combination of dunder and molasses as the sugar cane derived product is depicted in FIG. 11.

Sugar cane mill molasses is mixed with settled sugar cane dunder (as described above) and stirred well to provide a mixture with the desired Brix level. The skilled person will understand that in order to facilitate mixing of the molasses and dunder, a liquid, for example but not limited to water, may be added. The liquid may be added to the molasses and/or the dunder prior to combining the two or the liquid may be added to the combined molasses and dunder. Additionally, heat may be applied to achieve a desired viscosity. In one embodiment, the combined mixture of molasses and dunder is about 50-55° Bx. In one embodiment, the combined mixture of molasses and dunder is about 50° Bx. In one embodiment, the combined mixture of molasses and dunder is about 55° Bx. In one embodiment, the combined mixture of molasses and dunder is at least about 50° Bx. In one embodiment, the combined mixture of molasses and dunder is at least about 60° Bx. In one embodiment, the combined mixture of molasses and dunder is at least about 70° Bx.

The combined mixture of molasses and dunder is maintained at a constant temperature (for example between 20-25° C.) and ethanol (for example 95% food grade ethanol) is added and stirred to ensure that the ethanol is evenly and quickly dispersed. Ethanol is added until the desired ethanol level is reached. The desired ethanol content can be from about 50% v/v to about 90% v/v. The desired ethanol content can be about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90% v/v. In one embodiment, the desired ethanol level is at least about 60% v/v. In one embodiment, the desired ethanol level is at least about 70% v/v. In one embodiment, the desired ethanol level is at least about 80% v/v. In one embodiment, the desired ethanol level is about 60-70% v/v. In one embodiment, the desired ethanol level is about 70-80% v/v. In one embodiment, the desired ethanol level is about 75% v/v. In one embodiment, the desired ethanol level is about 76% v/v.

The addition and mixing of ethanol may lead to the formation of a gelatinous precipitate. The precipitate in the mixture is allowed to settle and the supernatant is removed, by, for example decantation and/or filtration. In one embodiment, the supernatant is decanted. In one embodiment, the supernatant is filtered. In one embodiment, the supernatant is decanted and filtered.

The ethanol is removed from the supernatant to provide the extract. Any method for removing the ethanol may be employed, including for example, heat exchange and evaporation. In one embodiment, the ethanol is removed by evaporation until the desired Brix level of the extract is achieved. In one embodiment, the process provides an extract having at least about 50° Bx. In one embodiment, the Bx value of the extract is at least about 60° Bx. In one embodiment, the Bx value of the extract is at least about 70° Bx. In one embodiment, the Bx value of the extract is at least about 80° Bx. In one embodiment, the Bx value of the extract is about 50-60° Bx. In one embodiment, the Bx value of the extract is about 60-70° Bx. In one embodiment, the Bx value of the extract is about 70-80° Bx. In one embodiment, the Bx value of the extract is about 65-75° Bx. In one embodiment, the Bx value of the extract is about 75° Bx. In one embodiment, the Bx value of the extract is about 70° Bx.

Extracts Derived from Sugar Cane

As described above, extracts derived from sugar cane generally comprise complex mixtures of substances including, but not limited to, polyphenols, phytosterols, oligosaccharides, polysaccharides, monosaccharide, disaccharides, organic acids, amino acids, peptides, proteins, vitamins, and minerals.

In one embodiment, the extract derived from sugar cane of the present disclosure comprises at least about 10 CE g/L of polyphenols or at least about 150 mg CE/g of polyphenols. As explained above, the term "CE", or "catechin equivalent" is a measure of total polyphenolic content, expressed as mg catechin equivalents/g extract derived from sugar cane or g catechin equivalents/L extract derived from sugar cane.

In one embodiment, the extract derived from sugar cane of the present disclosure comprises at least about 10, 15, 20, 25, 30, 35, 40, 45, 50, 55, 60, 65, 70, 75, 80, 85, 90, 95, or 100 CE g/L of polyphenols.

In one embodiment, the extract derived from sugar cane of the present disclosure comprises at least about 100, 110, 120, 130, 140, 150, 160, 170, 180, 190, 200, 210, 220, 230, 240, 250, 250, 275, 300, 325, 350, 375, 400, 425, 450, 500, 525, 550, 575, 600, 625, 650, 675, 700, 725, 750, 775 or 800 mg CE/g of polyphenols.

In one embodiment, the extract derived from sugar cane of the present disclosure comprises from about 10 CE g/L to about 70 CE g/L of polyphenols or from about 100 CE mg/g to about 700 CE mg/g of polyphenols.

In one embodiment, the extract derived from sugar cane of the present disclosure comprises from about 10 CE g/L to about 60 CE g/L of polyphenols or from about 100 CE mg/g to about 600 CE mg/g of polyphenols.

In one embodiment, the extract derived from sugar cane of the present disclosure comprises from about 10 catechin equivalent (CE) g/L to about 50 CE g/L of polyphenols or from about 100 CE mg/g to about 500 CE mg/g of polyphenols.

In one embodiment, the extract derived from sugar cane of the present disclosure comprises from about 15 catechin equivalent (CE) g/L to about 40 CE g/L of polyphenols or from about 150 CE mg/g to about 400 CE mg/g of polyphenols.

In one embodiment, the extract derived from sugar cane of the present disclosure comprises from about 20 catechin equivalent (CE) g/L to about 30 CE g/L of polyphenols or from about 200 CE mg/g to about 300 CE mg/g of polyphenols.

In one embodiment, the extract derived from sugar cane of the disclosure comprises from about 20 CE g/L to about 27 g CE/L of polyphenols or from about 200 CE mg/g to about 270 CE mg/g of polyphenols.

In one embodiment, the extract derived from sugar cane of the disclosure comprises from about 27 CE g/L to about 35 g CE/L of polyphenols or about 270 CE mg/g to about 350 CE mg/g of polyphenols.

In one embodiment, the extract derived from sugar cane of the disclosure comprises from about 35 CE g/L to about 40 g CE/L of polyphenols or from about 350 CE mg/g to about 400 CE mg/g of polyphenols.

In one embodiment, the extract derived from sugar cane of the disclosure comprises from about 40 CE g/L to about 50 g CE/L of polyphenols or from about 400 CE mg/g to about 500 CE mg/g of polyphenols.

In one embodiment, the extract derived from sugar cane of the disclosure comprises from about 45 CE g/L to about 50 g CE/L of polyphenols or about 450 CE mg/g to about 500 CE mg/g of polyphenols.

The extract derived from sugar cane of the present disclosure may contain the flavonoid class of polyphenols. The extract derived from sugar cane may contain flavonoids in any amount. In one embodiment, the extract derived from sugar cane of the disclosure comprises at least about 1 CE g/L of flavonoids or at least about 10 CE mg/g of flavonoids.

In one embodiment, the extract derived from sugar cane of the disclosure comprises from about 1 CE g/L to about 15 CE g/L of flavonoids or from about 10 CE mg/g to about 150 CE mg/g of flavonoids. In one embodiment, the extract derived from sugar cane of the disclosure comprises from about 3 CE g/L to about 10 CE g/L of flavonoids or about 30 CE mg/g to about 100 CE mg/g of flavonoids. In one embodiment, the extract derived from sugar cane of the disclosure comprises about 5 CE g/L to about 8 CE g/L of flavonoids or about 50 CE mg/g to about 80 CE mg/g of flavonoids. In one embodiment, the extract derived from sugar cane of the disclosure comprises about 6 CE g/L to about 8 CE g/L of flavonoids or about 60 CE mg/g to about 80 CE mg/g of flavonoids. In one embodiment, the extract derived from sugar cane of the disclosure comprises about 6.5 CE g/L to about 7.5 CE g/L of flavonoids or about 65 CE mg/g to about 75 CE mg/g of flavonoids.

The extract derived from sugar cane of the present disclosure may contain the proanthocyanidin class of polyphenols. The extract derived from sugar cane may contain proanthocyandins in any amount. In one embodiment, the extract derived from sugar cane of the present disclosure comprises at least about 1.5 CE g/L of proanthocyanidins or at least about 15 CE mg/g of proanthocyanidins. In one embodiment, the extract derived from sugar cane of the disclosure comprises at least about 1.8 CE g/L of proanthocyanidins or at least about 18 CE mg/g of proanthocyanidins. In one embodiment, the extract derived from sugar cane of the disclosure comprises about 1.5 CE g/L to about 2.5 CE g/L of proanthocyanidins or about 15 CE mg/g to about 25 CE mg/g of proanthocyanidins. In one embodiment, the extract derived from sugar cane of the disclosure comprises about 1.8 CE g/L to about 2.2 CE g/L of proanthocyanidins or about 18 CE mg/g to about 22 CE mg/g of proanthocyanidins.

The extract derived sugar cane of the present disclosure may be a liquid extract. In one embodiment, the liquid extract is a syrup.

The extract derived from sugar cane of the present disclosure may be in a powder form. In one embodiment, the powder form is a freeze dried powder form, or a dehydrated powder form or a spray dried powder form.

The polyphenols of the extract derived from sugar cane of the disclosure include, but are not limited to, one or more of syringic acid, chlorogenic acid, caffeic acid, vanillin, sinapic acid, vitexin, p-coumaric acid, ferulic acid, gallic acid, vanillic acid, diosmin, diosmetin, apigenin, vitexin, orientin, homoorientin, swertisin, tricin, (+)catechin, (−)catechin gallate, (−)epicatechin, quercetin, kaempherol, myricetin, rutin, schaftoside, isoschaftoside, luteolin, scoparin and/or derivatives thereof. The polyphenols of the extract derived from sugar cane of the present disclosure may also include, but are not limited to, one or more of hydroxycinnamic acid, isoorientin, swertiajaponin, neocarlinoside, isovitexin, vicenin, and/or derivatives thereof.

The polyphenols of the extract derived from sugar cane also include conjugates, such as, for example, glycosides, glucosides, galactosides, galacturonides, ethers, esters, arabinosides, sulphates, phosphates, aldopentoses (xylose, arabinose) and aldohexoses.

In one embodiment, the extract derived from sugar cane of the present disclosure comprises syringic acid, chlorogenic acid, caffeic acid, vanillin, sinapic acid, diosmin, diosmetin, apigenin, vitexin, orientin, homoorientin, swertisin, and tricin and/or derivatives thereof.

In one embodiment, the extract derived from sugar cane of the disclosure comprises syringic acid, chlorogenic acid and diosmin and/or derivatives thereof.

In one embodiment, the extract derived from sugar cane of the disclosure comprises syringic acid. In one embodiment, the extract derived from sugar cane of the disclosure comprises chlorogenic acid. In one embodiment, the extract derived from sugar cane of the disclosure comprises diosmin. In one embodiment, the extract derived from sugar cane of the present disclosure comprises caffeic acid. In one embodiment, the extract derived from sugar cane of the present disclosure comprises vanillin. In one embodiment, the extract derived from sugar cane of the present disclosure comprises sinapic acid. In one embodiment, the extract derived from sugar cane of the present disclosure comprises vitexin. In one embodiment, the extract derived from sugar cane of the present disclosure comprises p-coumaric acid. In one embodiment, the extract derived from sugar cane of the present disclosure comprises ferulic acid. In one embodiment, the extract derived from sugar cane of the present disclosure comprises gallic acid. In one embodiment, the extract derived from sugar cane of the present disclosure comprises vanillic acid. In one embodiment, the extract derived from sugar cane of the present disclosure comprises diosmetin. In one embodiment, the extract derived from sugar cane of the present disclosure comprises apigenin. In one embodiment, the extract derived from sugar cane of the present disclosure comprises orientin. In one embodiment, the extract derived from sugar cane of the present disclosure comprises homoorientin. In one embodiment, the extract derived from sugar cane of the present disclosure comprises swertisin. In one embodiment, the extract derived from sugar cane of the present disclosure comprises tricin. In one embodiment, the extract derived from sugar cane of the present disclosure comprises (+)-catechin. In one embodiment, the extract derived from sugar cane of the present disclosure comprises (−)-catechin gallate. In one embodiment, the extract derived from sugar cane of the present disclosure comprises (−)-epicatechin. In one embodiment, the extract derived from sugar cane of the present disclosure comprises quercetin. In one embodiment, the extract derived from sugar cane of the present disclosure comprises kaempherol. In one embodiment, the extract derived from sugar cane of the present disclosure comprises myricetin. In one embodiment, the extract derived from sugar cane of the present disclosure comprises rutin. In one embodiment, the extract derived from sugar cane of the present disclosure comprises schaftoside. In one embodiment, the extract derived from sugar cane of the present disclosure comprises isoschaftoside. In one embodiment, the extract derived from sugar cane of the present disclosure comprises luteolin. In one embodiment, the extract derived from sugar cane of the present disclosure comprises scoparin. In one embodiment, the extract derived from sugar cane of the present disclosure comprises hydroxycinnamic acid. In one embodiment, the extract derived from sugar cane of the present disclosure comprises isoorientin. In one embodiment, the extract derived from sugar cane of the present disclosure comprises swertiajaponin. In one embodiment, the extract derived from sugar cane of the present disclosure comprises neocarlinoside. In one embodiment, the extract derived from sugar cane of the present disclosure comprises isovitexin. In one embodiment, the extract derived from sugar cane of the present disclosure comprises vicenin.

In one embodiment, syringic acid, chlorogenic acid and diosmin are the three most abundant polyphenols of the extract derived from sugar cane of the disclosure.

In one embodiment, the extract derived from sugar cane of the disclosure comprises about 5-20 µg/g dry weight of syringic acid. In one embodiment, the extract derived from sugar cane of the disclosure comprises about 7-15 µg/g dry weight of syringic acid. In one embodiment, the extract derived from sugar cane of the disclosure comprises about 10-12 µg/g dry weight of syringic acid. In one embodiment, the extract derived from sugar cane of the disclosure, when present, comprises about 10.9 µg/g dry weight of syringic acid. The extract derived from sugar cane may be in a syrup form.

In one embodiment, the extract derived from sugar cane of the disclosure comprises about 50-200 µg/g dry weight of syringic acid. In one embodiment, the extract derived from sugar cane of the disclosure comprises about 90-130 µg/g dry weight of syringic acid. In one embodiment, the extract derived from sugar cane of the disclosure comprises about 100-120 µg/g dry weight of syringic acid. In one embodiment, the extract derived from sugar cane of the disclosure comprises about 107 µg/g dry weight of syringic acid. The extract derived from sugar cane may be in a powder form.

In one embodiment, the extract derived from sugar cane of the disclosure comprises about 1-15 µg/g dry weight of chlorogenic acid. In one embodiment, the extract derived from sugar cane of the disclosure comprises about 3-10 µg/g dry weight of chlorogenic acid. In one embodiment, the extract derived from sugar cane of the disclosure comprises about 5-8 µg/g dry weight of chlorogenic acid. In one embodiment, the extract derived from sugar cane of the disclosure comprises about 6.53 µg/g dry weight of chlorogenic acid. The extract derived from sugar cane may be in a syrup form.

In one embodiment, the extract derived from sugar cane of the disclosure comprises about 30-150 µg/g dry weight of chlorogenic acid. In one embodiment, the extract derived from sugar cane of the disclosure comprises about 60-90 µg/g dry weight of chlorogenic acid. In one embodiment, the extract derived from sugar cane of the disclosure comprises about 70-80 µg/g dry weight of chlorogenic acid. In one embodiment, the extract derived from sugar cane of the disclosure comprises about 74 µg/g dry weight of chlorogenic acid. The extract derived from sugar cane may be in a powder form.

In one embodiment, the extract derived from sugar cane of the disclosure comprises about 10-30 µg/g dry weight of diosmin. In one embodiment, the extract derived from sugar cane of the disclosure comprises about 15-25 µg/g dry weight of diosmin. In one embodiment, the extract derived from sugar cane of the disclosure comprises about 18-21 µg/g dry weight of diosmin. In one embodiment, the extract derived from sugar cane of the disclosure comprises about 19-45 µg/g dry weight of diosmin. The extract derived from sugar cane may be in a syrup form.

In one embodiment, the extract derived from sugar cane of the disclosure comprises about 100-300 µg/g dry weight of diosmin. In one embodiment, the extract derived from sugar cane of the disclosure comprises about 190-260 µg/g dry weight of diosmin. In one embodiment, the extract derived from sugar cane of the disclosure comprises about 210-240 µg/g dry weight of diosmin. In one embodiment, the extract derived from sugar cane of the disclosure comprises about 227 µg/g dry weight of diosmin. The extract derived from sugar cane may be in a powder form.

In one embodiment, the extract derived from sugar cane of the present disclosure comprises about 7-15 µg/g dry weight of syringic acid, and/or about 4-9 µg/g dry weight of chlorogenic acid, and/or about 0.1-0.5 µg/g dry weight of caffeic acid, about 0.05-0.3 µg/g dry weight of vanillin, and/or about 0.1-0.3 µg/g dry weight of sinapic acid, and/or about 15-25 µg/g dry weight of diosmin, and/or about 0.1-0.4 µg/g dry weight of orientin, and/or about 0.4-0.9 µg/g dry weight of swertisin, and/or about 0.05-0.3 µg/g dry weight of disomentin. The extract derived from sugar cane may be in a syrup form.

In one embodiment, the extract derived from sugar cane of the present disclosure comprises about 10-12 µg/g dry weight of syringic acid, and/or about 5-8 µg/g dry weight of chlorogenic acid, and/or about 0.2-0.4 µg/g dry weight of caffeic acid, and/or about 0.1-0.2 µg/g dry weight of vanillin, and/or about 0.1-0.25 µg/g dry weight of sinapic acid, and/or about 18-21 µg/g dry weight of diosmin, and/or about 0.2-0.3 µg/g dry weight of orientin, and/or about 0.5-0.8 µg/g dry weight of swertisin, and/or about 0.1-0.2 µg/g dry weight of disomentin. The extract derived from sugar cane may be in a syrup form.

In one embodiment, the extract derived from sugar cane of the present disclosure comprises about 10.9 µg/g dry weight of syringic acid, and/or about 6.53 µg/g dry weight of chlorogenic acid, and/or about 0.29 µg/g dry weight of caffeic acid, and/or about 0.153 µg/g dry weight of vanillin, and/or about 0.18 µg/g dry weight of sinapic acid, and/or about 19.45 µg/g dry weight of diosmin, and/or about 0.245 µg/g dry weight of orientin, and/or about 0.69 µg/g dry weight of swertisin, and/or about 0.15 µg/g dry weight of disomentin. The extract derived from sugar cane may be in a syrup form.

In one embodiment, the extract derived from sugar cane of the present disclosure comprises about 90-130 µg/g dry weight of syringic acid, and/or about 60-90 µg/g dry weight of chlorogenic acid, and/or about 4-10 µg/g dry weight of caffeic acid, and/or about 1-4 µg/g dry weight of vanillin, about 1-3 µg/g dry weight of sinapic acid, and/or about 190-260 µg/g dry weight of diosmin, and/or about 3-7 µg/g dry weight of orientin, and/or 3-8 µg/g dry weight of swertisin, and/or about 0.05-0.3 µg/g dry weight of disomentin. The extract derived from sugar cane may be in a powder form.

In one embodiment, the extract derived from sugar cane of the present disclosure comprises about 100-120 µg/g dry weight of syringic acid, and/or about 70-80 µg/g dry weight of chlorogenic acid, and/or about 6-8 µg/g dry weight of caffeic acid, about 2-3 µg/g dry weight of vanillin, and/or about 1.5-2.5 µg/g dry weight of sinapic acid, and/or about 210-240 µg/g dry weight of diosmin, about 4-5 µg/g dry weight of orientin, 4-6 µg/g dry weight of swertisin, and/or about 0.1-0.2 µg/g dry weight of disomentin. The extract derived from sugar cane may be in a powder form.

In one embodiment, the extract derived from sugar cane of the present disclosure comprises about 107 µg/g dry weight of syringic acid, and/or about 74 µg/g dry weight of chlorogenic acid, and/or about 7.5 µg/g dry weight of caffeic acid, and/or about 2 µg/g dry weight of vanillin, and/or about 1.7 µg/g dry weight of sinapic acid, and/or about 227 µg/g dry weight of diosmin, and/or about 4.5 µg/g dry weight of orientin, 5.2 µg/g dry weight of swertisin, and/or about 0.16 µg/g dry weight of disomentin. The extract derived from sugar cane may be in a powder form.

The extract derived from sugar cane of the present disclosure may contain a range of organic acids that are found naturally in sugar cane. These organic acids may include, but are not limited to, aconitic (cis- and trans-), oxalic, citric, tartaric, lactic, glycolic, succinic, malic, fumaric and shikimic acids. In one embodiment, the extract derived from sugar cane contains higher levels of citric and malic acids than other organic acids. In one embodiment, the extract derived from sugar cane contains lactic acid. In one embodiment, the extract derived from sugar cane contains glycolic acid. In one embodiment, the extract derived from sugar cane contains oxalic, citric, tartaric, lactic, glycolic, succinic and malic acids. In another embodiment, the extract derived from sugar cane contains low to trace amounts of oxalic, citric, tartaric, lactic, glycolic, succinic and malic acids. In another embodiment, the two most abundant organic acids in the extract derived from sugar cane are trans- and cis-aconitic acids.

The extract derived from sugar cane of the present disclosure may contain trans- and/or cis-aconitic acids. In one embodiment, the extract derived from sugar cane of the present disclosure comprises trans-aconitic in amount of about 10,000-40,000 mg per kg and/or cis-aconitic in amount of about 3,000-7,000 mg/kg. In one embodiment, the extract derived from sugar cane of the present disclosure may contain trans-aconitic in an amount of about 17,000-30,000 mg per kg and/or cis-aconitic in amount of about 4,000-6,500 mg/kg. In one embodiment, the extract derived from sugar cane of the present disclosure may contain trans-aconitic in amount of about 20,000-25,000 mg per kg and/or cis-aconitic in amount of about 5,000-5,500 mg/kg.

The extract derived from sugar cane of the present disclosure may contain lactic acid and/or glycolic acid. In one embodiment, the extract derived from sugar cane of the present disclosure comprises lactic acid in amount of about 100-5,000 mg per kg. In one embodiment, the extract derived from sugar cane of the present disclosure comprises lactic acid in amount of about 100-3,000 mg per kg. In one embodiment, the extract derived from sugar cane of the present disclosure comprises lactic acid in amount of about 100-1,000 mg per kg. In one embodiment, the extract derived from sugar cane of the present disclosure comprises lactic acid in amount of about 100-500 mg per kg. In one embodiment, the extract derived from sugar cane of the present disclosure comprises glycolic acid in amount of about 10-5,000 mg per kg. In one embodiment, the extract derived from sugar cane of the present disclosure comprises glycolic acid in amount of about 100-5,000 mg per kg. In one embodiment, the extract derived from sugar cane of the present disclosure comprises glycolic acid in amount of about 100-3,000 mg per kg. In one embodiment, the extract derived from sugar cane of the present disclosure comprises glycolic acid in amount of about 100-1,000 mg per kg. In one embodiment, the extract derived from sugar cane of the present disclosure comprises glycolic acid in amount of about 100-500 mg per kg.

The extract derived from sugar cane of the present disclosure may contain amino acids. In one embodiment, the total amino acids levels of the extract derived from sugar cane of the present disclosure is about 50,000-80,000 µg per gram, or about 60,000-70,000 µg per gram, or about 65,000 µg per gram. In one embodiment, about 10-40% of these total amino acids are essential amino acids. In one embodiment, about 15-30% of these total amino acids are essential amino acids. In one embodiment, about 20-25% of these total amino acids are essential amino acids.

The extract derived from sugar cane of the present disclosure may contain free amino acids. In one embodiment, the extract derived from sugar cane of the present disclosure comprises about 10,000-50,000 µg of free amino acids per gram. In one embodiment, the extract derived from sugar cane of the present disclosure may contain about 20,000-35,000 µg of free amino acids per gram. The extract derived from sugar cane of the present disclosure may contain about 25,000-30,000 µg of free amino acids per gram.

As defined above, the term "free amino acids" as used herein refers to amino acids which are singular molecules and structurally not attached to peptide bonds which are attached to other amino acids.

The extract derived from sugar cane of the present disclosure may contain leucine, a branched chain essential amino acid. In one embodiment, the concentration of leucine in the extract derived from sugar cane, is about 1-5 mM, or about 1.5-4 mM, or about 2-3 mM. In one embodiment, the amount of leucine in the extract derived from sugar cane is about 1,000-20,000 µg per gram, or about 1,000-10,000 µg per gram, or about 1,000-5,000 µg per gram, or about 1,000-2,000 µg per gram, or about 5,000-10,000 µg per gram, or about 10,000-20,000 µg per gram.

The extract derived from sugar cane of the present disclosure may contain minerals. In one embodiment, the extract derived from sugar cane derived from sugar cane contains minerals that are found naturally in sugar cane. In one embodiment, the extract derived from sugar cane derived from sugar contains one or more minerals including, but not limited to, potassium, sodium, calcium, magnesium, iron, zinc, selenium and chromium.

In one embodiment, the extract derived from sugar cane contains minerals bound to the polyphenols. In one embodiment, the extract derived from sugar cane contains divalent ions bound to the polyphenols. In one embodiment, the extract derived from sugar cane contains calcium, magnesium and/or iron bound to the polyphenols. In one embodiment, the extract derived from sugar cane contains iron bound to the polyphenols.

In one embodiment, the extract derived from sugar cane of the present disclosure comprises about 20,000-32,000 mg of potassium per kilogram, and/or about 300-600 mg of sodium per kilogram, and/or about 800-1,300 mg of calcium per kilogram, and/or about 3,000-6,000 mg of magnesium per kilogram, and/or about 40-90 mg of iron per kilogram, and/or about 3-10 mg of zinc per kilogram, and/or about 500-900 µg of selenium per kilogram and/or about 1,000-1,600 µg of chromium per kilogram. The extract derived from sugar cane may be in a syrup form.

In one embodiment, the extract derived from sugar cane of the present disclosure comprises about 25,000-27,000 mg of potassium per kilogram, and/or about 400-500 mg of sodium per kilogram, and/or about 1,000-1,200 mg of calcium per kilogram, and/or about 4,000-5,500 mg of magnesium per kilogram, and/or about 55-75 mg of iron per kilogram, and/or about 5.5-7.5 mg of zinc per kilogram, and/or about 700-850 µg of selenium per kilogram, and/or about 1,200-1,400 µg of chromium per kilogram. The extract derived from sugar cane may be in a syrup form.

In one embodiment, the extract derived from sugar cane of the present disclosure comprises about 26,000 mg of potassium per kilogram, and/or about 450 mg of sodium per kilogram, and/or about 1,090 mg of calcium per kilogram, and/or about 4,700 mg of magnesium per kilogram, and/or about 65 mg of iron per kilogram, about 6.6 mg of zinc per kilogram, and/or about 786 µg of selenium per kilogram and/or about 1,300 µg of chromium per kilogram. The extract derived from sugar cane may be in a syrup form.

In one embodiment, the extract derived from sugar cane of the present disclosure comprises about 50-350 mg of potassium per kilogram, and/or about 5-70 mg of sodium per kilogram, and/or about 7,000-10,000 mg of calcium per kilogram, and/or about 1,000-3,000 mg of magnesium per kilogram, and/or about 500-1,300 mg of iron per kilogram. The extract derived from sugar cane may be in a powder form.

In one embodiment, the extract derived from sugar cane of the present disclosure comprises about 100-250 mg of potassium per kilogram, and/or about 10-50 mg of sodium per kilogram, and/or about 8,000-9,000 mg of calcium per kilogram, and/or about 1,500-2,500 mg of magnesium per kilogram, and/or about 800-1,000 mg of iron per kilogram. The extract derived from sugar cane may be in a powder form.

In one embodiment, the extract derived from sugar cane of the present disclosure comprises about 190 mg of potassium per kilogram, and/or about 30 mg of sodium per kilogram, and/or about 8,800 mg of calcium per kilogram, and/or about 2,000 mg of magnesium per kilogram, and/or about 890 mg of iron per kilogram. The extract derived from sugar cane may be in a powder form.

The extract derived from sugar cane of the present disclosure may contain monosaccharides, disaccharides, oligosaccharides and/or polysaccharides. Examples of these include, but are not limited to, sucrose, glucose, galactose, xylose, ribose, mannose, rhamnose, fructose, maltose, lactose, maltotriose, xylopyarnose, raffinose, 1-kestose, theanderose, 6-kestose, panose, neo-kestose and nystose, glucans and xylans.

The extract derived from sugar cane of the present disclosure may contain fiber. The fiber may be present in the extract as obtained by the process or fiber may be added to the extract. The term "fiber" as used herein refers to indigestible portion of food derived from plants. The fiber may be soluble or insoluble fiber. Non-limiting examples of fiber include, sugar cane fiber, oat bran, flour (including, for example soy, rice, wheat, bran, rye, corn, sorghum, potato), modified starch, gelatin, non-starch polysaccharides such as arabinoxylans, cellulose, chia fiber, psyillium fiber, fenugreek fiber and many other plant components such as resistant starch, resistant dextrins, inulin, lignin, chitins, pectins, beta-glucans, and oligosaccharides. In one embodiment, the extract derived from sugar cane of the present disclosure contains sugar cane fiber. In one embodiment, the extract derived from sugar cane of the present disclosure contains flour. In one embodiment, the extract derived from sugar cane of the present disclosure contains modified starch. In one embodiment, the extract derived from sugar cane of the present disclosure contains cellulose. In one embodiment, the extract derived from sugar cane of the present disclosure contains chia fiber. In one embodiment, the extract derived from sugar cane of the present disclosure contains pysillium fiber. In one embodiment, the extract derived from sugar cane of the present disclosure contains fenugreek fiber.

In one embodiment, the fiber is present in the extract of the present disclosure. In one embodiment, the fiber is added to the extract of the present disclosure.

It may be desirable that extremes of pH of the extract derived from sugar cane or the supernatant of the present disclosure be avoided. In one embodiment, the pH of the extract or the supernatant derived from sugar cane of the present disclosure is in the range of about 3 to about 7, or about 3 to about 6, or about 4 to about 5.5, or about 4.5 to about 5, or about 4.6 to about 4.8.

The Brix value of the extract derived from sugar cane of the present disclosure may vary. In some instances the Bx value of the extract is at least about 40° Bx (degrees Brix). In some instances the Bx value of the extract is at least about 50° Bx. In some instances the extract of the present disclosure has at least about 60° Bx (degrees Brix). In some instances the Bx value of the extract is at least about 65° Bx. In some instances the Bx value of the extract is at least about 70° Bx. In some instances the Bx value of the extract is about 50-75° Bx. In some instances the Bx value of the extract is about 50-70° Bx. In some instances the Bx value of the extract is about 60-65° Bx. In some instances the Bx value of the extract is about 50-60° Bx. In some instances the Bx value of the extract is about 55° Bx. In some instances the Bx value of the extract is about 60-65° Bx. In some instances the Bx value of the extract is about 64-65° Bx. In some instances the Bx value of the extract is about 65-70° Bx. In some instances the Bx value of the extract is about 70-75° Bx. In some instances the Bx value of the extract is about 75-80° Bx.

Compositions, Methods and Uses of the Extracts Derived from Sugar Cane

The extracts derived from sugar cane of the present disclosure may be added to compositions and may have application in various uses and methods.

In one aspect of the disclosure there is provided a composition comprising an extract derived from sugar cane comprising polyphenols of the present disclosure for preventing, improving or treating a skin condition.

In one embodiment, there is provided a composition comprising an extract derived from sugar cane for use in preventing, improving or treating a skin condition, the extract comprising from about 10 catechin equivalent (CE) g/L to about 50 CE g/L of polyphenols or from about 100 CE mg/g to about 500 CE mg/g of polyphenols.

The extracts derived from sugar cane of the present disclosure, together with a conventional adjuvant, carrier or diluent, may be placed into the form of pharmaceutical or cosmeceutical compositions and unit dosages thereof, and in such form may be employed as solids, such as tablets, powders or filled capsules, liquids as solutions, suspensions, emulsions (including microemulsions), syrups, elixirs or capsules filled with the same, lotions, creams, serums, gels, ointments and oils.

Compositions include those for oral, topical and injection administration. In one embodiment, the composition is for oral administration. In another embodiment, the composition is for topical administration. In another embodiment, the composition is for injection administration.

In one embodiment, the composition is in the form of a tablet or capsule. In one embodiment, the composition is in the form of a tablet. In one embodiment, the composition is in the form of a capsule. In one embodiment, the composition is in the form of a liquid. In one embodiment, the composition is in the form of a syrup.

In one embodiment, the composition is in the form of a lotion, cream, serum or gel. In one embodiment, the composition is in the form of a cream, serum or gel. In one embodiment, the composition is in the form of a lotion. In one embodiment, the composition is in the form of a cream. In one embodiment, the composition is in the form of a serum. In one embodiment, the composition is in the form of a gel.

The compositions of the present disclosure may take the form of any type of product that is desired. For example, but not limited to, the compositions may be face and/or body creams or gels, hand and/or foot creams or gels, shower and/or bath products (including for example, soaps, hand and/or body washes, shower gels, face washes, cleansers, toners, exfoliators, shampoos, conditioners) and sun care products (including for example sun creams, sun blocks and sun screens as lotions, sprays, creams or gels and after-sun products).

In one embodiment, the composition is a face and/or body cream or gel, hand and/or foot cream or gel, shower and/or bath product or sun care product. In one embodiment, the composition is a face and/or body cream or gel. In one embodiment, the composition is a face cream or gel. In one embodiment, the composition is a body cream or gel. In one embodiment, the composition is a hand and/or foot cream or gel. In one embodiment, the composition is a hand cream or gel. In one embodiment, the composition is a shower and/or bath product. In one embodiment, the composition is a sun care product.

The composition comprising an extract derived from sugar cane of the present disclosure, contains one or more pharmaceutically and/or cosmeceutically acceptable carriers, diluents and/or excipients. By "pharmaceutically and/or cosmeceutically acceptable" it is meant the carrier, diluent or excipient must be compatible with the other ingredients of the formulation and not deleterious to the recipient thereof. A composition may also be described inter alia as a medicament or formulation.

The compositions may also include excipients and other additives, including but not limited to, gelling agents, thickeners, plasticizers, stabilisers, moisturisers, emollients, penetration enhancers, detergents, colouring agents, wetting or emulsifying agents, humectants, surfactants, transport enhancers, pH adjusting agents, preservatives, fragrances and the like.

The compositions may include any and all solvents, dispersion media, coatings, anti-bacterial and anti-fungal agents, isotonic and absorption delaying agents and the like. The use of such media and agents for pharmaceutical and cosmeceutical compositions is well known in the art and except insofar as any conventional media or agent is incompatible with the active ingredient; their use in the compositions as described herein is contemplated.

Penetration enhancers can be selected from the group, but are not limited to, propylene glycol, calcium chelators such as EDTA, methylated P-cyclodextrin, and polycarboxylic acids; surfactants such as sodium lauryl sulfate, sodium dodecyl sulfate, carnitine, carnitine esters, and tween; bile salts such as sodium taurocholate; fatty acids such as oleic and linoleic acid; and non-surfactants such as dialkyl sulfoxides; E-flux inhibitors such as D-a-tocopheryl polyethylene glycol 1000 succinate (TPGS), and peppermint oil; chitosan and chitosan derivatives such as N-methyl chitosan, N-trimethyl chitosan, mono-N-carboxymethyl chitosan, quaternized chitosan derivatives; SNAC (N-(8-(2-hydroxybenzoyl) amino) caprylate) and SNAD (N-(10-(2-hydroxybenzoyl)amino)-decanoate); N-acylated non-alpha amino acids; Gelucire 44/14 or Vitamin E TPGS; CARBOPOL® 934P; others known to those of ordinary skill in the art; and combinations thereof.

Gelling agents can be selected from the group, but are not limited to, acacia, alginic acid, bentonite, carbopols, carbomer 940, carbomer 941, gelatin, carbomer copolymer, aluminum monostearat, dextrin, magnesium aluminum silicate, silicon dioxide, sodium alginate, triethanolamine, polyvinyl alcohol, pectin, methylcellulose, hydroxypropyl cellulose, aqueous thickening agents such as neutral, anionic-cationic polymers and other materials known to one of ordinary skill in the art and mixtures thereof.

pH adjusting agents can be selected from the group, but are not limited to, triethanolamine, triethylamine, diethylmethylamine, ethyldimethylamine, isopropyldimethylamine-.one or more adipic acids, glycines, citric acids, calcium hydroxides, magnesium aluminometasilicates, buffers, typically Bronsted-Lowry and/or Lewis acids and/or bases, or any combinations thereof and other materials known to one of ordinary skill in the art.

Moisturisers can be selected from the group, but are not limited to, polyethylene glycol, propylene glycol, dipropylene glycol, 1,3-butylene glycol, glycerin, diglycerin, xylitol, maltitol, maltose, D-mannitol, glucose, fructose, sodium chondroitin sulfate, sodium hyaluronate, sodium lactate, glucosamine, cyclodextrin, cococaprylate/caprate and other materials known to one of ordinary skill in the art and mixtures thereof.

Emulsifiers can be selected from the group, but are not limited to, sodium lauryl sulfate, ceteth-20, laureth-3, glyceryl stearate, polyethylene glycol, macrogol cetostearyl ether, stearic acid, stearyl alcohol, polysorbate 60, Irish moss, Tween 80, sorbitol monostearate·glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanol amine cetyl phosphate, polysorbate 60, glyceryl stearate, PEG-100 stearate, tragacanth gum, 10-30 alkyl acrylate crosspolymers and other materials known to one of ordinary skill in the art and mixtures thereof.

Emollients can be selected from the group, but are not limited to, liquid vaseline. paraffinum liquidum, petrolatum, proplylene glycol, fatty acid esters, mineral oil including dimethicone, waxes including white wax, spermacetic wax, squalene, cetearyl alcohol, cetostearyl alcohol, stearyl alcohol, 2-Octyldodecanol, mineral oil USP, light mineral oil NF, liquid paraffin BP, light liquid paraffin BP, candelilla wax, sweet almond oil, apricot oil, emu oil, argan oil, glycerin, coconut oil, grape seed oil, honey, lanolin and other materials known to one of ordinary skill in the art and mixtures thereof.

Surfactants can be selected from the group, but are not limited to, a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkylyl ether, polyoxyethylene cetyl ether, polyoxyethylene palmityl ether, polyethylene oxide hexadecyl ether, polyethylene glycol cetyl ether, a sucrose ester, a partial ester of sorbitol, sorbitan monolaurate, sorbitan monolaurate a monoglyceride, a diglyceride, isoceteth-20, a sucrose ester, or selected from the group consisting of steareth 2, glyceryl monostearate/PEG 100 stearate, Glyceryl Stearate, Steareth-21, peg 40 stearate, polysorbate 60, polysorbate 80, sorbitan stearate, laureth 4, Sorbitan monooleate, ceteareth 20, steareth 20, ceteth 20, Macrogol Cetostearyl Ether, ceteth 2, PEG-30 Dipolyhydroxystearate, sucrose distearate, polyoxyethylene (100) stearate, PEG 100 stearate, laureth 4, cetomacrogol ether, cetearyl alcohol, cetearyl glucoside, oleyl alcohol, steareth-2, diisopropyl adipate, capric/caprilic triglicerides, polysorbate 20, montanov 68 (cetearyl alcohol (and) cetearyl glucoside), sharonmix 824 (a liquid blend of methyl paraben, ethyl paraben and propyl paraben—in phenoxyethanol), Simusol 165 (glyceryl stearate and PEG-100 stearate), methyl glucose sequistearate, Peg 30 dipolyhydroxystearate, sucrose stearic acid esters, sorbitan laureth, sorbitan stearate, sodium lauryl sulfate, and mixtures thereof.

Preservatives can be selected from the group, but not limited to, methylparaben and propylparaben and the salts thereof (e.g. sodium or potassium salts), sodium benzoate, diazolidinyl urea, phenoxyethanol, DMDM hydantoin, sorbic acid, benzyl alcohol, formaldehyde, triclosan·methylisothiazolinone, methylchloroisothiazolinone, caffeine, citric acid, benzoic acid, butylated hydroxytoluene, propylene glycol, organic acids, esters of parahydroxybenzoic acid (methyl, ethyl, propyl and butyl esters of parahydroxy benzoic acid, and their sodiumsalts etc), chloform, chlorocresol, quaternary ammonium compounds and butylated hydroxyanisole, and the mixtures thereof.

Solvents can be selected from the group, but not limited to, ethyl alcohol, polyethylene glycol, propylene glycol, isopropyl alcohol, purified water and other materials known to one of ordinary skill in the art and mixtures thereof.

Thickeners can be selected from the group, but not limited to, beeswax, cocoa butter, shea butter, wool wax, cetyl alcohol, gum acacia, gum tragacanth, locust bean gum, guar gum, hydroxypropyl guar, xanthan gum, cellulose gum, *sclerotium* gum, carrageenan gum, karaya gum, cellulose gum, rosin, anionic polymers such as polyacrylic acid, carboxymethylcellulose, methylcellulose, hydroxyethylcellulose, hydroxypropylcellulose, hydroxymethylcellulose, polyethylene glycol, acrylic acid polymers, PEG-150 distearate, decyl alcohol, SMDI copolymer, faponite XLG, ethyl cellulose, natrosol and other materials known to one of ordinary skill in the art and mixtures thereof.

Plasticizers can be selected from the group, but not limited to, glycerol, propylene glycol or another glycol, peppermint oil, eucalyptol oil, geranyl acetate or geraniol, phthalate, sebacate and citrate esters, triacetin, sorbitol, sucrose, triethyl citrate, dibutyl phthalate and other materials known to one of ordinary skill in the art and mixtures thereof.

Compositions of the present disclosure may be formulated, for example, by employing conventional solid or liquid vehicles or diluents, as well as additives of a type appropriate to the mode of desired administration (for example, excipients, binders, preservatives, stabilizers, flavours, lubricants, disintegrating agents, etc.) according to techniques such as those well known in the art of formulation. The composition comprising an extract derived from sugar cane may be contained within matrixes, nanoparticles, liposomes, vesicles, microcapsules, microspheres and the like, or within a solid particulate material.

For example, but not limited to, a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be included in the composition of the present disclosure.

The topical compositions of the present disclosure, e.g. in the form of lotions, creams or gels, may contain acceptable diluents, carriers and other excipients to impart the desired texture, consistency, viscosity and appearance. Acceptable diluents, carriers and other excipients are familiar to those skilled in the art and include, but are not limited to, skin penetration enhancers, ethoxylated and nonethoxylated surfactants, fatty alcohols, fatty acids, hydrocarbon oils (such as palm oil, coconut oil, and mineral oil), cocoa butter waxes, silicon oils, buffering agents, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

In one embodiment, the composition comprises a skin penetration enhancer.

Various other materials may be present as coatings or to otherwise modify the physical form of the dosage unit. For instance, tablets, pills or capsules may be coated with shellac, sugar or both. A syrup or elixir may contain sucrose as a sweetening agent, and/or methyl and propylparabens as preservatives, and/or a dye and/or a flavouring. Any material used in preparing any dosage unit form should be pharmaceutically pure and substantially non-toxic in the amounts employed.

Generally, injection compositions of the present disclosure are low-viscosity, sterile formulations. The injection compositions may contain, in addition to the extract derived from sugar cane, other ingredients typically used in such products, such as antimicrobials, hydration agents, tissue bulking agents or tissue fillers, preservatives, emulsifiers, natural or synthetic oils, solvents, surfactants, detergents, buffers, gelling agents, antioxidants, fillers, thickeners, powders, viscosity-controlling agents and water, and optionally including anaesthetics, anti-itch actives, conditioning agents, minerals, silicones or derivatives thereof, amino acids and vitamins.

Injectable compositions of the present disclosure may be in the form of controlled-release or sustained-release compositions which comprise the extract derived from sugar cane and a material such that they are released within the tissue in a controlled manner over time. The composition comprising the extract derived from sugar cane may be contained within matrixes, nanoparticles, liposomes, vesicles, microcapsules, microspheres and the like, or within a solid particulate material, all of which is selected and/or constructed to provide release of the extract derived from sugar cane over time.

The compositions of the present disclosure may conveniently be presented in dosage unit form and may be prepared by any of the methods well known in the art of formulation. Exemplary techniques for formulation of the compositions of the present disclosure may be found in "Remington's Pharmaceutical Sciences", Mack Publishing Co., Easton Pa., 22$^{nd}$ edition, 2012. Some methods include the step of bringing the extract derived from sugar cane of the present disclosure, into association with the carrier which constitutes one or more accessory ingredients. In general, the compositions are prepared by uniformly and intimately bringing the extract derived from sugar cane of the present disclosure, into association with a liquid carrier or a finely divided solid carrier or both, and then, if necessary, shaping the product into the desired formulation. In the composition the extract derived from sugar cane is included in an amount sufficient to produce the desired effect upon the skin condition. As used herein, the term "composition" is intended to encompass a product comprising the specified ingredients in the specified amounts, as well as any product which results, directly or indirectly, from combination of the specified ingredients in the specified amounts.

The compositions of the present disclosure may also comprise other therapeutically active compounds which can be applied in the prevention, improvement and treatment of skin conditions. Selection of the appropriate active compounds for use in combination therapy may be made by one of ordinary skill in the art, according to conventional pharmaceutical principles. The combination of active compounds may act synergistically to effect the prevention, improvement or treatment of the various skin conditions. Using this approach, one may be able to achieve therapeutic efficacy with lower dosages of each active compound, thus reducing the potential for adverse side effects.

The compositions of the present disclosure may also comprise, for example, alpha hydroxyl acids (e.g. glycolic, lactic, tartaric, and citric acids), beta hydroxyl acids (e.g. salicylic acid), hydroquinone, kojic acid, benzaldehyde-O-alkyloximes, retinol, tretinoin (and other vitamin A derivatives), L-ascorbic acid, hyaluronic acid, vitamin C and derivatives thereof, vitamin E and derivatives thereof, copper peptide, alpha-lipoic acid, dimethylaminoethanol, coenzyme Q-10, salicylic acid and benzoyl peroxide.

In one embodiment the compositions of the present disclosure include lactic acid and/or glycolic acid. Lactic acid and glycolic acid have previously been used in skin products for their ability to hydrate (moisturise) and exfoliate. The dual function of exfoliation and moisturisation removes damaged, dry and dead skin cells and promotes growth of new cells. Lactic acid and glycolic acid have also previously been used in skin products for their ability to lighten and brighten the skin. Extracts derived from sugar cane comprising lactic acid and/or glycolic acid of the present disclosure are therefore useful in preventing, improving or treating skin conditions.

In one embodiment, the compositions of the present disclosure comprise lactic acid and/or glycolic acid in amount of about 0.01-30 wt % based upon the total weight of the composition. In one embodiment, lactic acid and/or glycolic acid is present in an amount from about 0.05 wt % to about 25 wt %. In one embodiment, lactic acid and/or glycolic acid is present in an amount from about 5 wt % to about 20 wt %. In one embodiment, lactic acid and/or glycolic acid is present in an amount from about 1 wt % to about 20 wt %. In one embodiment, lactic acid and/or glycolic acid is present in an amount from about 0.1 wt % to about 10 wt %. In one embodiment, lactic acid and/or glycolic acid is present in an amount from about 1 wt % to about 10 wt %. In one embodiment, lactic acid and/or glycolic acid is present in an amount from about 1 wt % to about 5 wt %. In one embodiment, lactic acid and/or glycolic acid is present in an amount from about 0.05 wt % to about 5 wt %. In one embodiment, lactic acid and/or glycolic acid is present in an amount from about 1 wt % to about 3 wt %. In one embodiment, lactic acid and/or glycolic acid is present in an amount from about 3 wt % to about 8 wt %. In one embodiment, lactic acid and/or glycolic acid is present in an amount from about 5 wt % to about 10 wt %. In one embodiment, lactic acid and/or glycolic acid is present in an amount from about 5 wt % to about 20 wt %.

When other therapeutically active compounds are employed in combination with the extracts derived from sugar cane of the present disclosure, they may be used, for example, in amounts as noted in the Physicians' Desk Reference (PDR) or as otherwise determined by one of ordinary skill in the art.

The compositions of the present disclosure comprise the extracts derived from sugar cane of the present disclosure in an amount of at least 0.05 wt % based upon the total weight of the composition. The percentage of the extract derived from sugar cane in the compositions may, of course, be varied and may be between about 0.05 wt % to about 50 wt % based upon the total weight of the composition. The amount of the extracts derived from sugar cane of the present disclosure in compositions is such that a suitable dosage will be obtained.

In one embodiment, the extract derived from sugar cane is present in an amount from about 0.05 wt % to about 50 wt % based upon the total weight of the composition. In one embodiment, the extract derived from sugar cane is present in an amount from about 1 wt % to about 30 wt % based upon the total weight of the composition. In one embodiment, the extract derived from sugar cane is present in an amount from about 5 wt % to about 20 wt % based upon the total weight of the composition. In one embodiment, the extract derived from sugar cane is present in an amount from about 1 wt % to about 20 wt % based upon the total weight of the composition. In one embodiment, the extract derived from sugar cane is present in an amount from about 0.1 wt % to about 10 wt % based upon the total weight of the composition. In one embodiment, the extract derived from sugar cane is present in an amount from about 1 wt % to about 10 wt % based upon the total weight of the composition. In one embodiment, the extract derived from sugar cane is present in an amount from about 1 wt % to about 5 wt % based upon the total weight of the composition. In one embodiment, the extract derived from sugar cane is present in an amount from about 0.05 wt % to about 10 wt % based upon the total weight of the composition. In one embodiment, the extract derived from sugar cane is present in an amount from about 0.5 wt % to about 5 wt % based upon the total weight of the composition. In one embodiment, the extract derived from sugar cane is present in an amount from about 0.5 wt % to about 2.5 wt % based upon the total weight of the composition. In one embodiment, the extract derived from sugar cane is present in an amount from about 1 wt % to about 3 wt % based upon the total weight of the composition. In one embodiment, the extract derived from sugar cane is present in an amount from about 2.5 wt % to about 5 wt % based upon the total weight of the composition. In one embodiment, the extract derived from sugar cane is present in an amount from about 2 wt % to about 6 wt % based upon the total weight of the composition. In one embodiment, the extract derived from sugar cane is present in an amount from about 3 wt % to about 8 wt % based upon the total weight of the composition. In one embodiment, the extract derived from sugar cane is present in an amount from about 5 wt % to about 10 wt % based upon the total weight of the composition. In one embodiment, the extract derived from sugar cane is present in an amount from about 5 wt % to about 20 wt % based upon the total weight of the composition.

In the prevention, improvement or treatment of skin conditions, an appropriate dosage level will generally be about 10 to 5000 mg of the extract derived from sugar cane of the present disclosure per day which can be administered in single or multiple doses. In one embodiment, the dosage level will be about 10 to about 5,000 mg per day. In one embodiment, the dosage level will be about 10 to about 1,000 mg per day. In one embodiment, the dosage level will be about 10 to about 500 mg per day. In one embodiment, the dosage level will be about 100 to about 1,000 mg per day. In one embodiment, the dosage level will be about 100 to about 2,000 mg per day. In one embodiment, the dosage level will be about 100 to about 3,000 mg per day. In one embodiment, the dosage level will be about 100 to about 4,000 mg per day. In one embodiment, the dosage level will be about 100 to about 5,000 mg per day. In one embodiment, the dosage level will be about 250 to about 4,000 mg per day. In one embodiment, the dosage level will be about 500 to about 3,000 mg per day. In one embodiment, the dosage level will be about 1,000 to 2,000 mg per day. In one embodiment, the dosage level will be about 2,000 to 5,000 mg per day. In one embodiment, the dosage level will be about 2,000 to 4,000 mg per day. In one embodiment, the dosage level will be about 2,000 to 3,000 mg per day.

It will be understood, however, that the specific dosage level and frequency of dosage for any particular patient may be varied and will depend upon a variety of factors including the activity of the specific extract derived from sugar cane employed, the metabolic stability and length of action of that extract derived from sugar cane, the age, body weight, general health, sex, diet, mode and time of administration, rate of excretion, drug combination, the severity of the particular condition, and the subject undergoing therapy.

Preventing, Improving and/or Treating Skin Conditions with the Extracts Derived from Sugar Cane The extracts derived from sugar cane and compositions comprising the extracts of the present disclosure can be used for preventing, improving or treating skin conditions. The skin conditions include, for example, atopic dermatitis, acne, eczema, psoriasis, dry skin, oily skin, pruritic skin, wrinkles, fine lines, dark spots, age spots, mottled pigmentation, skin pigmentation, melasma, darkened skin, redness, flushing, inflammation, skin elasticity, dark circles under the eyes, changes associated with skin aging, hair loss and wound healing.

For preventing, improving or treating many of these skin conditions, the extracts derived from sugar cane of the present disclosure provide their beneficial effects by: inhibiting or activating key enzymes in the skin; possessing a high antioxidant and anti-inflammatory activity; and inhibiting particular pathogenic bacteria.

For improving wound healing, the extracts derived from sugar cane of the present invention provide their beneficial effects by influencing one or more phases of the healing process. For example: reducing inflammation and thereby preventing scar tissue; by improving the healing time and appearance of the healed skin; by protecting the healing skin from oxidative damage; and by preventing or treating infection.

The present inventors have surprisingly found that the extracts derived from sugar cane of the present disclosure inhibit the collagen degrading enzymes, including for example collagenase and matrix metalloproteinase-1 (MMP-1), and the elastin degrading enzymes, including for example elastase. See Examples 11 and 16. Wrinkle formation in the skin is accompanied by a decrease in skin elasticity and the curling of elastic fibers (such as elastin) in the dermis. Elastase inhibitors suppress elastase activity (degradation of elastin) and prevent the damage of dermal elastin, thus helping mitigate wrinkle formation.

The collagen content of skin is the net balance between collagen synthesis and collagen breakdown. It is known that with age collagen synthesis in the skin is reduced. Additionally, environmental stress such as smoking, UV exposure, pollution and inflammation stimulate the production of collagen-degrading enzymes that causes collagen breakdown. Collagenase and MMP-1, two of the key collagen-degrading enzymes, are considered to be central to the causes of skin aging. Direct inhibition of these enzymes can be an effective approach to mitigate collagen breakdown in the skin thereby improving skin health, general condition and tone and reduction of wrinkles.

The colour of mammalian skin is determined by many factors, one of which is the production and distribution of melanin. Melanin is essential in protecting skin against UV radiation, but over production of melanin is also a major consequence of UV damage and the aging process that induces pigmentation disorders such as freckles and senile lentigo (i.e., age spots). Excessive melanin has also been viewed as a melanoma precursor. Melanin inhibition is a desirable effect sought in various fronts of cosmetic industry to achieve skin whitening, lessen aging appearance, and preventing melanoma.

The present inventors have also surprisingly found that the extracts derived from sugar cane of the present disclosure inhibit the tyrosinase enzyme. See Example 12. In the melanin biosynthesis process, tyrosinase is the key enzyme that catalyses the first step of melanogenesis. Previous studies have shown that melanin reduction and skin whitening and/or lightening can be achieved, at least partially, by deactivation of tyrosinase. Therefore, tyrosinase inhibitors have become increasingly important in cosmetic and medicinal products used in the prevention or reduction of hyperpigmentation, in skin whitening and/or lightening, to lessen the aging appearance and to prevent melanoma.

The extracts derived from sugar cane of the present disclosure also activate telomerase. See Example 15. Telomerase is an enzyme which builds telomeres, the regions of repetitive sequences at each end of chromosomes in most eukaryotes. Telomeres protect the end of the chromosome from DNA damage and become shortened through recursive cell division thereby causing cells to age. Telomerase can slow, stop or perhaps even reverse the telomere shortening that happens with age, however, the amount and activity of telomerase also declines with age. Activation of telomerase can reverse skin cell aging and revert the skin to a more youthful physical and genetic state.

The extracts derived from sugar cane of the present disclosure possess a high antioxidant capacity and may also provide their beneficial effects through this antioxidant activity. The extracts derived from sugar cane of the present disclosure demonstrated antioxidant activity against all six common free radicals (reactive oxygen species (ROS)), i.e., peroxyl radical, hydroxyl radical, superoxide anion, singlet oxygen, peroxynitrite, and hypochlorite, that are generated in cells and the body as a result of oxidative stress. Antioxidant activity against all the six common free radicals of an extract derived from sugar cane of the present disclosure is well demonstrated in Tables 32 and 33.

Furthermore, the present inventors have surprisingly found that extracts derived from sugar cane of the present disclosure stimulate the production of Nuclear factor (erythroid derived 2)-like 2 (Nrf2) in human cells. See Example 19. Nrf2 is a redox-sensitive transcription factor that binds to antioxidant response elements (ARE) to regulate the expression of antioxidant enzymes that protect against oxidative damage triggered by injury and inflammation. Activation of the Nrf2 pathway (both topical and internal/systemic) has been found to have a wide range of beneficial effects on skin, including reduced rates of skin cancers, protection from ultraviolet radiation, reduced inflammation, irritation and redness, reduction of wrinkles and improvement in skin tone, enhanced barrier function, and improved wound healing.

The extracts derived from sugar cane of the present disclosure also inhibit Nuclear Factor κB (NF-κB), a protein complex that is involved in cellular responses to stimuli such as stress and free radicals, ultraviolet irradiation, oxidized LDL, and bacterial or viral antigens. See Example 20. It has been associated with inflammation and plays a major role in the aging process of the skin. Reducing or inhibiting inflammation improves skin tone, appearance, reduces swelling, improves healing time and can decrease the formation of scar tissue in wound healing.

The present inventors have also surprisingly found that extracts derived from sugar cane of the present disclosure inhibit Tumor Necrosis Factor (TNF)-α. See Example 21. TNF-α is a pro-inflammatory cytokine that triggers downstream cellular feedback loops governing inflammation. TNF-α has been identified as an inflammation trigger and precursor. Reducing or inhibiting inflammation improves skin tone, appearance, reduces swelling, improves healing time and can decrease the formation of scar tissue in wound healing.

The extracts derived from sugar cane of the present disclosure also inhibit prostaglandin E2 synthesis. See Example 22. $PGE_2$ is the major prostaglandin produced by cyclooxygenase enzymes in the skin and is a potentiator of acute inflammation. Thus, inhibiting $PGE_2$ reduces or inhibits inflammation, leading to improved skin tone, appearance, reduced swelling, improved healing time and decreased formation of scar tissue.

The extracts derived from sugar cane of the present disclosure inhibit Cyclooxygenases-2 (COX-2). See Example 23. COX-2 catalyzes the conversion of arachidonic acid to prostaglandin (PG) $H_2$, the precursor of PGs and thromboxane and plays an important role in inflammation and pain. Hence, COX-2 inhibition can reduce symptoms of inflammation. The reduction or inhibition of inflammation improves skin tone, appearance, reduces swelling, improves healing time and can decrease the formation of scar tissue in wound healing.

The extracts derived from sugar cane of the present disclosure also inhibit the growth of pathogenic bacteria which can cause topical skin infections and acne. See Example 24. Examples of pathogenic bacteria include, but are not limited to, *Stapholococcus aureus, Staphylococcus epidermidis, Propionibacterium acnes* and *Escherichia coli*. The antibacterial properties of the extracts of the present disclosure also aids in the treatment of wounds by preventing or treating infection, which can delay the healing process.

In one embodiment, the extracts derived from sugar cane of the present disclosure can be used in methods for preventing skin conditions. In one embodiment, the extracts derived from sugar cane of the present disclosure can be used in methods for improving skin conditions. In one embodiment, the extracts derived from sugar cane of the present disclosure can be used in methods for treating skin conditions.

In one aspect of the disclosure there is provided a method for preventing, improving or treating a skin condition in a subject, the method comprising administering an effective amount of an extract derived from sugar cane comprising polyphenols of the present disclosure. In one embodiment, there is provided a method for preventing, improving or treating a skin condition in a subject in need thereof, the method comprising administering an effective amount of an extract derived from sugar cane to the subject, the extract comprising from about 10 catechin equivalent (CE) g/L to about 50 CE g/L of polyphenols or from about 100 CE mg/g to about 500 CE mg/g of polyphenols.

In another aspect of the disclosure there is provided an extract derived from sugar cane comprising polyphenols of the present disclosure for use in preventing, improving or treating a skin condition in a subject. In one embodiment, there is provided an extract derived from sugar cane for use in preventing, improving or treating a skin condition in a subject, the extract comprising from about 10 catechin equivalent (CE) g/L to about 50 CE g/L of polyphenols or from about 100 CE mg/g to about 500 CE mg/g of polyphenols.

In another aspect of the disclosure there is provided the use of an extract derived from sugar cane comprising polyphenols of the present disclosure in the manufacture of a medicament for preventing, improving or treating a skin condition. In one embodiment, there is provided the use of an extract derived from sugar cane in the manufacture of a medicament for preventing, improving or treating a skin condition, the extract comprising from about 10 catechin equivalent (CE) g/L to about 50 CE g/L of polyphenols or from about 100 CE mg/g to about 500 CE mg/g of polyphenols.

As would be understood by those skilled in the art, the methods and uses described herein may be for therapeutic or cosmetic benefits. In one embodiment, the methods and uses are therapeutic. Therapeutic methods and uses relate to the prevention, improvement or treatment of a skin disease or disorder as well as the alleviation of the symptoms of pain and suffering of the skin disease or disorder.

In one embodiment, there is provided a therapeutic method for preventing, improving or treating a skin condition in a subject, the method comprising administering a therapeutically effective amount of an extract derived from sugar cane comprising polyphenols of the present disclosure.

In another embodiment, the methods and uses are cosmetic. Cosmetic methods and uses are designed to beautify the skin, improve the appearance of the skin and generally improve the aesthetics of the skin. In one embodiment, there is provided a cosmetic method for preventing, improving or treating a skin condition in a subject, the method comprising administering an effective amount of an extract derived from sugar cane comprising polyphenols of the present disclosure.

The extracts derived from sugar cane comprising polyphenols of the present disclosure may be used in the prevention, improvement or treatment of any relevant skin condition. The skin condition may be selected from the group including, for example, atopic dermatitis, acne, eczema, psoriasis, dry skin, oily skin, pruritic skin, wrinkles, fine lines, dark spots, age spots, mottled pigmentation, skin pigmentation, melasma, darkened skin, redness, flushing, inflammation, skin elasticity, dark circles under the eyes, changes associated with skin aging, hair loss and wound healing.

In one embodiment, the skin condition is atopic dermatitis. In one embodiment, the skin condition is acne. In one embodiment, the skin condition is eczema. In one embodiment, the skin condition is psoriasis. Psoriasis is a chronic autoimmune disease characterized by patches of red, itchy and scaly skin, which can be painful.

In one embodiment, the skin condition is dry skin. In one embodiment, the skin condition is oily skin. In one embodiment, the skin condition is pruritic skin. In one embodiment, the skin condition is wrinkles. In one embodiment, the skin condition is fine lines. In one embodiment, the skin condition is dark spots. In one embodiment, the skin condition is age spots. In one embodiment, the skin condition is mottled pigmentation. In one embodiment, the skin condition is skin pigmentation. In one embodiment, the skin condition is melasma. In one embodiment, the skin condition is darkened skin. In one embodiment, the skin condition is redness. In one embodiment, the skin condition is flushing. In one embodiment, the skin condition is inflammation. In one embodiment, the skin condition is skin elasticity. In one embodiment, the skin condition is dark circles under the eyes. In one embodiment, the skin condition is changes associated with skin aging.

In one embodiment, the skin condition is selected from dry skin, oily skin, pruritic skin, wrinkles, fine lines, dark spots, age spots, mottled pigmentation, skin pigmentation, melasma, darkened skin, redness, flushing, inflammation, skin elasticity, dark circles under the eyes and changes associated with skin aging. In another embodiment the skin condition is wrinkles, fine lines, dark spots, age spots, mottled pigmentation, skin pigmentation, melasma, darkened skin, skin elasticity, dark circles under the eyes and changes associated with skin aging.

The prevention, improvement or treatment of the skin condition may provide one or multiple benefits. The prevention, improvement or treatment of the skin condition may provide benefits, including for example, skin moisturisation, skin exfoliation, skin lightening or colour reduction, skin pigmentation reduction, skin redness reduction, skin flushing reduction, inflammation reduction, fine line reduction, wrinkle reduction, wrinkle depth reduction, flakiness reduction, itchiness reduction, skin dryness reduction, skin roughness reduction, enhanced skin radiance, enhanced skin tone, enhanced skin clarity, enhanced skin firmness, enhanced skin tightness, enhanced skin elasticity, enhanced aesthetic appearance of the skin and/or enhanced overall skin appearance.

In one embodiment, the prevention, improvement or treatment of the skin condition provides skin moisturisation. In one embodiment, the prevention, improvement or treatment of the skin condition provides skin exfoliation. In one embodiment, the prevention, improvement or treatment of the skin condition provides skin lightening or colour reduction. In one embodiment, the prevention, improvement or treatment of the skin condition provides skin pigmentation reduction. In one embodiment, the prevention, improvement or treatment of the skin condition provides skin redness reduction. In one embodiment, the prevention, improvement or treatment of the skin condition provides skin flushing reduction. In one embodiment, the prevention, improvement or treatment of the skin condition provides inflammation reduction. In one embodiment, the prevention, improvement or treatment of the skin condition provides fine line reduction. In one embodiment, the prevention, improvement or treatment of the skin condition provides wrinkle reduction. In one embodiment, the prevention, improvement or treatment of the skin condition provides wrinkle depth reduction. In one embodiment, the prevention, improvement or treatment of the skin condition provides flakiness reduction. In one embodiment, the prevention, improvement or treatment of the skin condition provides itchiness reduction. In one embodiment, the prevention, improvement or treatment of the skin condition provides skin dryness reduction. In one embodiment, the prevention, improvement or treatment of the skin condition provides skin roughness reduction. In one embodiment, the prevention, improvement or treatment of the skin condition provides enhanced skin radiance. In one embodiment, the prevention, improvement or treatment of the skin condition provides enhanced skin tone. In one embodiment, the prevention, improvement or treatment of the skin condition provides enhanced skin clarity. In one embodiment, the prevention, improvement or treatment of the skin condition provides enhanced skin firmness. In one embodiment, the prevention, improvement or treatment of the skin condition provides enhanced skin tightness. In one embodiment, the prevention, improvement or treatment of the skin condition provides enhanced skin elasticity. In one embodiment, the prevention, improvement or treatment of the skin condition provides enhanced aesthetic appearance of the skin. In one embodiment, the prevention, improvement or treatment of the skin condition provides enhanced overall skin appearance.

In one embodiment, the skin condition is a hair loss condition and the extracts derived from sugar cane comprising polyphenols of the present disclosure may be used in the prevention, improvement or treatment of a hair loss condition. The hair loss condition may be selected from the group including, for example, male-pattern hair loss, female-pattern hair loss, alopecia areata, and a thinning of hair known as telogen effluvium. A hair loss condition includes that commonly referred to as 'balding', 'baldness' and 'hair thinning'.

Hair follicle growth occurs in cycles. Each cycle consists of a long growing phase (anagen), a short transitional phase (catagen) and a short resting phase (telogen). At the end of the resting phase, the hair falls out (exogen) and a new hair starts growing in the follicle beginning the cycle again. Hair is naturally lost during the 'resting' telogen phase. Problems occur and hair loss becomes visible when there are too many resting hair follicles. The longer they remain resting, the greater the chance of permanent hair loss. Without wishing to be bound by theory, the extracts derived from sugar cane comprising polyphenols of the present disclosure activate resting hair follicles ('follicular activation') and can therefore be used to prevent, improve or treat hair-loss conditions.

In one embodiment, the hair loss condition is balding. In one embodiment, the hair loss condition is baldness. In one embodiment, the hair loss condition is hair thinning. In one embodiment, the hair loss condition is male-pattern hair loss. In one embodiment, the hair loss condition is female-pattern hair loss. In one embodiment, the hair loss condition is alopecia areata. In one embodiment, the hair loss condition is telogen effluvium.

In one embodiment, the skin condition is wound healing and the extracts derived from sugar cane of the present disclosure may be used in the improvement or treatment of wound healing. Skin wounds can include trauma, burns, abrasions, lacerations, ulcerations, skin cancers, infection or underlying medical conditions such as diabetes and wounds from surgical procedures.

Wound healing is a natural restorative response to tissue injury which generates resurfacing, reconstitution, and restoration of the tensile strength of injured skin. The wound healing stages are made up of three basic phases—the inflammatory phase which consists of the establishment of homeostasis, and inflammation; the proliferative phase, which consists of granulation, contraction and epithelialisation and the remodelling phase, which eventually determines the strength and appearance of the healed skin. The symptoms of inflammation include heat, redness, swelling and pain. Whilst inflammation is involved in the first stage of the wound healing process, if it persists for too long, inflammation can delay recovery and may result in increased scar tissues.

Without wishing to be bound by theory, the extracts derived from sugar cane of the present disclosure provide their beneficial effects by influencing one or more phases of the healing process such as by reducing inflammation and thereby preventing scar tissue. In addition, the high antioxidant activity of the extracts of the present disclosure play a significant role in the process of wound healing by improving the healing time and appearance of the healed skin and by protecting the healing skin from oxidative damage. Further, the extracts of the present disclosure have antibacterial properties which aid in the prevention or treatment of the wound from infection, which can delay the healing process.

In one embodiment, the improvement or treatment of wound healing provides reduced inflammation. In one embodiment, the improvement or treatment of wound healing provides decreased formation of scar tissue. In one embodiment, the improvement or treatment of wound healing provides improved healing time. In one embodiment, the improvement or treatment of wound healing provides improved appearance of the healed skin. In one embodiment, the improvement or treatment of wound healing provides protection of the healing skin from oxidative damage. In one embodiment, the improvement or treatment of wound healing provides prevention or treatment of the wound from infection.

In the methods and uses of the present disclosure, the extracts derived from sugar cane may be administered orally, topically or by injection. In the methods or uses of the present disclosure, the extracts may be administered in the form of a composition as described herein and/or as known by one of ordinary skill in the art.

The frequency of administration of the extract derived from sugar cane or a composition comprising the extract derived from sugar cane, may be as required to provide the desired prevention, improvement or treatment of the skin condition. As would be understood by one of ordinary skill in the art, the frequency of administration of the extract derived from sugar cane or a composition comprising the extract derived from sugar cane, may depend on the amount or dosage of the extract. A higher amount or dosage of the extract derived from sugar cane may result in less frequent administration being required. A lower amount or dosage of the extract derived from sugar cane may result in more frequent administration being required. The administration of the extract derived from sugar cane or a composition comprising the extract derived from sugar cane, may be for a short period or for an extended or continuous period, depending on the skin condition.

The frequency of administration may be daily, twice daily, thrice daily, every 1-3 days, every 1-5 days, weekly, fortnightly, monthly, bi-monthly, every 1-3 months, every 1-6 months, every 6 months, or yearly. In one embodiment, the frequency of administration is daily. In one embodiment, the frequency of administration is twice daily. In one embodiment, the frequency of administration is weekly. In one embodiment, the frequency of administration is fortnightly. In one embodiment, the frequency of administration is monthly. In one embodiment, the frequency of administration is bi-monthly. In one embodiment, the frequency of administration is every 1-3 months. In one embodiment, the frequency of administration is every 1-6 months. In one embodiment, the frequency of administration is every 6 months. In one embodiment, the frequency of administration is yearly.

The methods and uses may be useful for any mammal with a skin condition. The mammal may, for example, be primates, such as humans, cows, sheep, goats, horses, dogs, cats, guinea pigs, rats or other bovine, ovine, equine, canine, feline, rodent or murine species. In one embodiment, the mammal is human.

As would be understood by one of ordinary skill in the art, the skin may be any skin or part thereof of a subject. For example, but not limited to, the skin may be the skin on the face, neck, hands, chest, arms, legs, shoulders, back and feet. In one embodiment, the skin is on the face, neck, hands and/or. In one embodiment, the skin is on the face. In one embodiment, the skin is on the neck. In one embodiment, the skin is on the hands. In one embodiment, the skin is on the back.

EXAMPLES

Example 1 provides illustrative and non-limiting examples of characterisation of the extracts derived from sugar cane of the present disclosure.

Example 1. Characterisation of Extracts Derived from Sugar Cane

In order to characterise the types and quantity of polyphenols in extracts derived from sugar cane, some extracts were analysed by Liquid Chromatography-Mass Spectrometry (LCMS) and by NMR spectroscopy.

The three samples A, B, and C were fractions from molasses (FIG. 1). All the samples were stored at −20° C.

TABLE 1

Extract fractions from molasses

| Code | Sample Name | Description |
|---|---|---|
| A | FPX66 bound fraction | Brown syrup |
| B | FPX66 unbound fraction | Light yellow syrup |
| C | 74 Brix | Dark brown syrup |

One mL of each of the samples were transferred into pre-weighed vials in duplicate and then freeze-dried for 3 days to obtain dry mass (Table 2). One replicate of each of the samples was analysed by NMR spectroscopy and the other replicate of each of the samples was used for quantitative analysis of polyphenols by LCMS.

TABLE 2

Moisture content of samples

| Sample | Replicate | Wt. of 1.0 mL, g | Loss in wt., g | Wt. of dried extract, g | % Moisture | Analysis |
|---|---|---|---|---|---|---|
| A: Bound Fraction | a | 1.0568 | 0.8471 | 0.2097 | 80.16 | NMR |
|  | b | 1.0683 | 0.8559 | 0.2124 | 80.12 | LCMS |
| B: Unbound Fraction | a | 1.1324 | 0.7761 | 0.3563 | 68.54 | NMR |
|  | b | 1.1288 | 0.7730 | 0.3558 | 68.48 | LCMS |
| C: 74 Brix Fraction | a | 1.0300 | 0.2491 | 0.7809 | 24.18 | NMR |
|  | b | 1.1690 | 0.2751 | 0.8939 | 23.53 | LCMS |

The 74 Brix sample was fractionated by C18 solid phase extraction (SPE) to remove the sugars and obtain more concentrated phenolic components. One mL was diluted in Milli-Q water and eluted through a Waters 3 mL SPE Vac C18 cartridge that was initially activated with MeOH and then conditioned with Milli-Q water. The polar components were eluted with 6 mL Milli-Q water which was discarded. The remaining metabolites on the SPE cartridge were then eluted with 2×3 mL MeOH into a pre-weighed vial and the solvent was evaporated to dryness under nitrogen gas. The 74 Brix SPE-MeOH fraction was further dried overnight in the freeze dryer and then weighed to obtain the dry weight of fraction (55.6 mg). The extract was reconstituted in 200 µl 80:20 MeOH—$H_2O$ (concentration=278 mg/mL) and analysed on the LCMS.

Reference Standards

Table 3 lists the reference standards used for the qualitative analysis of phenolic compounds by LCMS. Standard solutions were prepared either in MeOH or 1:1 MeOH—$H_2O$. Fourteen of the standards were used for quantitative analysis of phenolic compounds by LCMS and a range concentrations was prepared from stock solutions indicated in Table 3 using 80:20 MeOH—$H_2O$ as diluent.

TABLE 3

List of reference standards used for LCMS analysis

| Code | Compound | Molecular Formula | Molecular Wt., g/mol | Stock Concentration, µg/mL |
|---|---|---|---|---|
| S01 | Syringic acid | $C_9H_{10}O_5$ | 198.17 | 6,000 |
| S02 | Caffeic acid | $C_9H_8O_4$ | 180.16 | 600 |
| S03 | Vanillin | $C_8H_8O_3$ | 152.15 | 60 |
| S4 | Sinapic acid | $C_{11}H_{12}O_5$ | 224.21 | 115 |
| S5 | Tricin | $C_{17}H_{14}O_7$ | 330.29 | 100 |
| S6 | Chlorogenic acid | $C_{16}H_{18}O_9$ | 354.31 | 1,900 |
| S7 | Diosmin | $C_{28}H_{32}O_{15}$ | 608.54 | 1,000 |
| S8 | Diosmetin | $C_{16}H_{12}O_6$ | 300.26 | 100 |
| S9 | Apigenin | $C_{15}H_{10}O_5$ | 270.24 | 10 |
| S10 | Vitexin | $C_{21}H_{20}O_{10}$ | 432.38 | 100 |
| S11 | Orientin | $C_{21}H_{20}O_{11}$ | 448.38 | 90 |
| S12 | Homoorientin | $C_{21}H_{20}O_{11}$ | 448.38 | 40 |
| S13 | Swertisin | $C_{22}H_{22}O_{10}$ | 446.40 | 21 |
| S14 | Myricetin | $C_{15}H_{10}O_8$ | 318.24 | 400 |

Nuclear Magnetic Resonance (NMR) Spectroscopy

Approximately 1 g of the samples were freeze dried and the dried residue was taken up in at least 1 mL of $D_2O$ (Cambridge Isotopes) with 2 mM of 3-(trimethylsilyl)propionic-2,2,3,3-$d_4$ acid sodium salt (TSP, Sigma Aldrich 269913) and 0.5% sodium azide ($NAN_3$). Six hundred µL of each sample was transferred into 5 mm NMR tubes and analysed. $^1H$ (700.13 MHz) and $^{13}C$ NMR (176.07 MHz) spectra were acquired using a Bruker Avance III NMR spectrometer with cryoprobe and TopSpin v3.2 software.

Qualitative Analysis by Liquid Chromatography-Mass Spectroscopy (LCMS)

Figure 3:
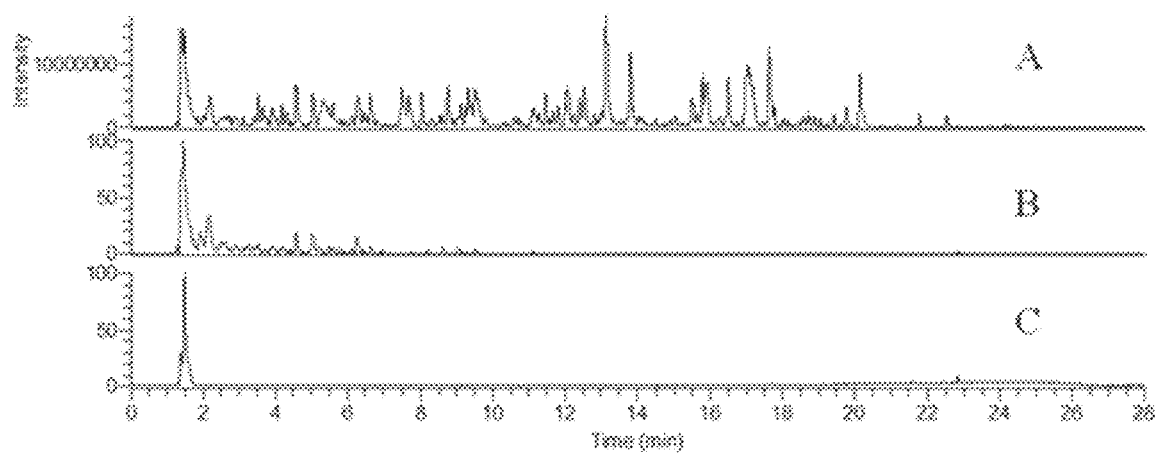
FIG. 3 exhibits base peak chromatograms (FTMS negative) of three extracts from molasses obtained by the process of FIG. 1 and analysed by LCMS. A) resin bound sample, B) resin unbound sample, and C) 74 Brix sample.

The samples were analysed by LCMS. The negative MS data was analysed using Genedata software and after pre-processing (RT restriction to exclude sugars, noise removal, cluster identification, etc.). 4,250 features were identified across all samples. There were 4,196 features identified in sample A (FPX66 bound fraction), 1,127 in sample B (FPX66 unbound fraction), and 178 in C (74 Brix sample) (FIG. 3).

A number of phenolic compounds were identified in the extracts by comparison to the 42 standards analysed: vanillin, apigenin, orientin, vitexin, caffeic acid, chlorogenic acid, syringic acid, diosmin, swertisin, homoorientin, diosmetin, sinapic acid (trace amount), myricetin (trace amount), tricin (trace amount).

Table 4 exhibits polyphenol amounts in extracts derived from sugar cane from LCMS analysis in μg/gram dry weight basis.

TABLE 4

Polyphenol amounts in exemplary extracts derived from sugar cane of the present disclosure

| Polyphenol | 74 Brix sample (C) in μg/g | FPX66 bound sample (A) in μg/g |
|---|---|---|
| Syringic Acid | 10.9 | 107.57 |
| Caffeic Acid | 0.29 | 7.54 |
| Vanillin | 0.153 | 2.13 |
| Sinapic Acid | 0.18 | 1.73 |
| Tricin | 0.03 | 0.4 |
| Chlorogenic Acid | 6.53 | 74.29 |
| Diosmin | 19.45 | 227 |
| Diosmetin | 0.15 | 0.16 |
| Apigenin | 0.001 | 0.01 |
| Vitexin | 0.084 | 1.62 |
| Orientin | 0.245 | 4.5 |
| Homoorientin | 0.041 | 0.58 |
| Swertisin | 0.69 | 5.25 |

Qualitative Analysis by Nuclear Magnetic Resonance (NMR) Spectroscopy

Figure 4:
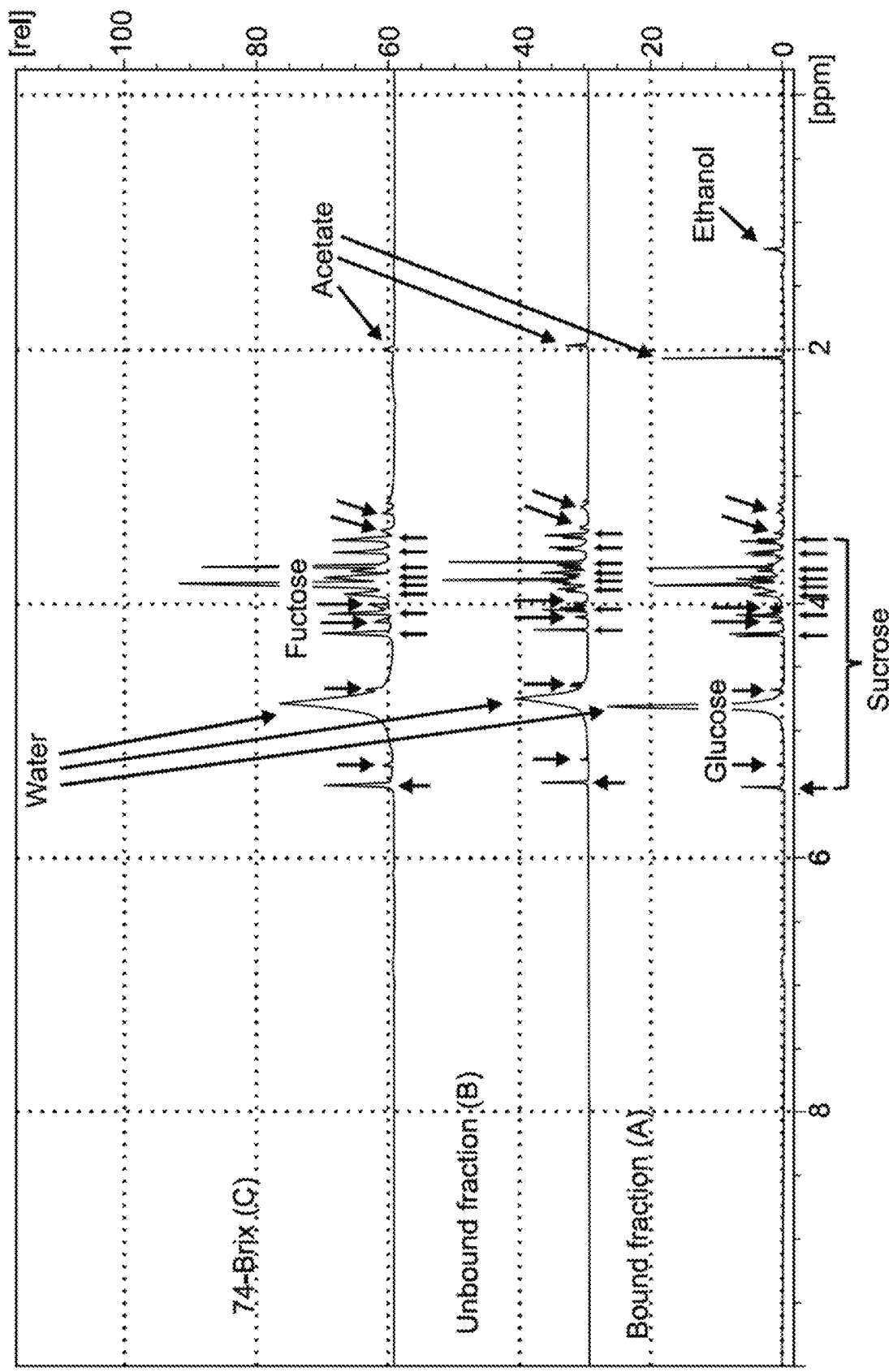
FIG. 4 exhibits $^1$H NMR spectrum of three extracts from molasses obtained by the process of FIG. 1 in $D_2O$ with TSP (at 0.00 ppm) as reference. A) resin bound sample, B) resin unbound sample, and C) 74 Brix sample. Arrows indicate associated peak signals to specific sugars: nine arrows pointing up—sucrose; two arrows pointing down and two arrows pointing diagonally down—glucose; two arrows pointing down in the middle—fructose.
Figure 5B:
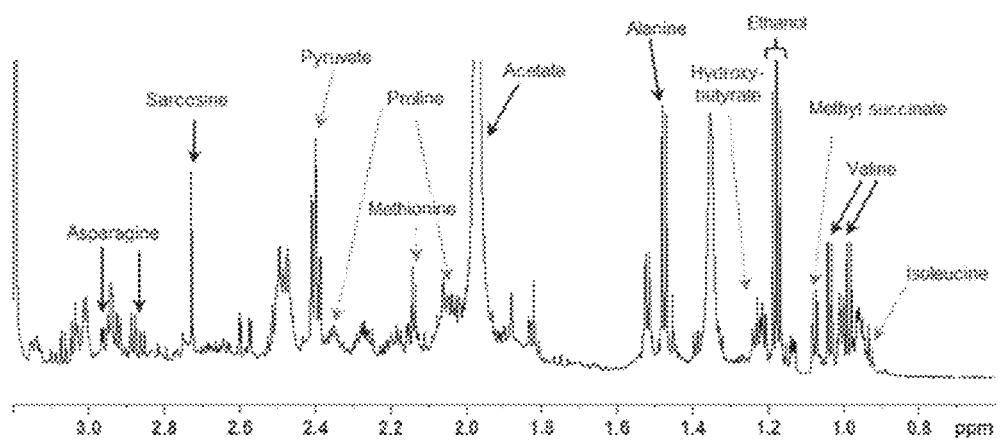
FIGS. 5A and 5B exhibit expanded 0.6-3.2 ppm region of the $^1$H NMR spectrum of the resin unbound (FIG. 5B) and resin bound (FIG. 5A) extracts obtained by the process of FIG. 1 in $D_2O$ with TSP as reference.
Figure 5A:
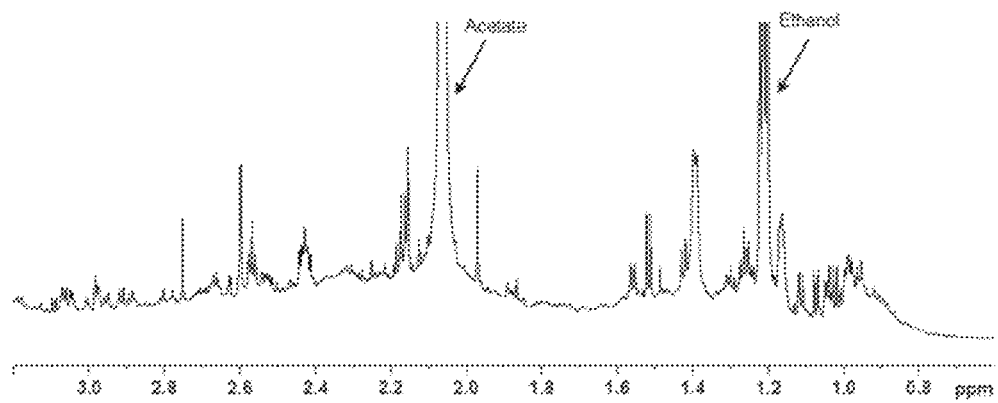

All the samples showed the dominant presence of sucrose and glucose with fructose present in lower amounts (FIG. 4). The samples A, B and C showed well resolved peaks in the 3-5 ppm region where the sugar signals are expected.

Metabolites such as organic acids and amino acids were identified through database comparison in Chenomx™ and the Human Metabolome Database (www.hmdb.ca). These metabolites were in either or both the bound and unbound fractions (FIGS. 5A, 5B, 6A and 6B).

Figure 6B:
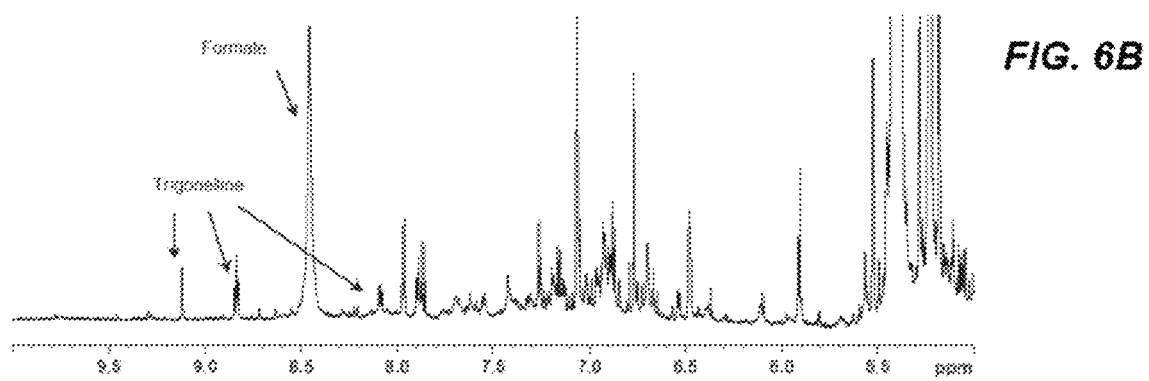
FIGS. 6A and 6B exhibit expanded 5.0-10.0 ppm region of the $^1$H NMR spectrum of the resin unbound (FIG. 6B) and resin bound (FIG. 6A) extracts obtained by the process of FIG. 1 in $D_2O$ with TSP as reference.
Figure 6A:
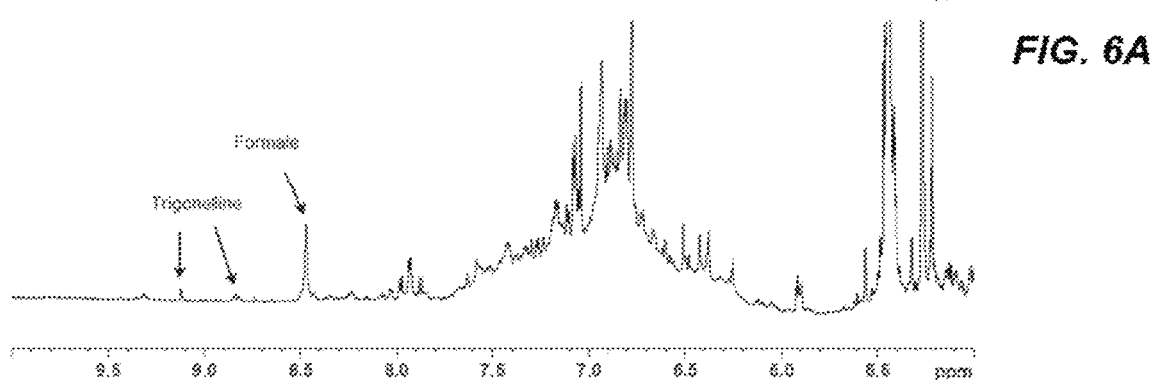

Organic acids identified were acetate, pyruvate, and formate; and amino acids identified were isoleucine, valine, methyl succinate, hydroxybutyrate, alanine, proline, methionine, sarcosine, asparagine. Trigonelline, which is an alkaloid typically present in coffee was also identified (FIGS. 6A and 6B).

Amino acids identified were isoleucine, valine, methyl succinate, hydroxybutyrate, alanine, proline, methionine, sarcosine, asparagine.

Total amino acids, free amino acids, essential amino acids and leucine, minerals of the extract were measured by using standard technique.

Table 5 exhibits mineral concentration of an extract derived from sugar cane of the present disclosure in mg/Kg dry weight basis. The concentration of selenium and chromium is shown in μg/kg dry weight basis.

Analysis by Gas Chromatography-Mass Spectroscopy (GC-MS)

In order to characterise the types of compounds in extracts derived from sugar cane molasses, extracts A, B and D were additionally analysed by Gas Chromatography-Mass Spectrometry (GC-MS). The three extracts A, B, and D were fractions from molasses (FIGS. 1 and 2).

Polar Metabolite Derivatization

All samples were dissolved in 10 μL of 30 mg/mL methoxyamine hydrochloride in pyridine and derivatized at 37° C. for 120 minutes with mixing at 500 rpm. The samples were incubated for 30 minutes with mixing at 500 rpm after addition of both 20 μL N,O-bis-(trimethylsilyl)trifluoroacetamide (BSTFA) and 1 μL retention time standard mixture [0.029% (v/v) n-dodecane, n-pentadecane, n-nonadecane, n-docosane, n-octacosane, n-dotriacontane, n-hexatriacontane dissolved in pyridine]. Each derivatized sample was allowed to rest for 60 min prior to injection.

GC-MS Instrument Conditions

Samples (1 μL) were then injected into a GC-MS system in split (1:20 split ratio) or splitless mode, comprised of a Gerstel PAL3 Autosampler, a 7890B Agilent gas chromatograph and a 5977B Agilent quadrupole MS (Agilent, Santa Clara, USA). The Mass Spectrometer was adjusted according to the manufacturer's recommendations using tris-(perfluorobutyl)-amine (CF43). A J&W Scientific VF-5MS column (30 m long with 10 m guard column, 0.25 mm inner diameter, 0.25 μm film thickness) was used. The injection temperature was set at 250° C.; the Mass Spectrometer transfer line at 290° C., the ion source adjusted to 250° C. and the quadrupole at 150° C. Helium (UHP 5.0) was used as the carrier gas at a flow rate of 1.0 mL/minute. The following temperature program was used; injection at 70° C., hold for 1 minute, followed by a 7° C./minute oven temperature, ramp to 325° C. and a final 6 minute heating at 325° C. Mass spectra were recorded at 2 scans/s with an 50-600 m/z scanning range.

Data Processing and Statistical Analysis

Both chromatograms and mass spectra were processed using the Agilent MassHunter Workstation Software, Quantitative Analysis, Version B.07.01/Build 7.1.524.0. Mass spectra of eluting compounds were identified using the commercial mass spectra library NIST 08 (http://www.nist.gov), the public domain mass spectra library of Max-Planck-Institute for Plant Physiology, Golm, Germany (http://csbdb.mpimp-golm.mpg.de/csbdb/dbma/msri.html) and the in-house mass spectral library. All matching mass spectra were additionally verified by determination of the retention time by analysis of authentic standard substances.

TABLE 5

Mineral composition of extracts derived from sugar cane of the present disclosure

| Anions | 74 Brix Sample (C) | FPX66 bound sample (A) | FPX66 bound sample (A) |
|---|---|---|---|
| Potassium | 26,000 mg/kg | 100-250 mg/kg | 190 mg/kg |
| Sodium | 450 mg/kg | 10-50 mg/kg | 30 mg/kg |
| Calcium | 1,090 mg/kg | 8,000-9,000 mg/kg | 8,800 mg/kg |
| Magnesium | 4,700 mg/kg | 1,500-2,500 mg/kg | 2,000 mg/kg |
| Iron | 65 mg/kg | 800-1000 mg/kg | 890 mg/kg |
| Zinc | 6.6 mg/kg | Not detected | Not detected |
| Selenium (μg/kg) | 786 μg/kg | Not detected | Not detected |
| Chromium (μg/kg) | 1,300 μg/kg | Not detected | Not detected |

If a specific metabolite had multiple TMS derivatives, the metabolite with the greater detector response and better peak shape within the dynamic range of the instrument was selected.

Figure 7A:
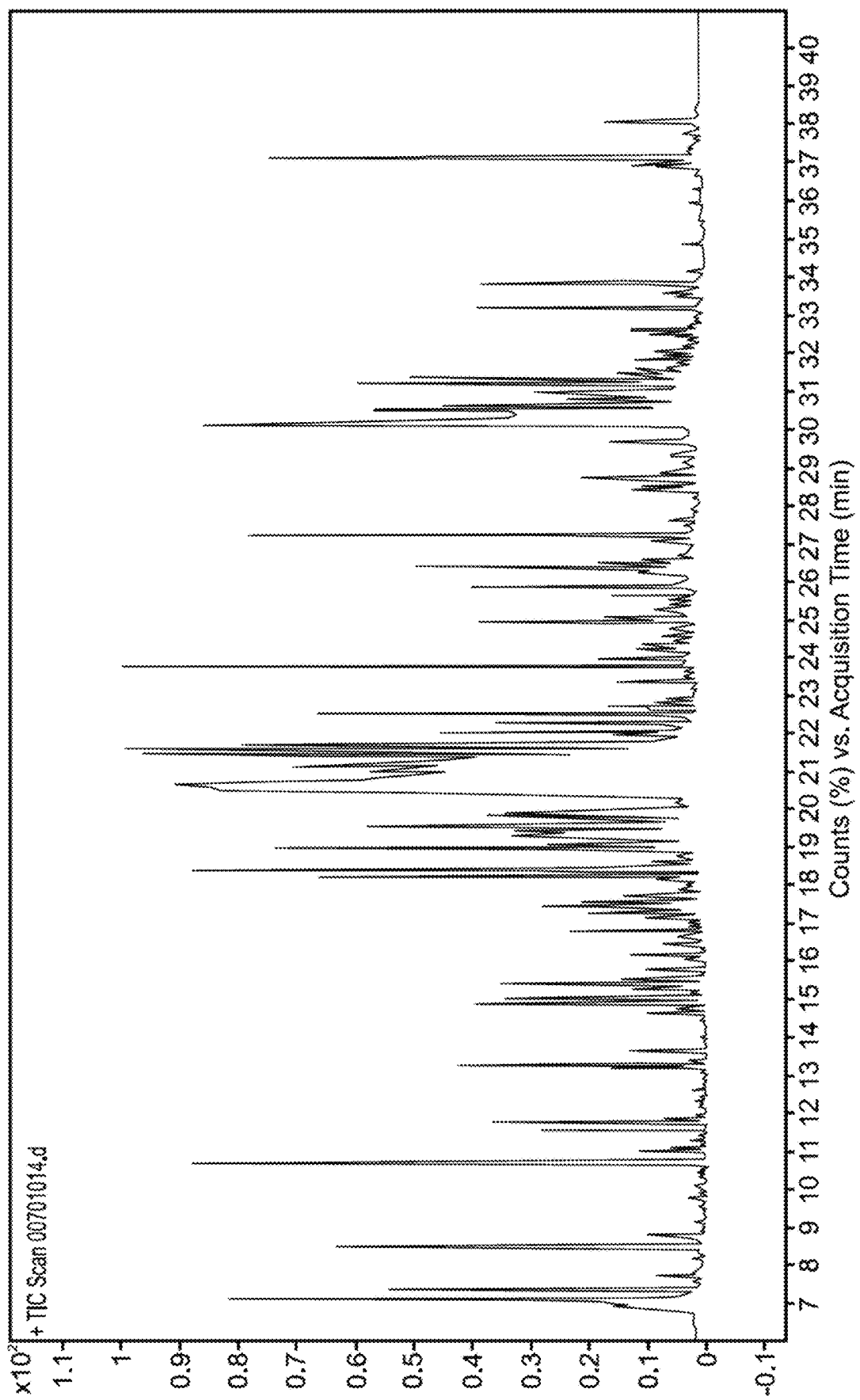
FIGS. 7A, 7B and 7C exhibit the spectra of three extracts from molasses analysed by GC-MS. A) resin unbound sample (Extract B) prepared according to the process in FIG. 1, B) resin bound sample (Extract A) prepared according to the process in FIG. 1, and C) resin bound sample (Extract D) prepared according to the process in FIG. 2.
Figure 7B:
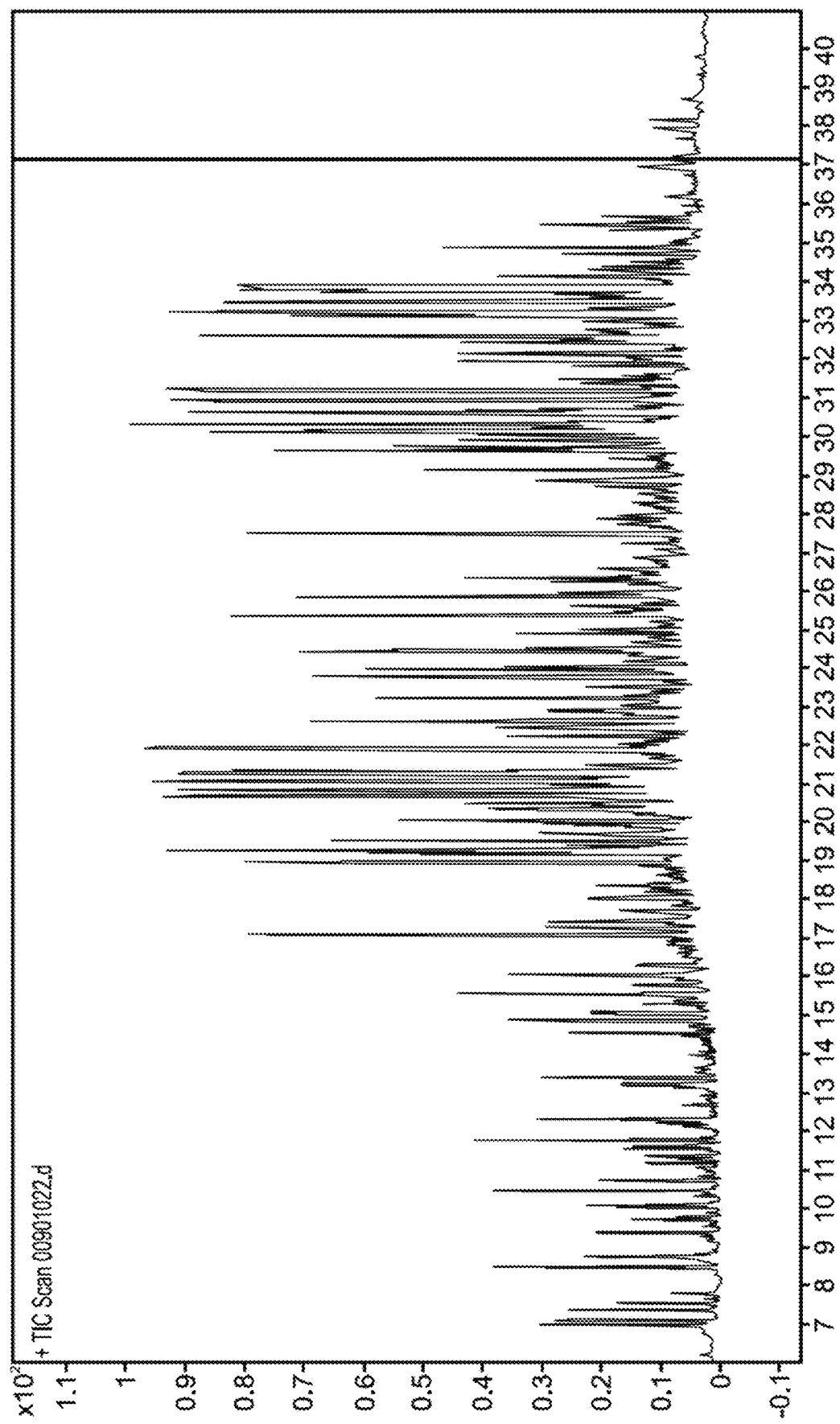
Figure 7C:
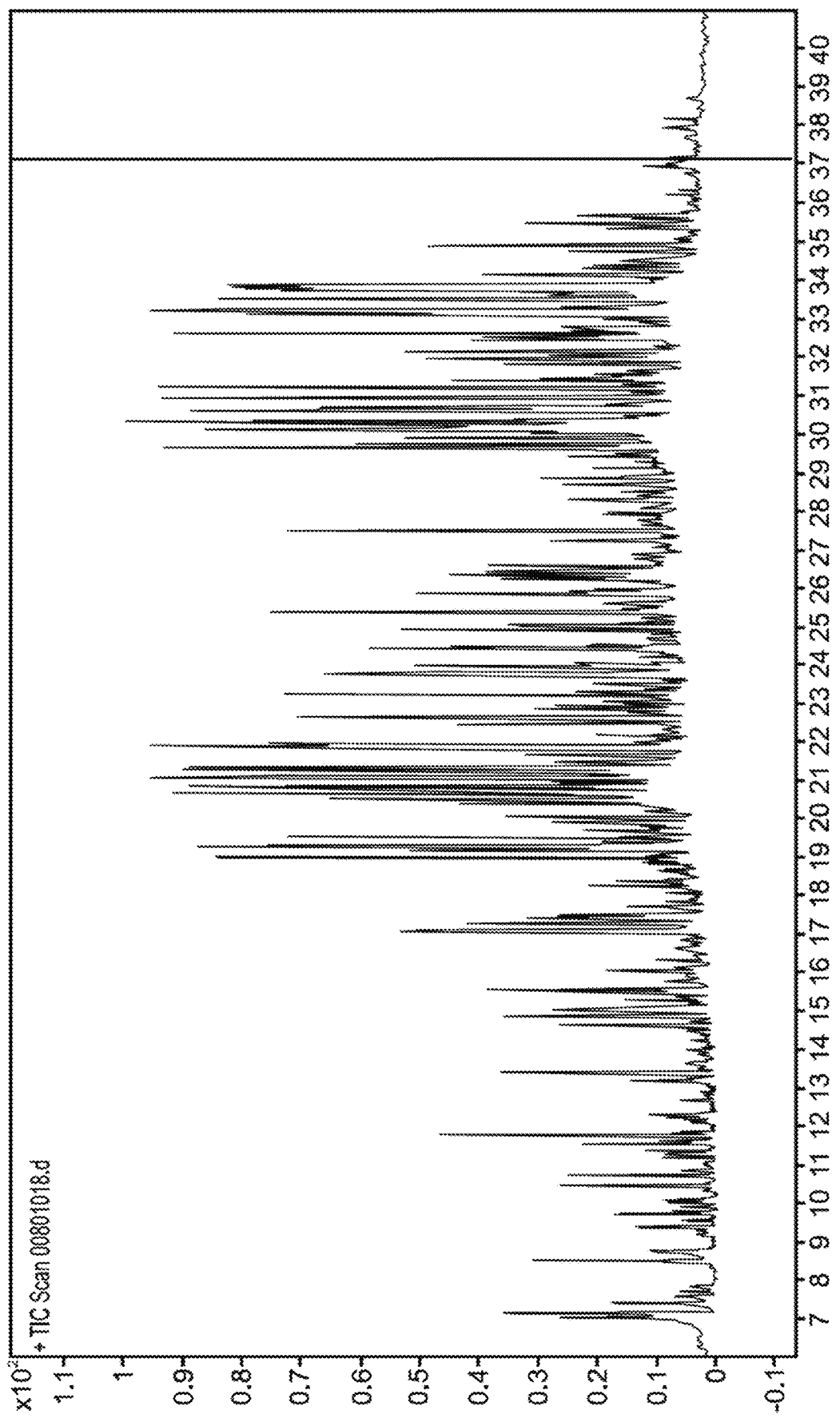

The results of the GC-MS analysis (Tables 6-9) confirmed the LCMS study and many additional compounds were detected. Each sample contained more than 100 different identified compounds. These mainly included a diverse range of acids, polyphenols, sugars and phytosterols, many of which have well characterised beneficial effects on health. For example, potential active ingredients for anti-acne and psoriasis were identified including azelaic acid, salicylic acid, gycolic acid. Arbutin, an antioxidant, which inhibits tyrosinase, and is known to be skin-whitening agent was also identified. Of the compounds identified, 19 compounds were found to be specific to Extract B. The GC-MS traces of the extracts are shown in FIGS. 7A, 7B and 7C.

TABLE 6

Identified peaks and retention times of Extract A

| Compound | Retention Time |
| --- | --- |
| CONT: 1038.1 | 6.252 |
| Pyruvic Acid (1TMS) | 7.00900 |
| Lactic Acid (2TMS) | 7.12300 |
| Glycolic Acid | 7.38700 |
| Oxalic Acid (2TMS) | 7.56100 |
| CONT 1228 | 8.17000 |
| 3-Hydroxypropanoic acid | 8.49900 |
| 3-hydroxy-pyridine (1TMS) | 8.52000 |
| CONT: 1228 | 8.76250 |
| n-Heptanoic acid (1TMS) | 9.38600 |
| Malonic Acid (2TMS) | 9.54500 |
| Benzoic acid (1TMS) | 10.4667 |
| DL-Serine (2TMS) | 10.523 |
| Phosphoric acid (3TMS) | 10.686 |
| Succinic Acid (2TMS) | 11.553 |
| DL-Glyceric Acid (3TMS) | 11.772 |
| Uracil (2TMS) | 11.997 |
| Fumaric Acid (2TMS) | 12.222 |
| n-Nonanoic acid (1TMS) | 12.432 |
| Thymine (2TMS) | 13.12 |
| DL-Aspartic acid (2TMS) | 13.562 |
| DL-Malic Acid (3TMS) | 14.622 |
| DL-Lactic Acid Dimer (2TMS) | 14.861 |
| 2,4-dihydroxy Butanoic Acid (3TMS) | 13.256 |
| Salicylic acid (2TMS) | 15.071 |
| Erythronic acid (4TMS) | 15.509 |
| DL-Phenylalanine (1TMS) | 15.807 |
| trans-Cinnamic acid (TMS) | 15.845 |
| 3-Hydroxy-Benzoic Acid | 16.046 |
| 4-Hydroxyphenylethanol | 16.128 |
| 3-Hydroxy-3-methylglutaric | 16.5649 |
| 4-hydroxy-Benzoic Acid | 17.099 |
| 1,4-lactone Pentonic acid (3TMS) | 17.12 |
| 1,4-lactone, 2-methoximine Gluconic acid | 17.286 |
| Arabinose | 17.419 |
| 1-O-methyl alpha D | 18.703 |
| 2,Deoxy-pentos-3-ylose | 18.8857 |
| 3-deoxy-Glucosone | 18.961 |
| Vanillic acid (2TMS) | 19.271 |
| 2-Keto-L-gluconic acid (5TMS) | 19.308 |
| 4-hydroxy-cis-cinnamic acid | 19.642 |
| Azelaic acid (2TMS) | 19.715 |
| Shikimic acid (4TMS) | 19.818 |
| D(-)-Quinic acid (5TMS) | 20.477 |
| Fructose MX1 | 20.641 |
| Fructose MX2 | 20.785 |
| 1,5-lactone Gluconic acid | 20.958 |
| Glucose MX1 | 21.019 |
| Unknown21.85 | 21.285 |
| Glucose MX2 | 21.285 |

TABLE 6-continued

Identified peaks and retention times of Extract A

| Compound | Retention Time |
| --- | --- |
| 1-Ethylglucopyranoside | 21.649 |
| Sorbitol | 21.841 |
| 4-hydroxy trans-cinnamic | 21.924 |
| Gluconic acid (6TMS) | 22.463 |
| Unknown 22.614 | 22.614 |
| Unknown 22.650 | 22.65 |
| 1-o-methyl beta-D-Galactopyranoside (4TMS) | 22.926 |
| 3,4-dimethoxy-trans- | 23.13 |
| n-Hexadecanoic acid | 23.274 |
| Inositol | 23.718 |
| n-Octadecan-1-ol (Steryl | 23.793 |
| trans-Ferulic acid (2TMS) | 23.944 |
| 3,4-dimethoxy-trans | 24.471 |
| 2-O-Glcyerol-beta-D-galactopyranoside (6TMS) | 24.896 |
| trans-Sinapic acid (2TMS) | 25.852 |
| 1-Benzylglucopyranoside | 27.474 |
| Thymidine (3TMS) | 27.745 |
| Uridine (3TMS) | 28.267 |
| Unknown_28.673 | 28.384 |
| Unknown_28.722 | 28.722 |
| Unknown_29.097 | 29.097 |
| Salicylic acid | 29.515 |
| (Arbutin) Hydroquinone-beta-D-glucopyranoside (5TMS) | 29.614 |
| Unknown 29.700 | 29.7 |
| Adenosine (3TMS) | 29.861 |
| Unknown_29.995 | 29.9987 |
| Sucrose | 30.073 |
| Cellobiose MX1 | 30.74 |
| Trehalose | 31.14 |
| Turanose MX1 | 31.273 |

TABLE 7

Identified peaks and retention times of Extract B

| Compound | Retention time |
| --- | --- |
| Pyruvic Acid (1TMS) | 6.99800 |
| DL- Lactic Acid (2TMS) | 7.128 |
| Glycolic Acid | 7.38260 |
| Oxalic Acid (2TMS) | 7.55710 |
| CONT 1140 | 8.44700 |
| 3-Hydroxypropanoic Acid (2TMS) | 8.49810 |
| CONT 1228 | 8.76800 |
| DL-Isoleucine (1TMS) | 9.15240 |
| Malonic Acid (2TMS) | 9.54010 |
| Methylmalonic Acid (2TMS) | 9.63460 |
| Cont. 1228.8 | 9.77600 |
| 4-Hydroxy Butyric Acid (2TMS) | 10.11450 |
| Cont: 1249.3 | 10.2423 |
| Glycine (3TMS) | 10.3667 |
| Cont: 1256.7 | 10.4578 |
| DL-Serine (2TMS) | 10.52 |
| Glycerol | 10.598 |
| Thymidine | 10.85 |
| DL-Threonine (2TMS) | 11.1777 |
| Cont 1308 | 11.2255 |
| Succinic acid (2TMS) | 11.5521 |
| DL-Glyceric Acid (3TMS) | 11.7654 |
| Glutaric acid (2TMS) | 11.93 |
| Fumaric Acid (2TMS) | 12.2187 |
| n-nonanoic acid | 12.4298 |
| 2-Methyl-1,3-butanediol | 12.5264 |
| 2-methyl-1,2-propanediol (2TMS) | 12.9108 |
| Unknown_503_459_13.1919 | 13.1919 |

TABLE 7-continued

Identified peaks and retention times of Extract B

| Compound | Retention time |
|---|---|
| 2,4-dihydroxy-Butanoic acid (3TMS) | 13.2575 |
| DL-2-methyl Malic Acid)3TMS) | 13.8718 |
| n-Decanoic acid (1TMS) | 14.168 |
| DL-Malic Acid (3TMS) | 14.6195 |
| DL-Lactic acid dimer (2TMS) | 14.8606 |
| Glutaric Acid (2TMS) | 15.0406 |
| Salicylic acid (2TMS) | 15.067 |
| Unknown_408_393_15.1528 | 15.1528 |
| DL-Pyroglutamic Acid (2TMS) | 15.2894 |
| 2-Hydroxyglutaric Acid (3TMS) | 15.353 |
| hydrocarbon contamination | 15.4061 |
| Erythronic acid (4TMS) | 15.5038 |
| Threonic Acid (4TMS) | 15.796 |
| Unknown_16.0060 | 16.066 |
| 2,3-Dihydroxybutanedioic acid (4TMS) | 16.3982 |
| Unknown_16.441 | 16.439 |
| 3-Hydroxy-3-methylglutaric acid (3TMS) | 16.5604 |
| Unknown 16.796 | |
| 4-hydroxy-Benzoic Acid (2TMS) | 17.077 |
| 2-Hydroxyhexanedioic acid (3TMS) | 17.175 |
| 1,4-lactone, 2methoxime Gluconic acid | 17.262 |
| Unknown 17.426 | |
| 2,4,5-Trihydroxypentanoic acid (4TMS) | 17.5502 |
| 3- Hydroxysebacic acid (3TMS) | 18.581 |
| Ribonic acid (5TMS) | 19.2434 |
| 2-Keto-L-gluconic acid (5TMS) | 19.3067 |
| 3 -deoxy-Glucosone | 19.53 |
| Shikimic acid (4TMS) | 19.829 |
| unknown_20.027 | 20.0266 |
| D-Psicose (5TMS) (also known as Allulose) | 20.163 |
| Unknown_20.419 | 20.419 |
| Fructose MX1 | 20.652 |
| Fructose MX2 | 20.796 |
| Glucose MX1 | 21.018 |
| Glucose MX2 | 21.296 |
| Mannitol | 21.463 |
| Ethylglucopyranoside (4TMS) | 21.7186 |
| 4-hydroxy-trans cinnamic acid | 21.954 |
| unknown_22.015 | 22.015 |
| Gulonic acid (6TMS) | 22.076 |
| Unknown_22.276 | 22.276 |
| Gluconic acid (6TMS) | 22.507 |
| Unknown_22.6352 | 22.6352 |
| Galactonic acid (6TMS) | 22.692 |
| 1-O-methyl-beta-D-Galactopyranoside (4TMS) | 22.946 |
| 1-Ethylglucopyranoside (4TMS) | 22.9484 |
| n-hexadecanoic acid (1TMS) | 23.305 |
| Inositol | 23.696 |
| Unknown_23.963 | 23.9661 |
| Unknown_24.227 | 24.2272 |
| Unknown_24.307 | 24.3072 |
| trans-Caffeic acid (3TMS) | 24.4705 |
| Unknown_24.740 | 24.7404 |
| Unknown_24.904 | 24.9038 |
| Unknown_24.9560 | 24.956 |
| n-Octadecanoic acid (1TMS) | 25.82659 |
| Unknown_26.411 | |
| Unknown_27.229 | |

TABLE 7-continued

Identified peaks and retention times of Extract B

| Compound | Retention time |
|---|---|
| (Helicin) Salicylaldehyde-beta-D-glucoside | 29.095 |
| (Arbutin) Hydroquinone-beta-D-glucopyranoside (5TMS) | 29.612 |
| Sucrose | 30.084 |
| Cellobiose MX1 | 30.762 |
| Maltose | 31.128 |
| Trehalose | 31.195 |
| 3-caffeoyl-trans-Quinic acid | 34.8481 |
| 5-caffeoyl-trans-Quinic Acid | 35.617 |
| Campesterol (1TMS) | 36.361 |
| Raffinose | 36.95 |
| 1-Kestose | 37.083 |

TABLE 8

Identified peaks and retention times of Extract D

| Compound | RT |
|---|---|
| CONT: 1038.1 | 6.252 |
| Pyruvic Acid (1TMS) | 7.05400 |
| Lactic Acid (2TMS) | 7.16200 |
| Glycolic Acid | 7.42600 |
| Oxalic Acid (2TMS) | 7.58700 |
| CONT 1228 | 8.17000 |
| 3-Hydroxypropanoic acid (2TMS) | 8.52500 |
| 3-hydroxy-pyridine (1TMS) | 8.55100 |
| CONT: 1228 | 8.76800 |
| DL-Isoleucine (1TMS) | 9.18700 |
| n-Heptanoic acid (1TMS) | 9.40500 |
| Malonic Acid (2TMS) | 9.56600 |
| Benzoic acid (1TMS) | 10.4667 |
| DL-Serine (2TMS) | 10.537 |
| Phosphoric acid (3TMS) | 10.75 |
| Thymidine (BP) | 10.857 |
| Maleic Acid (2TMS) | 11.375 |
| Succinic Acid (2TMS) | 11.565 |
| DL-Glyceric Acid (3TMS) | 11.78 |
| Itaconic acid (2TMS) | 12.072 |
| Fumaric Acid (2TMS) | 12.23 |
| n-Nonanoic acid (1TMS) | 12.438 |
| Nicotinic acid (1TMS) | 12.749 |
| Cytosine (2TMS) | 12.822 |
| 2,4-dihydroxy Butanoic Acid (3TMS) | 13.262 |
| 2-methyl-DL-Malic Acid (3TMS) | 14.319 |
| Salicylic acid (2TMS) | 14.432 |
| 3,4,5,6-D4-Salicylic acid (2TMS) | 14.555 |
| DL-Malic acid (3TMS) | 14.626 |
| Nicotinimide (1TMS) | 14.691 |
| DL-Lactic acid dimer (2TMS) | 14.863 |
| Glutaric acid (2TMS) | 15.049 |
| DL-Pyroglutamic acid (2TMS) | 15.296 |
| 2-Hydroxyglutatic acid (3TMS) | 15.365 |
| Erythronic acid (4TMS) | 15.508 |
| Trihydroxybenzene (3TMS) | 15.53 |
| DL-Phenylalanine (1TMS) | 15.82 |
| trans-Cinnamic acid (TMS) | 15.845 |
| 3-Hydroxy-Benzoic Acid (2TMS) | 16.045 |
| 4-Hydroxyphenylethanol (2TMS) | 16.128 |
| 2-oxo-Glutaric acid (1MEOX) (2TMS) | 16.16 |
| 3-Hydroxy-3-methylglutaric acid (3TMS) | 16.564 |
| 4-hydroxy-Benzoic Acid (2TMS) | 17.087 |
| 1,4-lactone Pentonic acid (3TMS) | 177.116 |
| 1,4-lactone, 2-methoxime Gluconic acid | 17.286 |
| Arabinose | 17.419 |

TABLE 8-continued

Identified peaks and retention times of Extract D

| Compound | RT |
|---|---|
| 1-O-methyl beta-D-Galactopyranoside | 18.701 |
| 2,Deoxy-pentos-3-ylose dimethoxyamine | 18.883 |
| cis-Aconitic acid (3TMS) | 18.951 |
| 4-Hydroxyphenylpropionic acid (2TMS) | 19.192 |
| Vanillic acid (2TMS) | 19.261 |
| 2-Keto-L-gluconic acid (5TMS) | 19.309 |
| 3-deoxy-Glucosone | 19.531 |
| 4-hydroxy-cis-cinnamic acid | 19.641 |
| Azelaic acid (2TMS) | 19.709 |
| Shikimic acid (4TMS) | 19.818 |
| D(−)-Quinic acid (5TMS) | 20.481 |
| Fructose MX1 | 20.63 |
| Fructose MX2 | 20.785 |
| 1,5-lactone Gluconic acid | 20.954 |
| Glucose MX1 | 20.996 |
| Glucose MX2 | 21.285 |
| Sorbitol | 21.841 |
| 4-hydroxy trans-cinnamic acid | 21.913 |
| Gluconic acid (6TMS) | 22.462 |
| 1-o-methyl beta-D-Galactopyranoside (4TMS) | 22.535 |
| 3,4-dimethoxy-trans-Cinnamic acid | 23.127 |
| n-Hexadecanoic acid (1TMS) | 23.277 |
| Inositol | 23.718 |
| n-Octadecan-1-ol (Steryl alcohol) | 23.791 |
| trans-Ferulic acid (2TMS) | 23.937 |
| trans-Caffeic acid (3TMS) | 24.468 |
| 2-O-Glcerol-beta-D-galactopyranoside (6TMS) | 25.514 |
| 1-Methyl-beta-D-galactopyranoside (4TMS) | 25.517 |
| trans-Sinapic acid (2TMS) | 25.85 |
| 1-Benzylglucopyranoside | 27.471 |
| Thymidine (3TMS) | 27.74 |
| Uridine (3TMS) | 28.272 |
| Salicylaldehyde-beta-D-glucoside (TMS) | 29.521 |
| Salicylic acid glucopyranoside (5TMS) | 29.522 |
| (Arbutin) Hydroquinone-beta-D-glucopyranoside (5TMS) | 29.924 |
| Unknown 29.704 | 29.704 |
| Adenosine (3TMS) | 29.866 |
| Sucrose | 30.073 |
| Cellobiose MX1 | 30.751 |
| Maltose | 31.129 |
| Trehalose | 31.151 |
| Turanose MX1 | 31.273 |
| Guanosine | 31.638 |
| Melibiose MX1 | 32.406 |
| beta-D-Glucopyranuronic acid (5TMS) | 33.164 |
| Galactinol | 33.573 |
| 3-p-coumaroyl-trans-Quinic acid | 33.658 |
| Unknown_33.736 | 33.736 |
| 3-caffeoyl-trans-Quinic acid | 34.859 |
| Unknown_34.708 | 35.32 |
| 4-Caffeoyl-trans-Quinic Acid | 35.418 |
| Unknown_35.549 | 35.55 |
| 5-Caffeoyl-trans-Quinic Acid | 35.619 |
| 1-Kestose | 37.083 |

TABLE 9

Library of individual compounds detected across each sample

| Compounds | Extract A | Extract B | Extract D | Notes |
|---|---|---|---|---|
| Hydroquinone-beta-D-glucopyranoside (Arbutin) (5TMS) | x | x | x | antioxidant, inhibits tyrosinase, whitening agent. |
| Salicylaldehyde-beta-D-glucoside (Helicin) | | x | x | O-glucoside |
| 1,4-lactone Pentonic acid (3TMS) | x | | x | sugar acid |
| 1,4-lactone, 2-methoximine Gluconic acid | x | | x | sugar acid |
| 1,5-lactone Gluconic acid | x | | x | sugar acid |
| 1-Benzylglucopyranoside | x | | x | glucoside |
| 1-Ethylglucopyranoside (4TMS) | x | x | | glucoside |
| 1-Kestose | | x | x | inulin |
| 1-O-methyl alpha D Mannopyranoside (4TMS) | x | | | found in cereals and alfalfa |
| 1-o-methyl beta-D-Galactopyranoside (4TMS) | x | x | x | glucoside |
| 2,Deoxy-pentos-3-ylose dimethoxyamine (2TMS) | x | | x | amine |
| 2,3-Dihydroxybutanedioic acid (4TMS) Tartatic acid | | x | | antioxidant, one of the main acids found in wine; acidifier |
| 2,4,5-Trihydroxypentanoic acid (4TMS) | | x | | fatty acid |
| 2,4-dihydroxy-Butanoic acid (3TMS) | x | x | x | carboxylic acid |
| 2-Hydroxyglutaric Acid (3TMS) | | x | x | fatty acid |
| 2-Keto-L-gluconic acid (5TMS) | x | x | x | sugar acid |
| 2-O-Glycerol-beta-D-galactopyranoside (6TMS) | x | | x | glucoside |
| 2-oxo-Glutaric acid (1MEOX) (2TMS) | | | x | sugar acid |
| 3-Hydroxysebacic acid (3TMS) | | x | | fatty acid |
| 3,4-dimethoxy-trans Cinnamic Acid | x | | x | phenolic acid |
| 3,4,5,6-D4-Salicylic acid (2TMS) | | | x | carboxylic acid |
| 3-caffeoyl-trans-Quinic acid | x | x | x | cyclic polyol |
| 3-deoxy-Glucosone | x | x | x | malliard reaction product |
| 3-Hydroxy-Benzoic Acid (2TMS) | x | | x | carboxylic acid |
| 3-Hydroxy-3-methylglutaric acid (3TMS) | x | x | x | fatty acid |
| 3-Hydroxypropanoic Acid (2TMS) | x | x | x | carboxylic acid |
| 3-hydroxy-pyridine (1TMS) | x | | x | pyridine |
| 3-p-coumaroyl-trans-Quinic acid | x | | x | cyclic polyol |
| 4-Caffeoyl-trans-Quinic Acid | x | | x | cyclic polyol |
| 4-Hydroxy Butyric Acid (2TMS) | | x | | relevant for cancer, diabetes, inflammation |
| 4-hydroxy trans-cinnamic acid | x | x | x | phenolic acid |
| 4-hydroxy-Benzoic Acid (2TMS) | | x | x | carboxylic acid |
| 4-hydroxy-cis-cinnamic acid | x | | x | phenolic acid |
| 4-Hydroxyphenylethanol (2TMS) (Tyrosol) | x | | x | antioxidant phenol |

TABLE 9-continued

Library of individual compounds detected across each sample

| Compounds | Extract A | Extract B | Extract D | Notes |
|---|---|---|---|---|
| 4-Hydroxyphenylpropionic acid (2TMS) | | | x | carboxylic acid |
| 5-caffeoyl-trans-Quinic Acid | x | x | x | cyclic polyol |
| Adenosine (3TMS) | x | | x | nucleoside |
| Arabinose | x | | x | aldopentose |
| Azelaic acid (2TMS) | x | | x | anti-acne and psoriasis |
| Benzoic acid (1TMS) | x | | x | carboxylic acid |
| beta-D-Glucopyranuronic acid (5TMS) | | | x | o-glucuronides |
| Campesterol (1TMS) | | x | | phytosterol, antioxidant and hypocholesterol-emic |
| Cellobiose MX1 | x | x | x | disaccharide |
| cis-Aconitic acid (3TMS) | | x | | organic acid |
| Cytosine (2TMS) | | x | | nucleobase |
| D(-)-Quinic acid (5TMS) | x | | x | cyclic polyol |
| DL-2-methyl Malic Acid (3TMS) | | x | | organic acid |
| DL-Isoleucine (1TMS) | | x | x | organic acid |
| DL-Lactic Acid (2TMS) | x | x | x | organic acid |
| DL-Malic Acid (3TMS) | x | x | x | organic acid |
| DL-Serine (2TMS) | x | x | x | organic acid |
| DL-Threonine (2TMS) | | x | | anti-oxidant |
| DL-Aspartic acid (2TMS) | x | | x | organic acid |
| DL-Glyceric Acid (3TMS) | x | x | x | sugar acid |
| DL-Lactic acid dimer (2TMS) | x | | x | organic acid |
| DL-Phenylalanine (1TMS) | x | | x | organic acid |
| DL-Pyroglutamic Acid (2TMS) | | x | x | organic acid |
| D-Psicose (5TMS) (also known as Allulose) | | x | | monosaccharide |
| Erythronic acid (4TMS) | x | x | x | sugar acid |
| Ethylglucopyranoside (4TMS) | | x | | glucoside |
| Fructose MX1 | x | x | x | monosaccharide |
| Fructose MX2 | x | x | x | monosaccharide |
| Fumaric Acid (2TMS) | x | x | x | carboxylic acid |
| Galactinol | x | | x | galactose metabolism intermediate |
| Galactonic acid (6TMS) | | x | | organic acid |
| Gluconic acid (6TMS) | x | x | x | sugar acid |
| Glucose MX1 | x | x | x | monosaccharide |
| Glucose MX2 | x | x | x | monosaccharide |
| Glutaric acid (2TMS) | | x | x | fatty acid |
| Glycerol | | x | | polyol compound |
| Glycine (3TMS) | | x | | amino acid |
| Glycolic Acid | x | x | x | organic acid |
| Guanosine | | x | | nucleoside |
| Gulonic acid (6TMS) | | x | | organic acid |
| Inositol | x | x | x | carbocyclic sugar |
| Itaconic acid (2TMS) | | x | | organic acid |
| Maleic Acid (2TMS) | | x | | organic acid |
| Malonic Acid (2TMS) | x | x | x | organic acid |
| Maltose | | x | | disaccharide |
| Mannitol | | x | | sugar alcohol |
| Melibiose MX1 | x | | x | reducing disaccharide |
| Methylmalonic Acid (2TMS) | | x | | carboxylic acid |
| n-Decanoic acid (1TMS) | | x | | anti-bacteria, anti-fungal, nematocide |
| n-Heptanoic acid (1TMS) | x | | x | fatty acid |
| n-hexadecanoic acid (1TMS) | x | x | x | fatty acid |
| Nicotinic acid (Niacin) (1TMS) | | x | | Vitamin B3 form |
| Nicotinimide (1TMS) | | | x | Vitamin B3 form |
| n-Nonanoic acid (1TMS) | x | x | x | fatty acid |
| n-Octadecan-1-ol (Steryl alcohol) | x | | x | fatty alcohol |
| n-Octadecanoic acid (1TMS) | | x | | hypocholestelomic |
| Oxalic Acid (2TMS) | x | x | x | organic acid |
| Phosphoric acid (3TMS) | x | | x | inorganic acid |
| Pyruvic Acid (1TMS) | x | x | x | organic acid |
| Raffinose | | x | | trisaccharide |
| Ribonic acid (5TMS) | | x | | sugar acid |
| Salicylic acid (2TMS) | x | x | x | anti-acne/antipsoriasis |
| Salicylic acid glucopyranoside (5TMS) | x | | x | glucoside |
| Shikimic acid (4TMS) | x | x | x | cyclic polyol |
| Sorbitol | x | | x | sugar alcohol |
| Stigmasterol | x | | | phytosterol |
| Succinic acid (2TMS) | x | x | x | organic acid |
| Sucrose | x | x | x | disaccharide |
| Threonic Acid (4TMS) | | x | | sugar acid |
| Thymidine | x | x | x | nucleotide |
| Thymine (2TMS) | x | | | nucleobase |
| trans-Caffeic acid (3TMS) | | x | x | phenolic acid |
| trans-Cinnamic acid (TMS) | x | | x | phenolic acid |
| trans-Ferulic acid (2TMS) | x | | x | phenolic acid |
| trans-Sinapic acid (2TMS) | x | | | phenolic acid |
| Trehalose | x | x | x | disaccharide |
| Turanose MX1 | x | | x | reducing disaccharide |
| Uracil (2TMS) | x | | | nucleobase |
| Uridine (3TMS) | x | | x | nucleoside |
| Vanillic acid (2TMS) | x | | x | phenolic acid |

Example 2 to Example 6 provide illustrative and non-limiting examples of the preparation and characterisation of extracts derived from sugar cane of the present disclosure.

Example 2. Sugar Cane Extracts Derived from Molasses

Example sugar cane extracts of the present disclosure were prepared from molasses as follows.

Sugar cane molasses was diluted with de-ionised water, mixed well to give a final Brix of 50°. This mixture was held between 20-25° C. and 95% food grade ethanol added with overhead stirring to ensure that the ethanolic mixture was evenly and quickly dispersed. This step was continued until the final ethanol content reached 76% v/v. During this time, a gelatinous precipitate formed. The precipitate was allowed to settle and the supernatant was decanted and filtered under vacuum in a Buchner Funnel through a Whatman GFA filter paper grade 1. The ethanol was subsequently removed under reduced pressure in a Buchi Rotary Evaporator at 45° C. Evaporation was continued under reduced pressure at 50-55° C. to give a syrup with a final Brix of 70° with a bitter sweet aroma. Characterisation of exemplary syrups obtained by this method is shown in Table 10.

TABLE 10

Properties of sugar cane extracts prepared from molasses

| Property | Extract 1 | Extract 2 |
|---|---|---|
| Brix (°Bx) | 65-70 | 70° (+/−2) @ 20° C. |
| pH | 4-5 | 4.6 (+/−0.2) @ 20° C. |
| Density (g/mL) | 1.25-1.35 | 1.35 (+/−0.05 @ 20° C.) |
| Colour Absorbance 420 | 69.1 | — |
| Absorbance 270 | 708 | — |
| Ratio A270/A420 | 10 | — |
| Total Polyphenol (mg/L as gallic acid equivalents) | 16,500 | Minimum 20,000 |
| Total Flavonoids (mg/L as catechin equivalents) | 2800 | Minimum 7,000 |
| ORAC | 5.0 | Minimum 2.5 mol/kg |
| CAA | — | Minimum 2.5 mol/kg as trolox equivalents |
| Conductivity (µS/cm) | 138,800 | — |
| Calcium | 5100 mg/kg | 400-1,300 mg/L |
| Iron | 110 mg/kg | 10-100 mg/L |
| Magnesium | 1800 mg/kg | 2,400-5,500 mg/L |
| Potassium | 26,000 mg/kg | 20,000-40,0000 mg/L |
| Sodium | 23 mg/100 g | 60-80 mg/100 mL |
| Zinc | — | 0.3-0.8 mg/100 mL |
| Selenium | — | 0.03-0.09 mg/100 mL |
| Chromium | — | 0.03-0.140 mg/100 mL |

Example 3. Fractionated Sugar Cane Extracts Derived from Molasses

In general, the title fractionated sugar cane extracts may be prepared using hydrophobic chromatography procedures. Extracts prepared using the processes described in Example 2 and any sugar cane derived product may be used as feedstocks for chromatography. The hydrophobic resin used for chromatography may be a food grade resin.

In a representative preparation, FPX66 resin (Dow, Amberlite FPX66, food grade)) was pre-treated by washing with de-ionised water, ethanol and then finally with de-ionised water following the manufacturer's instructions. The washed resin was filtered under vacuum through a Buchner Funnel using Whatman filter paper grade 1 (1 µm pore size). The resin granules were then used as is.

De-ionised water was added to sugar cane molasses with constant stirring until the Brix reached 20°. To a beaker containing 1 litre of the 20° Brix feedstock (maintained at 20-25° C.) and mounted on a magnetic stirrer, 500 g of wet weight pre-treated resin was added with gentle stirring to ensure effective mixing of the resin granules with the feedstock. The mixing was continued for 10 min at which point the mixture was filtered under vacuum and the resin was collected.

The collected resin was washed by resuspension in de-ionised water (1 litre). This step was repeated.

The washed resin was then suspended in 1 litre 70% ethanol solution in de-ionised water, stirred for 10 mins and the filtrate was collected by vacuum filtration. This was repeated twice more with 1 litre batches of the 70% ethanolic solution with each filtrate being collected. Finally, the three 70% ethanolic filtrates were combined and the ethanol removed by evaporation under reduced pressure. The aqueous fraction was lyophilised or spray-dried into a free flowing brown powder with a moisture content of 0.3-2.0% w/w. The properties of the ethanolic fraction are shown below in Table 11.

TABLE 11

Properties of an extract derived from sugar cane molasses

| Properties | Ethanol fraction |
|---|---|
| Colour Absorbance at 420 nm | 10 (1% in solution @ 20° C.) |
| Absorbance at 270 nm | 180 (1% in solution @ 20° C.) |
| Ratio A270 nm/A420 nm | 19 (1% in solution @ 20° C.) |
| Total Polyphenol (mg/g gallic acid equivalent) | Minimum 200 |
| Total Flavonoid (mg/g catechin equivalent) | Minimum 50 |
| Calcium (mg/kg) | 840 |
| Iron (mg/kg) | 77 |
| Magnesium (mg/kg) | 2300 |
| Potassium (mg/kg) | 1100 |
| Sodium (mg/g) | 1700 |
| Zinc (mg/kg) | 48 |
| Selenium (mg/kg) | 0.18 |
| Chromium (mg/kg) | 1.8 |

Figure 8:
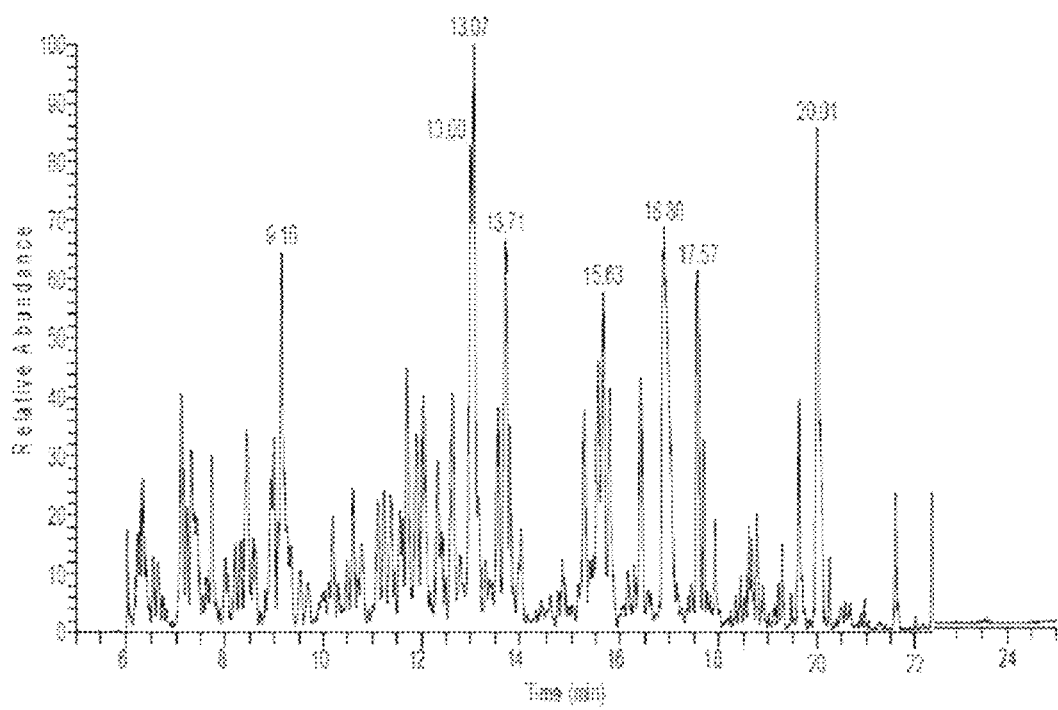
FIG. 8 exhibits a LCMS spectrum of a representative extract derived from sugar cane molasses prepared according to Example 3.

FIG. 8 exhibits a LCMS spectrum of a representative extract derived from sugar cane molasses using this process.

Example 4. Sugar Cane Extracts Derived from Dunder

A scheme for the preparation of the title sugar cane extracts is shown in FIG. 9.

Sugar cane dunder was allowed to settled overnight for eight hours in a V-bottom tank. The supernatant was then subjected to sequential microfiltration through: (i) a 5 micron filter; (ii) a 1 micron filter; (iii) a 0.5 micron filter; and (iv) a 0.1 micron filter.

The filtered supernatant was subsequently concentrated in a heat exchanger to remove water to provide the liquid extract with 55° Bx.

The properties of an extract derived from dunder is shown below in Table 12.

TABLE 12

Properties of an extract derived from dunder

| Properties | Sugar cane extract |
|---|---|
| Brix | 55° (+/−2) @ 20° C. |
| pH | 4.6 (+/−0.2) @ 20° C. |
| Density | 1.28 g/mL (+/−0.05) @ 20° C. |
| Colour Absorbance 420 | 190-280 |
| Absorbance 270 | 2300-3000 |
| Ratio A270/A420 | 10-15 |
| Total Polyphenol (mg/L as gallic acid equivalent) | Minimum 45,000 |
| Total Flavonoid (mg/L as catechin equivalent) | Minimum 10,000 |
| Conductivity (uS/m) | 250,000-350,000 |
| Calcium (mg/kg) | 3,000-4,000 |
| Iron (mg/kg) | 100-150 |
| Magnesium (mg/kg) | 3,000-5,000 |
| Potassium (mg/kg) | 30,000-40,000 |
| Sodium (mg/kg) | 2,000-3,000 |
| Zinc (mg/100 g) | 0.5-1.5 |
| Selenium (mg/100 g) | 0.02-0.05 |
| Chromium (mg/100 g) | 0.20-0.5 |

Figure 10A:
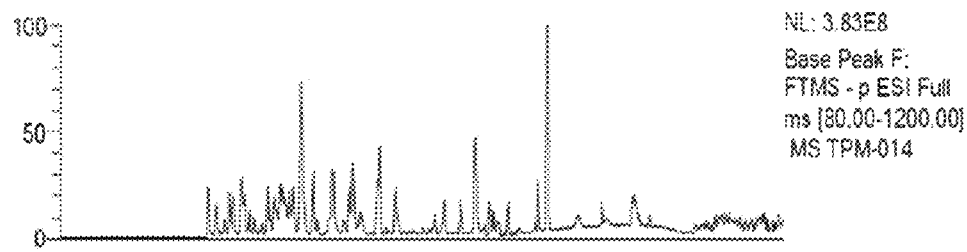
FIGS. 10A and 10B exhibit LCMS spectra for sugar cane dunder starting material (FIG. 10A) and an extract of sugar cane dunder prepared according to Example 4 (FIG. 10B).
Figure 10B:
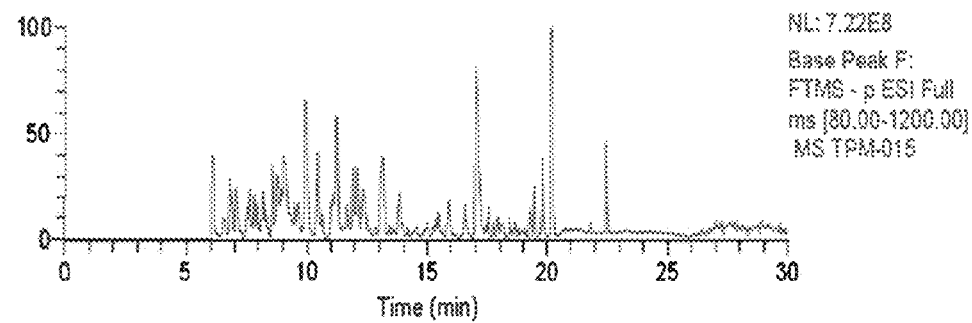

FIGS. 10A and 10B exhibit example LCMS spectra for sugar cane dunder starting material (FIG. 10A) and an extract of sugar cane derived dunder (FIG. 10B) in accordance with the above process.

Example 5. Hybrid Sugar Cane Extracts Derived from a Combination of Sugar Cane Molasses and Dunder A scheme for the preparation of the title sugar cane extracts is shown in FIG. 11.

Sugar cane mill molasses was diluted with water and mixed with settled sugar cane dunder (as described above) and stirred well to provide a mixture with 50° Bx. The combined mixture of molasses and dunder was maintained at a constant temperature of between 20-25° C. and 95% food grade ethanol added and stirred to ensure that the ethanol was evenly and quickly dispersed. Ethanol was added until the ethanol level was 76% v/v.

The addition and mixing of ethanol led to the formation of a gelatinous precipitate. The precipitate in the mixture was allowed to settle and the supernatant was removed by decantation and vacuum filtration in a Buchner funnel through a Whatman GFA filter paper 1.

The ethanol was removed from the supernatant under vacuum in a Buchi rotary evaporator at 45° C. Evaporation of water from the supernatant was performed under vacuum at 50-55° C. until the final syrup reaches 70° Bx.

Table 13 shows the properties of the hybrid sugar cane extract obtained.

TABLE 13

Properties of a hybrid sugar cane extract

| Property | Sugar cane extract |
| --- | --- |
| Brix | 70° (+/−2) @ 20° C. |
| pH | 4.6 (+/−0.2) @ 20° C. |
| Density | 1.35 (+/−0.05 @ 20° C.) |
| Colour Absorbance 420 | 90-120 |
| Absorbance 270 | 1900-2300 |
| Ratio A270/A420 | 15-30 |
| Total Polyphenol (mg/L as gallic acid equivalent) | Min 30,000 milligrams per litre (as gallic acid equivalents) |
| Total Flavonoid (mg/L as catechin equivalent) | Minimum 10,000 |
| Conductivity (µS/m) | 180,000-200,000 |
| Calcium (mg/kg) | 80-160 |
| Iron (mg/kg) | 2-8 |
| Magnesium (mg/kg) | 300-600 |
| Potassium (mg/kg) | 2000-4000 |
| Sodium (mg/kg) | 60-180 |
| Zinc (mg/100 g) | 1.5-3.0 |
| Selenium (mg/100 g) | 0.04-0.09 |
| Chromium (mg/100 g) | 0.015-0.50 |

Example 6. Characteristics of Extracts Derived from Sugar Cane

TABLE 14

Two example extracts derived from sugar cane of the present disclosure

| | Extract 3 prepared according to the process of Example 2 | Extract 4 prepared according to the process of Example 3 |
| --- | --- | --- |
| Brix | 65-70 Brix | 68-70 Brix |
| pH | 5.3-5.9 | 4.5-4.7 |
| Density | 1.25-1.35 | 1.35 |
| Colour Absorbance 420 | 69.1 | 65 |

TABLE 14-continued

Two example extracts derived from sugar cane of the present disclosure

| | Extract 3 prepared according to the process of Example 2 | Extract 4 prepared according to the process of Example 3 |
| --- | --- | --- |
| Absorbance 270 | 708 | 1506 |
| Ratio A270/A420 | 10 | 23 |
| Total Polyphenol (mg/L gallic acid equivalent) | 16,500 | 24,000-28,000 |
| Total Flavonoid (mg/L catechin equivalent) | 2800 | 5900 |
| Conductivity (us) | 138,800 | 57,200 |
| Calcium (mg/kg) | 5100 | 1614 |
| Iron (mg/kg) | 110 | 52 |
| Magnesium (mg/kg) | 1800 | 2250 |
| Potassium (mg/kg) | 26,000 | 21,000 |
| Sodium (mg/100 g) | 23 | 47 |

Table 15 exhibits a component comparison between molasses and extracts derived from sugar cane of the present disclosure.

TABLE 15

A comparison between molasses and an extract derived from sugar cane of the present disclosure.

| Components | Molasses | Extract derived from sugar cane |
| --- | --- | --- |
| Total solids (g/L) | 80.5 | 70 |
| Fructose (g/L) | 131.9 | 74.5 |
| Glucose (g/L) | 107.1 | 52.8 |
| Sucrose (g/L) | 473.8 | 343 |
| Total sugars (g/L) | 722.8 | 470 |
| Ratio (Fructose + Glucose/Sucrose) | 0.50 | 0.41 |
| Total polyphenol (mg GAE/L) | 20,000 | 25,000-28,000 |
| Antioxidants (ABTS mg GAE/L) | 7,000-8,500 | 10,500-11,500 |
| Calcium (mg/L) | 5746 | 2145 |
| Magnesium (mg/L) | 2374 | 3003 |
| Sodium (mg/L) | 303 | 605 |
| Potassium (mg/L) | 20,794 | 27170 |

Example 7 to Example 24 provide illustrative and non-limiting examples of activities of the extracts derived from sugar cane of the present disclosure.

Example 7

Compositions comprising an extract derived from sugar cane of the present disclosure were tested on human subjects to evaluate the use in preventing, improving or treating skin conditions.

A panel of human subjects was convened to evaluate the use of a composition comprising an extract derived from sugar cane of the present disclosure in preventing, improving or treating skin conditions.

Application of the compositions was topically to the face of the human subjects. The biophysical effects of the topically applied treatment composition was evaluated pre- and post-application when used by the same participants. 11 subjects were recruited for the study, with results tabulated for all 10 subjects who completed to 12 weeks.

Wrinkle reduction was determined using silicone impressions and profilometry and skin blemishes using a Minolta Spectrophotometer. In addition, a photographic record was taken of each of the test participants.

Test Material Handling

Each of the test samples of extracts derived from sugar cane of the present disclosure was assigned a unique laboratory code number and entered into a daily log identifying the lot number, sample description, date received and tests requested.

Standards for Inclusion in the Study
 i. Individuals nominally between the ages 40 to 65 years.
 ii. Individuals not taking medication or under the care of a physician for a period of one month prior to commencement and throughout the entire test period.
 iii. Individuals who have completed a preliminary medical history.
 iv. Individuals who have read, understood and signed an informed consent document.
 v. Individuals who understand instructions for use and are willing to cooperate with the program as stated.
 vi. Individuals free of any dermatological or systemic disorder that would interfere with the results, at the discretion of the Investigator.
 vii. Individuals able to cooperate with the investigator and the research staff, be willing to complete the full course of the study.
 viii. Individuals with self-described dry skin.

Standards for Exclusion from the Study
 i. Individuals who are under doctor's care.
 ii. Individuals who are currently taking medication which in the opinion of the investigator would mask or interfere with the results.
 iii. Individuals with any history of sensitivity to cosmetics in general and moisturisers in particular.
 iv. Individuals with any form of skin cancer, or any disease that would interfere with the test results.
 v. Individuals diagnosed with chronic skin allergies.
 vi. Female volunteers who indicate that they are pregnant or nursing an infant.
 vii. Individuals with excessive hair on the test sites.
 viii. Individuals with known hypersensitivity to cosmetic products.

Preparation

In order to precondition the test sites and keep topical treatments constant for all test subjects, the participants were required to abstain from use of moisturizers and skin treatments on the test area for a period of 10 days prior to study commencement. At the completion of the 10 days 'washout' period, the participants were required to return to the test facility at the time specified by the technician for the study commencement.

Product Application Instructions

On the first day of the study, the participants were trained on how to apply. The treatment composition was then evenly applied to the faces. The participants were required to continue to use the materials as instructed, that is, twice per day, morning and evening.

Instrumental Description Profilometry (Wrinkles and Roughness)

At each visit, a single silicone replica was made of the target area and a photographic record was kept of this target for subsequent relocation. The samples were stored in controlled conditions for comparative measurement. Comparative analysis of skin profilometry was conducted, using surface roughness and wrinkle depth analysis. Concurrent use of other moisturiser or skin care products did not occur in the skin area under study. The height of the replicated wrinkles were measured using Miyomoto Surftest profilometer. Ry (depth) and Ra (mean roughness) were recorded at each time of measuring operation. The area scanned from each sample was clearly mapped so as to determine the same area in respective two month sampling.

Instrumental Description L*a*b* Colour Measurement

A Minolta Chromometer hand held spectrophotometer was utilized. This tri-stimulus instrument was utilised to determine colour values and changes vis background colour in an unpigmented adjoining area. Specular Component Included (SCI) values were documented.

Digital Photography

At each time point, a series of high resolution digital photographs were collected.

The subject was presented with a clean face, with hair pulled off the face, with no jewellery (unless permanent) and with a black drape used to standardize clothing. Subject positioning was reproduced upon return visit. A light booth was used so as to provide controlled reproducible light conditions. The booth consists of an array of 8 equally spaced fluorescent tubes in a semicircular configuration. The software driven system allows the position and expression of the test subjects to be aligned to a high degree. Lux values were calibrated and documented.

Results

Table 16 exhibits the results of the skin roughness test. On average, skin roughness was reduced by 17% at 8 weeks and 20% at 12 weeks of the use of the treatment preparation.

TABLE 16

Results of the skin roughness test
Start Date:
End Date: All measurements in um
Skin Rougness
Ra

| Subject ID | Age | Race | T = 0 week 0 Ra | T = 1 week 8 Ra | T = 2 Week 12 Ra |
|---|---|---|---|---|---|
| M068 | 58 | A | 8.7 | 4.51 | 3.08 |
| M570 | 44 | C | 7.51 | 8.62 | 6.43 |
| M638 | 57 | C | 2.59 | 2.69 | 2 |
| M549 | 58 | C | 11.94 | 9.55 | 9.15 |
| M041 | 59 | A | 6.53 | 4.43 | 6 |
| M664 | 52 | C | 6.12 | 7.89 | 5.5 |
| M661 | 49 | C | 3.67 | 3.27 | 3.85 |
| M632 | 51 | A | 5.57 | 3.75 | 5.68 |
| M612 | 60 | A | 3.68 | 4.41 | 4.48 |
| M618 | 56 | A | 6.14 | 4.05 | 3.71 |
| M394 | 54 | C | 8.67 | 5.87 | 6.97 |
| n = 11 | | Average | 6.465 | 5.367 | 5.168 |
| | | Difference (% improvement) | | 17% | 20.1% |

Table 17 exhibits the results of the wrinkle depth test. On average, wrinkle depth was reduced by 9% at 8 weeks and 20% at 12 weeks of the use of the treatment preparation.

TABLE 17

Results of the wrinkle depth test

| | | | Wrinkle Depth Ry | | |
|---|---|---|---|---|---|
| Subject ID | Age | Race | T = 0 week 0 Ry | T = 1 week 8 Ry | T = 2 week 12 Ry |
| M068 | 58 | A | 46 | 35.5 | 23.6 |
| M570 | 44 | C | 35 | 37 | 29.2 |
| M638 | 57 | C | 35 | 32.7 | 27.8 |
| M549 | 58 | C | 56.5 | 41 | 35.6 |
| M041 | 59 | A | 37.9 | 35.9 | 36.5 |

TABLE 17-continued

Results of the wrinkle depth test

|  |  |  | Wrinkle Depth Ry | | |
|---|---|---|---|---|---|
| Subject ID | Age | Race | T = 0 week 0 Ry | T = 1 week 8 Ry | T = 2 week 12 Ry |
| M664 | 52 | C | 47.9 | 47.1 | 35.6 |
| M661 | 49 | C | 30 | 37.5 | 32.1 |
| M632 | 51 | A | 27.5 | 22.2 | 23 |
| M612 | 60 | A | 45 | 46.5 | 43.2 |
| M618 | 56 | A | 39.4 | 31.9 | 34.4 |
| M394 | 54 | C | 37.5 | 31.4 | 28.7 |
| n = 11 |  | Average | 39.791 | 36.245 | 31.791 |
|  |  | Difference (% improvement) |  | 8.9% | 20.1% |

FIGS. 12A and 12B exhibit a 58 year old subject before (FIG. 12A) and after the 12 week trial (FIG. 12B). After the 12 week trial the subject measured a 49% wrinkle reduction and a 65% reduction in skin roughness.

FIGS. 13A and 13B exhibit another 58 year old subject before (FIG. 13A) and after the 12 week trial (FIG. 13B). After the 12 week trial the subject measured a 37% wrinkle reduction.

Table 18 exhibits the results of the colour reduction and pigmented spot test. On average, the pigmented area was reduced in colour by 2% at 8 weeks of the use of the treatment preparation.

TABLE 18

Colour reduction and pigmented spot test
L* Value SCI
Pigmented Spot

| Subject ID | Age | T = 0 | T = 1 | T = 2 |
|---|---|---|---|---|
| M041 | 60 | 56.41 | 57.28 | 57.30 |
| M394 | 54 | 56.94 | 58.41 | 58.46 |
| M632 | 50 | 56.67 | 57.03 | 57.26 |
| M661 | 49 | 57.53 | 58.63 | 59.16 |
| M664 | 52 | 57.01 | 57.65 | 57.35 |
| M570 | 44 | 56.46 | 60.70 | 58.98 |
| M612 | 60 | 56.73 | 58.24 | 58.41 |
| M549 | 58 | 55.82 | 56.39 | 56.79 |
| M638 | 57 | 55.09 | 56.23 | 56.39 |
| M618 | 56 | 53.14 | 53.30 | 53.38 |
| M068 | 58 | 54.69 | 56.13 | 55.22 |
| Average % vis Initial |  | 56.0 | 57.3 102.2% | 57.2 102.0% |
| L*a*b* |  |  | L* | |
| Whitening Scale |  |  | Black = 0 White = 100 | |

Table 19 exhibits the results of the colour reduction—surrounding area test. A Minolta Colour Computer was used. On average, the surrounding area was reduced in colour by less than 1% at 8 weeks of the use of the treatment preparation.

TABLE 19

Colour reduction—surrounding area test
L* Value SCI
Surrounding area

| Subject ID | Age | T = 0 | T = 1 | T = 2 | T = 3 |
|---|---|---|---|---|---|
| M041 | 60 | 61.25 | 62.54 | 61.73 | 0.00 |
| M394 | 54 | 62.37 | 63.47 | 62.52 | 0.00 |
| M632 | 50 | 64.48 | 65.28 | 65.77 | 0.00 |
| M661 | 49 | 61.22 | 61.42 | 60.65 | 0.00 |
| M664 | 52 | 63.58 | 63.87 | 63.85 | 0.00 |
| M570 | 44 | 61.35 | 63.00 | 62.49 | 0.00 |
| M612 | 60 | 60.75 | 61.79 | 62.47 | 0.00 |
| M549 | 58 | 60.87 | 61.21 | 61.58 | 0.00 |
| M638 | 57 | 61.76 | 62.12 | 61.51 | 0.00 |
| M618 | 56 | 62.07 | 61.62 | 61.76 | 0.00 |
| M068 | 58 | 63.08 | 62.41 | 62.24 | 0.00 |
| Average % vis Initial |  | 62.1 | 62.6 100.9% | 62.4 100.6% | 0.0 0.0% |
| L*a*b* |  |  |  | L* | |
| Whitening Scale |  |  |  | Black = 0 White = 100 | |

Adverse Events

No adverse effects were observed.

Example 8. Psoriasis Study 1

A composition comprising an extract derived from sugar cane of the present disclosure was tested on a human subject to evaluate the use in preventing, improving or treating psoriasis.

Application of the composition was topically to the affected skin area twice a day. The biophysical effects of the topically applied treatment composition was evaluated pre-application, during the application process and post-application.

A photographic record shown in FIGS. 14A, 14B, 14C and 14D was taken of the test participant. (FIG. 14A) exhibits the subject's knee before the 6 week trial, (FIG. 14B) exhibits the subject's knee after 2 weeks of continuous use of a composition comprising an extract derived from sugar cane of the present disclosure, (FIG. 14C) exhibits the subject's knee after 4 weeks of continuous use of a composition comprising an extract derived from sugar cane of the present disclosure, (FIG. 14D) exhibits the subject's knee after 6 of weeks of continuous use of a composition comprising an extract derived from sugar cane of the present disclosure.

The subject had suffered from psoriasis for 35 years and had tried many different types of diets, creams, tablets and natural remedies. Some of these were at great expense with minimal short term effects and no relief from the itching and unsightly plaques caused by the psoriasis. The subject reported that the composition reduced the size of the affected areas and relieved the itching and that the affected areas begun to return to normal skin colour and tone after using the composition. The subject also reported that the composition was gentle on the skin, "user" friendly and moreover did not leave any oily residue. The subject had tried other treatments which only improved the affected areas for short periods and did not have any long term effects, causing frustration and disappointment. Furthermore, some of the ingredients of the other treatments caused damage to the subject's clothing.

Example 9. Psoriasis Study 2

A composition comprising an extract derived from sugar cane of the present disclosure was tested on a human subject to evaluate the use in preventing, improving or treating psoriasis.

Application of the composition was topically to the affected skin area twice a day. The biophysical effects of the topically applied treatment composition was evaluated pre-application, during the application process and post-application.

FIGS. 15A, 15B and 15C are photographic records taken of the test participant. (FIG. 15A) exhibits the subject's knee before the 3 month trial, (FIG. 15B) exhibits the subject's knee after 1 month of continuous use of a composition comprising an extract derived from sugar cane of the present disclosure, (FIG. 15C) exhibits the subject's knee after 3 months of continuous use of a composition comprising an extract derived from sugar cane of the present disclosure.

Example 10. Elastase Inhibitory Assay

As described above, wrinkle formation in the skin is accompanied by a decrease in skin elasticity and the curling of elastic fibres such as elastin in the dermis. Elastase inhibitors suppress elastase activity and prevent the damage of dermal elastin, thus helping mitigate wrinkle formation.

An elastase inhibition assay was performed to determine the elastase inhibition potential of an extract derived from sugar cane of the present disclosure. Two batches (replicate 1 and replicate 2) of an extract derived from sugar cane of the present disclosure in a concentration of from 0.12 mg/mL to 250 mg/mL were tested for the ability to inhibit elastase.

To measure elastase inhibitory potential of an extract derived from sugar cane of the present disclosure, a test sample of an extract derived from sugar cane was mixed and incubated with N-methoxysuccinyl-Ala-Ala-Pro-Val-chloromethyl ketone in tris-HCl buffer for 15 min. Then elastase was added to the mixture and incubated for 15 min. The inhibition rate was measured at 410 nm and calculated as follows:

$$\text{Elastase inhibition (\%)} = 1 - \left( \frac{\text{Abs}_{sample+elastase} - \text{Abs}_{blank-elastase}}{\text{Abs}_{blank+elastase} - \text{Abs}_{sample-elastase}} \right) \times 100$$

Wherein, $\text{Abs}_{sample+elastase}$=absorbance of test sample after incubation with elastase, $\text{Abs}_{sample-elastase}$=absorbance of test sample before incubation with elastase, $\text{Abs}_{blank+elastase}$=absorbance of blank after incubation with elastase, and $\text{Abs}_{blank-elastase}$=absorbance of blank before incubation with elastase.

N-methoxysuccinyl-Ala-Ala-Pro-Val-chloromethyl ketone, a human leukocyte elastase (HLE) inhibitor, was used as an assay control. Two batches (replicate 1 and replicate 2) of N-methoxysuccinyl-Ala-Ala-Pro-Val-chloromethyl ketone in a concentration of from 0.12 μM to 250 μM were used in the control assay.

Table 20(a) exhibits the relationship between concentrations of the extract derived from sugar cane of the present disclosure and elastase inhibition. Table 20(b) exhibits the relationship between the concentrations of N-methoxysuccinyl-Ala-Ala-Pro-Val-chloromethyl ketone and elastase inhibition.

TABLE 20 (a)

Elastase inhibition assay results

| Sample Conc. (mg/ml) | Inhibition (%) Replicate 1 | Replicate 2 | Average | CV(%) |
|---|---|---|---|---|
| 250.00 | 94.65% | 94.68% | 94.67% | 0.02 |
| 125.00 | 77.55% | 77.89% | 77.72% | 0.31 |
| 62.50 | 68.33% | 66.50% | 67.41% | 1.92 |
| 31.25 | 61.05% | 63.56% | 62.31% | 2.84 |
| 15.63 | 48.05% | 55.52% | 51.78% | 10.19 |
| 7.81 | 39.72% | 44.51% | 42.12% | 8.04 |
| 3.91 | 25.08% | 35.29% | 30.18% | 23.91 |
| 1.95 | 12.91% | 21.21% | 17.06% | 34.39 |
| 0.98 | 5.62% | 13.00% | 9.31% | 56.11 |
| 0.49 | 2.06% | 4.42% | 3.24% | 51.50 |
| 0.24 | −1.76% | 3.62% | 0.93% | 410.18 |
| 0.12 | −1.48% | −2.62% | −2.05% | −39.26 |

TABLE 20 (b)

Elastase inhibition assay results

| N-methoxysuccinyl-Ala-Ala-Pro-Val-chloromethyl ketone Conc. (uM) | Inhibition (%) Relicate 1 | Replicate 2 | Average | CV(%) |
|---|---|---|---|---|
| 250.00 | 87.63% | 87.79% | 87.71% | 0.13 |
| 125.00 | 87.08% | 87.26% | 87.17% | 0.14 |
| 62.50 | 86.04% | 86.22% | 86.13% | 0.15 |
| 31.25 | 84.26% | 84.46% | 84.36% | 0.17 |
| 15.63 | 81.14% | 80.78% | 80.96% | 0.31 |
| 7.81 | 76.17% | 76.35% | 76.26% | 0.16 |
| 3.91 | 68.45% | 69.03% | 68.74% | 0.60 |
| 1.95 | 58.83% | 59.60% | 59.21% | 0.92 |
| 0.98 | 45.26% | 46.08% | 45.67% | 1.27 |
| 0.49 | 29.92% | 30.65% | 30.29% | 1.70 |
| 0.24 | 18.31% | 18.17% | 18.24% | 0.55 |
| 0.12 | 10.14% | 10.54% | 10.34% | 2.71 |

Table 21 exhibits maximum degree of inhibition and concentration used in the assay and $EC_{50}$ (effective concentration at 50% of maximal inhibition) for an extract derived from sugar cane of the present disclosure in comparison to the assay control, N-methoxysuccinyl-Ala-Ala-Pro-Val-chloromethyl ketone.

TABLE 21

Elastase inhibition assay results

| Elastase Inhibition Assay | Maximum inhibition achieved | Concentration inducing the maximum inhibition | $EC_{50}$ |
|---|---|---|---|
| An extract derived from sugar cane | 94.67% | 250.00 mg/mL | 14.38 mg/mL |
| N-methoxysuccinyl-Ala-Ala-Pro-Val-chloromethyl ketone | 87.71% | 250 μM | 0.83 μM (0.42 μg/mL) |

Figure 16A:
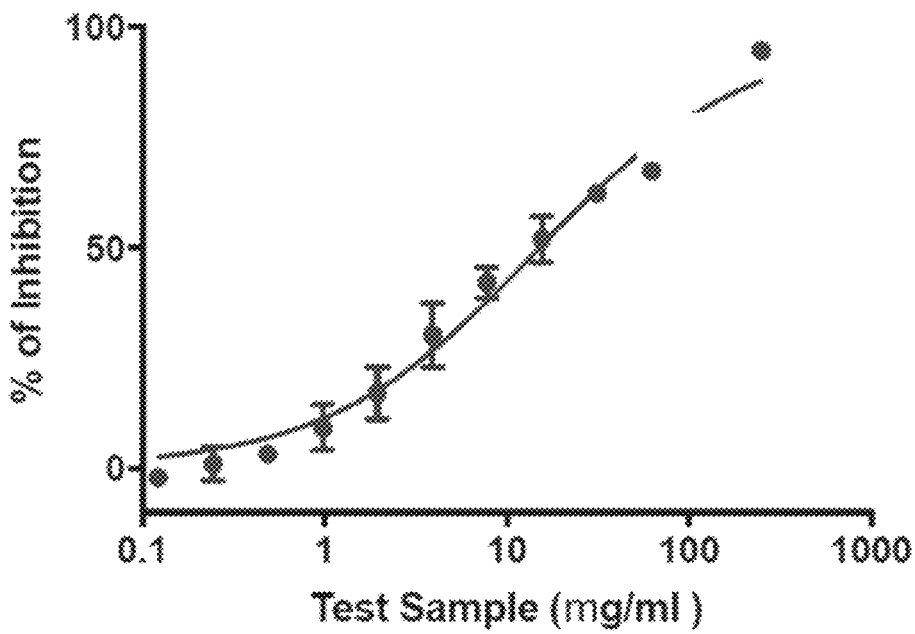
FIG. 16A exhibits the elastase inhibition of an extract derived from sugar cane of the present disclosure.

FIG. 16A exhibits the elastase inhibition of an extract derived from sugar cane of the present disclosure. The $EC_{50}$ observed was 14.38 mg/mL.

Figure 16B:
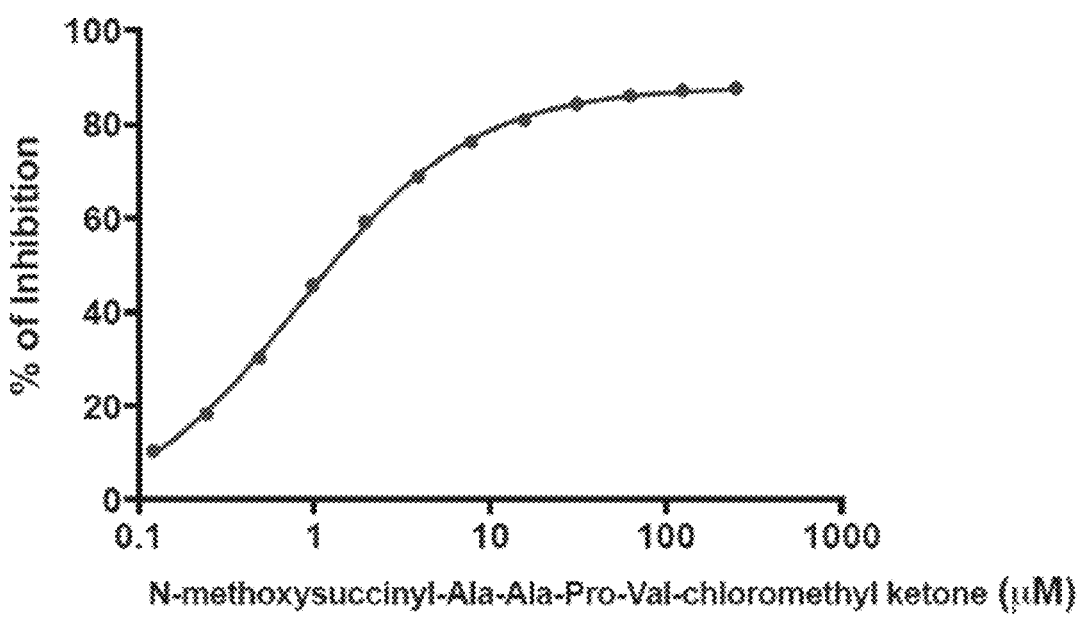
FIG. 16B exhibits the elastase inhibition of the control compound N-methoxysuccinyl-Ala-Ala-Pro-Val-chloromethyl ketone.

FIG. 16B exhibits the elastase inhibition of the control compound N-methoxysuccinyl-Ala-Ala-Pro-Val-chloromethyl ketone. The $EC_{50}$ observed was 0.83 μM.

An extract derived from sugar cane of the present disclosure demonstrated elastase inhibition activity. At a concentration of 250 mg/mL, an extract derived from sugar cane of the present disclosure has achieved maximum elastase inhibition of 94.67%. The $EC_{50}$ of the extract was 14.38 mg/mL.

Example 11. Collagenase Inhibition Assay

As described above, the collagen content of skin is the net balance between collagen synthesis and collagen breakdown. It is known that with age collagen synthesis in the skin is reduced. Additionally, environmental stress such as smoking, UV exposure, pollution and inflammation stimulate the production of collagen-degrading enzymes that causes collagen breakdown. Collagenase and MMP-1, two of the key collagen-degrading enzymes, are considered to be central to the causes of skin aging. Direct inhibition of these enzymes can be an effective approach to mitigate collagen breakdown in the skin thereby improving skin health, general condition and tone and reduction of wrinkles.

A collagenase inhibition assay was performed to determine the collagenase inhibition of an extract derived from sugar cane of the present disclosure. Two batches (replicate 1 and replicate 2) of an extract derived from sugar cane of the present disclosure in a concentration of from 0.17 mg/mL to 350 mg/mL were tested for the ability to inhibit collagenase.

To measure collagenase inhibition potential of an extract derived from sugar cane of the present disclosure, a test sample of an extract derived from sugar cane was mixed sequentially with type-I collagen substrate and a diluted collagenase enzyme solution. After incubation for 30 minutes at 37° C., fluorescence was measured at excitation maxima of 495 nm and emission maxima of 515 nm. The inhibition percentage was calculated as follows.

Collagenase inhibition activity (%) =

$$\left(1 - Abs_{sample} - \frac{Abs_{blank}}{Abs_{positive\ control}} - Abs_{negative\ control}\right) \times 100$$

Wherein,
$Abs_{sample}$=absorbance of the sample test,
$Abs_{blank}$=absorbance of the sample blank,
$Abs_{positive\ control}$=absorbance of the positive control, and
$Abs_{negative\ control}$=absorbance of the negative control.

1,10-phenanthroline was used as a positive assay control. Two batches (replicate 1 and replicate 2) of 1,10-phenanthroline in a concentration of from 1.7 μM to 3500 μM were used in the positive control assay. A negative control was performed with a buffer and a collagen substrate but without collagenase enzyme.

Table 22(a) exhibits the relationship between concentrations of the extract derived from sugar cane of the present disclosure and collagenase inhibition. Table 22(b) exhibits the relationship between concentrations of 1,10-phenanthroline and collagenase inhibition.

TABLE 22(a)

Collagenase inhibition assay results

| Sample Conc. (mg/ml) | Inhibition (%) Replicate 1 | Replicate 2 | Average | CV(%) |
|---|---|---|---|---|
| 350.00 | 89.73% | 90.23% | 89.98% | 0.39 |
| 175.00 | 77.75% | 81.61% | 79.68% | 3.42 |
| 87.50 | 65.46% | 62.90% | 64.18% | 2.82 |
| 43.75 | 46.80% | 53.88% | 50.34% | 9.95 |
| 21.88 | 38.86% | 42.29% | 40.58% | 5.97 |
| 10.94 | 24.99% | 31.28% | 28.13% | 15.80 |
| 5.47 | 9.08% | 14.16% | 11.62% | 30.89 |
| 2.73 | −5.54% | −2.96% | −4.25% | −42.96 |
| 1.37 | −19.31% | −14.76% | −17.03% | −18.89 |
| 0.68 | −28.14% | −22.59% | −25.37% | −15.48 |
| 0.34 | −33.41% | −29.42% | −31.41% | −9.00 |
| 0.17 | −39.84% | −32.26% | −36.05% | −14.88 |

TABLE 22(b)

Collagenase inhibition assay results

| 1,10-phenanthroline Conc. (uM) | Inhibition (%) Relicate 1 | Replicate 2 | Average | CV(%) |
|---|---|---|---|---|
| 3500.00 | 79.75% | 78.24% | 78.99% | 1.35 |
| 1750.00 | 76.83% | 77.71% | 77.27% | 0.81 |
| 875.00 | 77.01% | 77.72% | 77.37% | 0.64 |
| 437.50 | 76.63% | 77.39% | 77.01% | 0.70 |
| 218.75 | 75.14% | 75.78% | 75.46% | 0.61 |
| 109.38 | 71.77% | 71.54% | 71.66% | 0.23 |
| 54.69 | 57.26% | 59.74% | 58.50% | 3.00 |
| 27.34 | 25.64% | 24.25% | 24.95% | 3.95 |
| 13.67 | −7.40% | −6.00% | −6.70% | −14.72 |
| 6.84 | −22.85% | −20.46% | −21.65% | −7.83 |
| 3.42 | −27.08% | −24.45% | −25.76% | −7.24 |
| 1.71 | −29.63% | −28.47% | −29.05% | −2.82 |

Table 23 exhibits maximum degree of inhibition and concentration used in the assay and $EC_{50}$ (effective concentration at 50% of maximal inhibition) for an extract derived from sugar cane of the present disclosure in comparison to the assay control, 1,10-phenanthroline.

TABLE 23

Collagenase inhibition assay results

| Collagenase Inhibition Assay | Maximum inhibition achieved | Concentration inducing the maximum inhibition | $EC_{50}$ |
|---|---|---|---|
| An extract derived from sugar cane | 89.98% | 350.00 mg/mL | 29.65 mg/mL |
| 1,10-phenanthroline | 78.99% | 3.50 mM | 26.85 μM (4.84 μg/mL) |

Figure 17A:
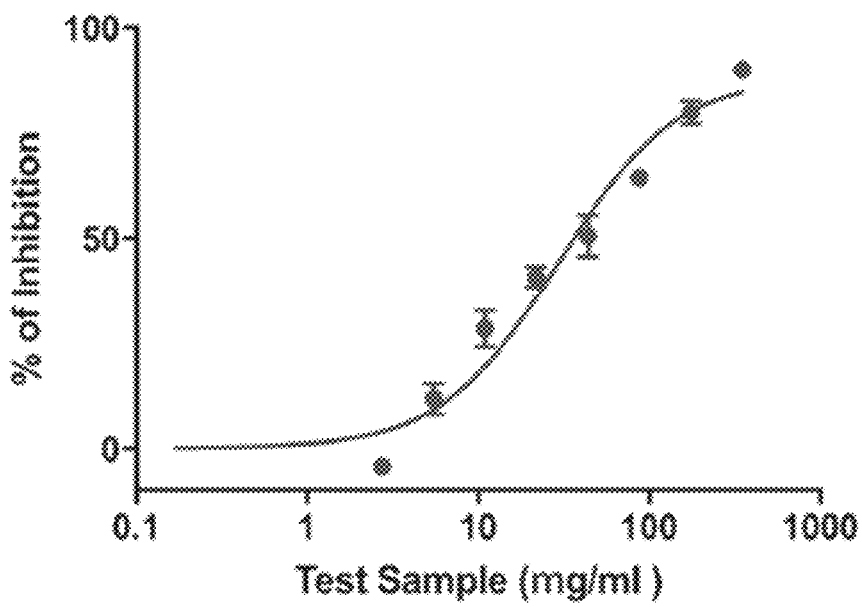
FIG. 17A exhibits the collagenase inhibition of an extract derived from sugar cane of the present disclosure.

FIG. 17A exhibits the collagenase inhibition of an extract derived from sugar cane of the present disclosure. The $EC_{50}$ observed was 29.65 mg/mL.

Figure 17B:
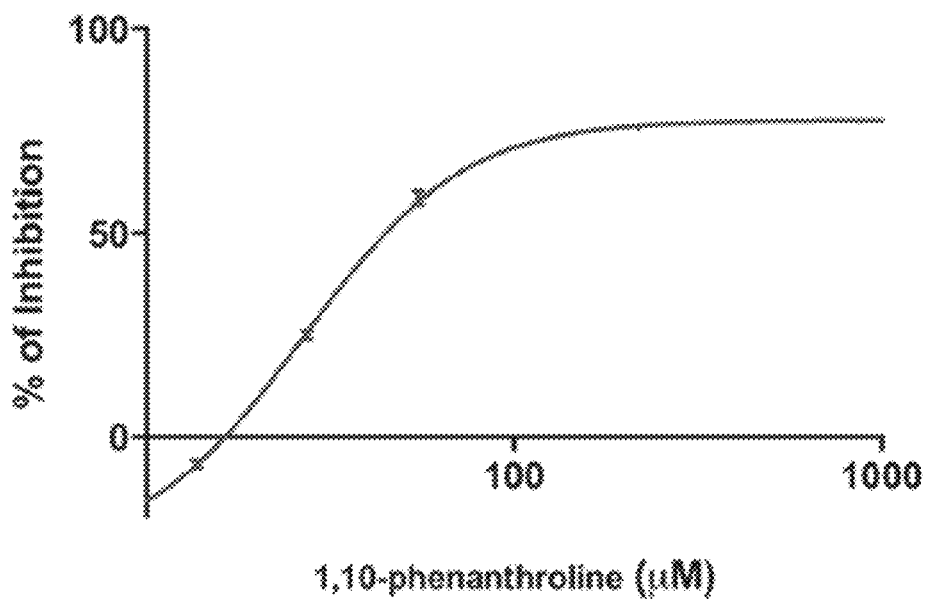
FIG. 17B exhibits the collagenase inhibition of control compound 1,10-phenanthroline.

FIG. 17B exhibits the collagenase inhibition of the control compound 1,10-phenanthroline. The $EC_{50}$ observed was 26.85 μM.

An extract derived from sugar cane of the present disclosure demonstrated collagenase inhibition activity. At a concentration of 350 mg/mL, an extract derived from sugar cane of the present disclosure achieved maximum elastase inhibition of 89.98%. The $EC_{50}$ of the extract was 29.65 mg/mL.

Example 12. Tyrosinase Inhibition Assay

As described above, colour of mammalian skin is determined by many factors, one of which is the production and distribution of melanin pigmentation. In melanin biosynthesis process, tyrosinase is the key enzyme that catalyses the first step of melanogenesis. Substantial studies have shown that melanin reduction and skin-whitening can be achieved, at least partially, by deactivating of tyrosinase. Therefore, tyrosinase inhibitors have become increasingly important in cosmetic and medicinal products used in the prevention of hyperpigmentation.

A tyrosinase inhibition assay was performed to determine the tyrosinase inhibition potential of an extract derived from sugar cane of the present disclosure. Two batches (replicate 1 and replicate 2) of an extract derived from sugar cane of the present disclosure in a concentration of from 0.31 mg/mL to 10 mg/mL were tested for the ability to inhibit tyrosinase.

To measure tyrosinase inhibition potential of an extract derived from sugar cane of the present disclosure, tyrosinase was added to a mixture of a test sample solution containing an extract derived from sugar cane, L-DOPA, and phosphate buffer (pH 6.8), which was then incubated at 37° C. for 5 hours. Tyrosinase activity was determined through the amount of dopachrome production in the mixture, which was measured by optical density at 450 nm. Dopachrome is a cyclization product of L-DOPA, an intermediate in the biosynthesis of melanin.

Kojic acid, a known tyrosinase inhibitor, was used as a positive assay control. One sample of kojic acid in a concentration from 3.91 µM to 1000 µM was used in the positive control assay.

Table 24(a) exhibits the relationship between concentrations of the extract derived from sugar cane of the present disclosure and tyrosinase inhibition. Table 24(b) exhibits the relationship between the concentrations of kojic acid and tyrosinase inhibition.

TABLE 24(a)

Tyrosinase inhibition assay results

| Sample Conc. (mg/ml) | Inhibition (%) Replicate 1 | Replicate 2 | Average |
|---|---|---|---|
| 10.00 | 87.65% | 88.72% | 88.19% |
| 5.00 | 61.18% | 65.10% | 63.14% |
| 2.50 | 23.59% | 29.13% | 26.36% |
| 1.25 | −14.95% | −11.11% | −13.03% |
| 0.63 | −23.18% | −18.88% | −21.03% |
| 0.31 | −17.83% | −32.45% | −25.14% |

TABLE 24(b)

Tyrosinase inhibition assay results

| Kojic Acid Conc. (uM) | Inhibition (%) Result |
|---|---|
| 1000.00 | 90.12% |
| 500.00 | 75.45% |
| 250.00 | 52.40% |
| 125.00 | 30.45% |
| 62.50 | 12.35% |
| 31.25 | 1.23% |

TABLE 24(b)-continued

Tyrosinase inhibition assay results

| Kojic Acid Conc. (uM) | Inhibition (%) Result |
|---|---|
| 15.63 | −4.66% |
| 7.81 | −9.33% |
| 3.91 | −11.66% |

Table 25 exhibits maximum degree of inhibition and concentration used in the assay and $EC_{50}$ (effective concentration at 50% of maximal inhibition) for an extract derived from sugar cane of the present disclosure in comparison to the assay control, kojic acid.

TABLE 25

Tyrosinase inhibition assay results

| Tyrosinase inhibition Assay | Maximum inhibition achieved | Concentration inducing the maximum inhibition | $EC_{50}$ |
|---|---|---|---|
| An extract derived from sugar cane | 88.19% | 10.00 mg/mL | 3.62 mg/mL |
| kojic acid | 90.12% | 1000 µM | 226.50 µM (32.2 µg/mL) |

Figure 18A:
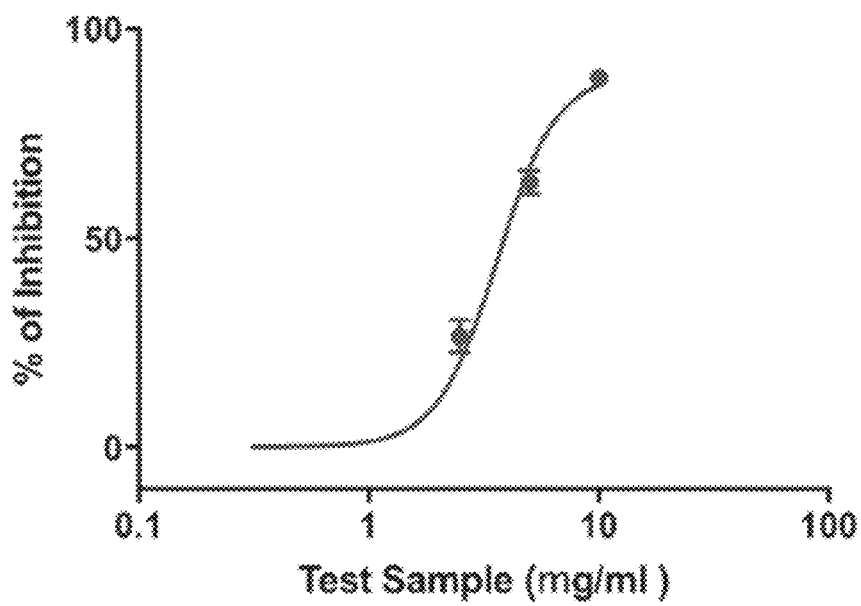
FIG. 18A exhibits the tyrosinase inhibition of an extract derived from sugar cane of the present disclosure.

FIG. 18A exhibits the tyrosinase inhibition of an extract derived from sugar cane of the present disclosure. The $EC_{50}$ observed was 3.62 mg/mL.

Figure 18B:
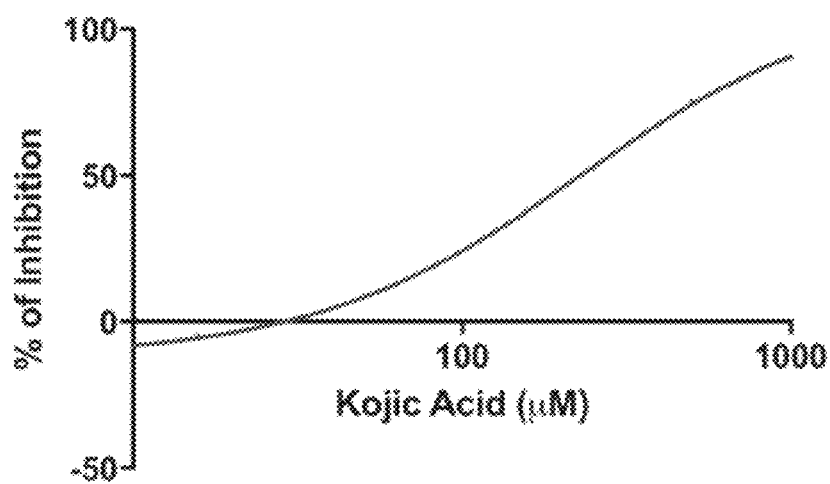
FIG. 18B exhibits the tyrosinase inhibition of control compound kojic acid.

FIG. 18B exhibits the tyrosinase inhibition of the control kojic acid. The $EC_{50}$ observed was 226.50 µM.

An extract derived from sugar cane of the present disclosure demonstrated tyrosinase inhibition activity. At a concentration of 10 mg/mL, an extract derived from sugar cane of the present disclosure has achieved maximum elastase inhibition of 88.19%. The $EC_{50}$ of the extract was 3.62 mg/mL. The $EC_{50}$ observed was 226.50 µM.

Example 13. Cellular Melanin Pigmentation Inhibition Assay

As described above, melanin is essential in protecting human skin against UV radiation, but over production of melanin is also a major consequence of UV damage and aging process that induces pigmentation disorders such as freckles and senile lentigo (i.e., age spots). Excessive melanin has also been viewed as a melanoma precursor. Melanin inhibition is a desirable effect sought in various fronts of cosmetic industry to achieve skin whitening, lessen aging appearance, and preventing melanoma.

A melanin production inhibition assay was performed to determine the potential of an extract derived from sugar cane of the present disclosure to inhibit melanin production. Two batches (replicate 1 and replicate 2) of an extract derived from sugar cane of the present disclosure in a concentration of from 1.56 mg/mL to 50 mg/mL were tested for the ability to inhibit melanin production in human skin cells.

To measure melanin pigmentation inhibition potential of an extract derived from sugar cane of the present disclosure, a test sample of an extract derived from sugar cane, in combination with theophylline, was added to a pre-incubated human skin cell culture. After incubating for 72 hours, the cells were washed with phosphate-buffered saline (PBS), lysed in 1 M NaOH, and boiled for 5 minutes to solubilize the melanin. The inhibition rates of the lysates were measured at 490 nm and expressed as a percentage relative to the value of the untreated control.

Chloroquine, a known melanin production inhibitor, was used as an assay control. Two batches (replicate 1 and replicate 2) of chloroquine in a concentration from 0.31 µM to 10 µM were used in the control assay.

Table 26(a) exhibits the relationship between concentrations of the samples of an extract derived from sugar cane of the present disclosure and melanin production inhibition.

Table 26(b) exhibits the relationship between concentrations of chloroquine and their melanin production inhibition.

TABLE 26(a)

Melanin production inhibition assay results

| Sample | Melanin inhibition (%) | | | |
|---|---|---|---|---|
| Conc (mg/ml) | Replicate 1 | Replicate 2 | Average | CV |
| 50.00 | 78.57% | 80.28% | 79.43% | 2% |
| 25.00 | 51.91% | 56.31% | 54.11% | 6% |
| 12.50 | −0.43% | −2.63% | −1.53% | −102% |
| 6.25 | 1.04% | −5.07% | −2.02% | −214% |
| 3.13 | −1.16% | 0.55% | −0.31% | −396% |
| 1.56 | −1.90% | −0.67% | −1.28% | −67% |

TABLE 26(b)

Melanin production inhibition assay results

| Chloroquine | Melanin inhibition (%) | | | |
|---|---|---|---|---|
| Conc (µM) | Replicate 1 | Replicate 2 | Average | CV |
| 10.00 | 85.66% | 90.55% | 88.11% | 4% |
| 5.00 | 79.79% | 86.40% | 83.09% | 6% |
| 2.50 | 76.61% | 75.63% | 76.12% | 1% |
| 1.25 | 36.50% | 32.10% | 34.30% | 9% |
| 0.63 | 15.47% | 16.69% | 16.08% | 5% |
| 0.31 | 1.77% | 0.06% | 0.92% | 132% |

Table 27 exhibits maximum degree of inhibition and concentration used in the assay and $EC_{50}$ (effective concentration at 50% of maximal inhibition) for an extract derived from sugar cane of the present disclosure in comparison to the assay control, chloroquine.

TABLE 27

Melanin production inhibition assay results

| Melanin production inhibition Assay | Maximum inhibition achieved | Concentration inducing the maximum inhibition | $EC_{50}$ |
|---|---|---|---|
| An extract derived from sugar cane | 79.43% | 50.00 mg/mL | 23.98 mg/mL |
| Chloroquine | 88.11% | 10 µM | 1.43 µM (0.74 µg/mL) |

Figure 19A:
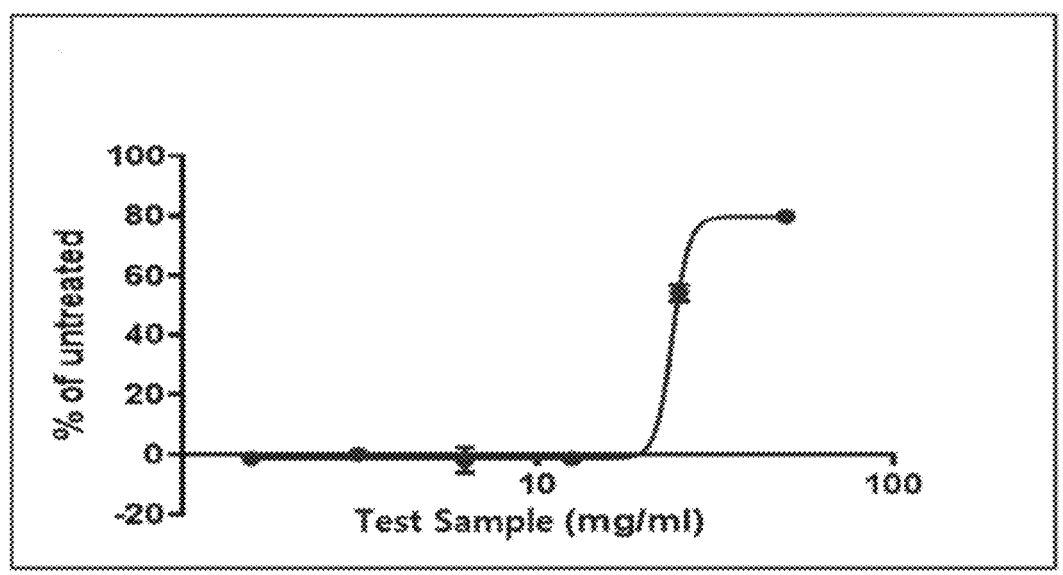
FIG. 19A exhibits the inhibition of melanin production by an extract derived from sugar cane of the present disclosure.

FIG. 19A exhibits the melanin production inhibition of an extract derived from sugar cane of the present disclosure. The $EC_{50}$ of the extract was 23.98 mg/mL.

Figure 19B:
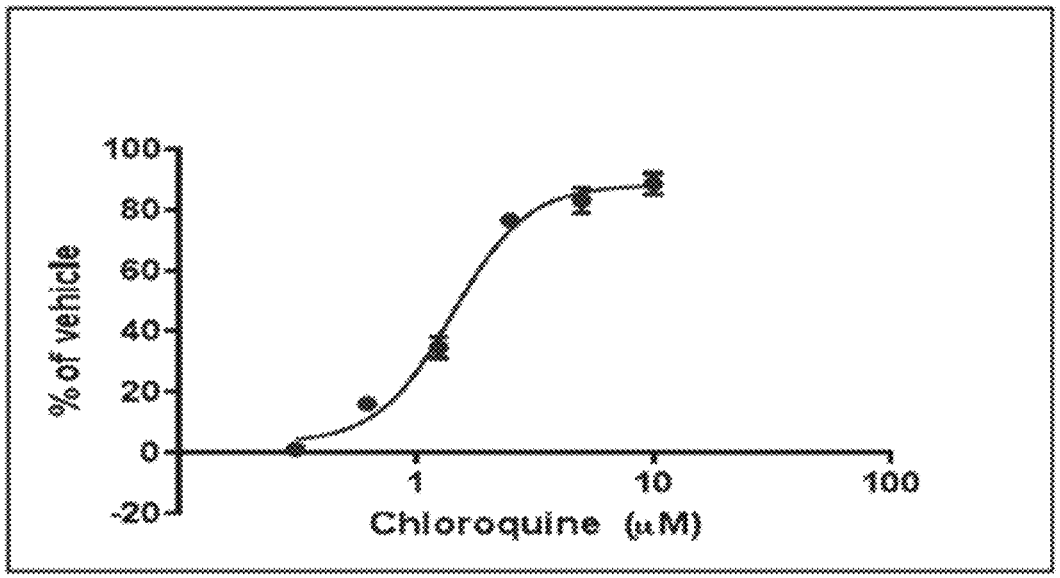
FIG. 19B exhibits the inhibition of melanin by the control compound chloroquine.

FIG. 19B exhibits the melanin production inhibition of the control chloroquine. The $EC_{50}$ of the extract was 1.43 µM.

An extract derived from sugar cane of the present disclosure demonstrated melanin production inhibition activity. At a concentration of 50 mg/mL, an extract derived from sugar cane of the present disclosure has achieved maximum melanin production inhibition of 79.43%. The $EC_{50}$ of the extract was 23.98 mg/mL.

Example 14. Melanoma Anti-Proliferative Assay

The anti-proliferative effects of an extract derived from sugar cane of the present disclosure were assessed in the mouse melanoma cancer cell line, B16.

The rapid colourimetric assay for cellular growth and survival, Thiazolyl Blue Tetrazolium Bromide (MTT) assay was used to asses cell proliferation. The MTT assay is a robust and reliable method which acquires the signal of mitochondrial performances and hence assesses cellular viability.

NAD(P)H-dependent cellular oxidoreductase enzymes of the mitochondria are capable of reducing the tetrazolium dye MTT 3-(4,5-dimethylthiazol-2-yl)-2,5-diphenyltetrazolium bromide to its insoluble formazan, which has a purple colour. The reduction reaction takes place only when mitochondrial enzymes are active and therefore conversion can be directly related to the number of viable cells. The absorbance of the purple solution can be quantified by measuring a wavelength by a spectrophotometer.

Mouse melanoma cancer cells were seeded in 96 well plates and an extract derived from sugar cane of the present disclosure added at varying concentrations (0-500 µg/ml) over 6 days, with media change containing an extract derived from sugar cane of the present disclosure on day 3. Cultures were grown in a humidified incubator at 5% $CO_2$ and 37° C. Cellular proliferation was assessed via spectrophotometry (Biorad microplate reader, 6.0) using wavelength 570 nm on days 3-6. The Experiment was conducted in triplicate.

Dose dependent anti-proliferative effects of an extract derived from sugar cane of the present disclosure were observed in the mouse melanoma cancer cell line B16. A partial effect was observed at 200 µg/ml ($p<0.05$) with complete antiproliferative effect being observed at 400 µg/ml ($p<0.05$).

Figure 20A:
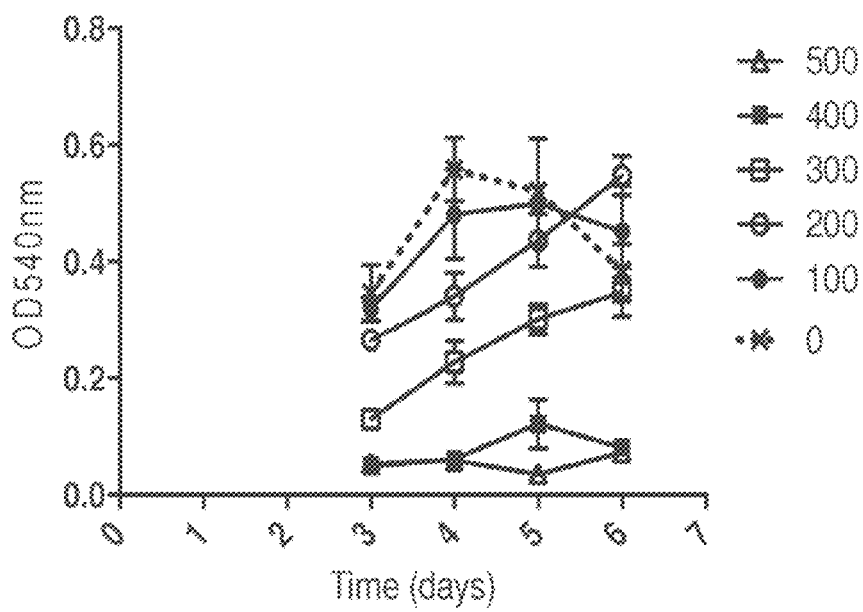
FIG. 20A exhibits the anti-proliferative effects of an extract derived from sugar cane of the present disclosure on mouse melanoma cells, B16.

FIG. 20A exhibits the anti-proliferative effects of an extract derived from sugar cane of the present disclosure on mouse melanoma cells, B16.

To ensure that the extract derived from sugar cane of the present disclosure was inhibiting proliferation in the melanoma cell line and not causing toxicity to cells, melanoma cells were cultured in the presence (400 µg/ml) or absence of an extract derived from sugar cane of the present disclosure for 24-72 hours and imaged.

Figure 20B:
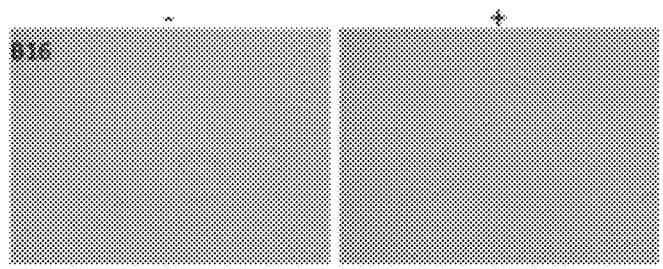
FIG. 20B exhibits 24 hour cell survival of mouse melanoma cells in the presence of an extract derived from sugar cane of the present disclosure.

FIG. 20B exhibits 24 hour cell survival of mouse melanoma cells in the presence of an extract derived from sugar cane of the present disclosure.

Figure 20C:
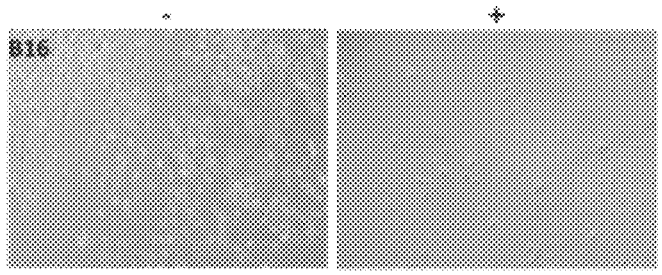
FIG. 20C exhibits 48 hour cell survival of mouse melanoma cells in the presence of an extract derived from sugar cane of the present disclosure.

FIG. 20C exhibits 48 hour cell survival of mouse melanoma cells in the presence of an extract derived from sugar cane of the present disclosure.

Figure 20D:
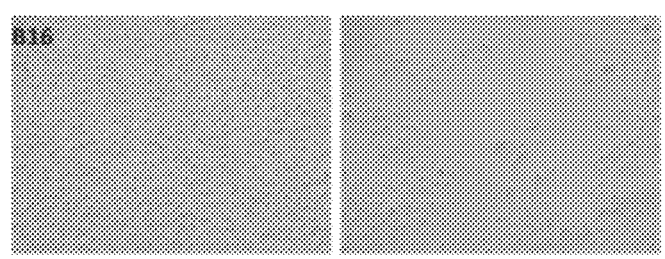
FIG. 20D exhibits 72 hour cell survival of mouse melanoma cells in the presence of an extract derived from sugar cane of the present disclosure.

FIG. 20D exhibits 72 hour cell survival of mouse melanoma cells in the presence of an extract derived from sugar cane of the present disclosure.

Example 15. Cellular Telomerase Activity Assay

As described above, telomerase is an enzyme which builds telomeres, the regions of repetitive sequences at each end of chromosomes in most eukaryotes. Telomerase can slow, stop or perhaps even reverse the telomere shortening that happens with age, however, the amount and activity of telomerase also declines with age. Activation of telomerase can reverse skin cell aging and revert the skin to a more youthful physical and genetic state.

A cellular telomerase activity assay determines the ability of a test material to stimulate telomerase activity in human cells, which translates to the material's anti-aging potential.

A cellular telomerase activity assay was performed to determine telomerase activity potential of an extract derived from sugar cane of the present disclosure. Two batches (replicate 1 and replicate 2) of an extract derived from sugar cane of the present disclosure in a concentration of from 0.16 mg/mL to 5 mg/mL were tested for the telomerase activity potential.

In the cellular telomerase activity assay, telomerase activity level of human cells treated with (and without) a test sample of an extract derived from sugar cane of the present disclosure was monitored. Specifically, a telomeric repeat amplification protocol (TRAP assay) was used for the assay. The TRAP assay was divided into three main steps: extension, amplification, and detection of telomerase products. In the extension phase, telomeric sequences were added to the telomerase substrate, a non-telomeric oligonucleotide, through the action of telomerase present in the cell extract. The products of the extension step were amplified by PCR using specific primers and finally were analyzed via electrophoresis.

Cycloastragenol, a known telomerase activator, was used as an assay control. Two batches (replicate 1 and replicate 2) of cycloastragenol in a concentration from 0.06 µM to 3 µM were used in the control assay.

Table 28(a) exhibits the relationship between concentrations of an extract derived from sugar cane of the present disclosure and telomerase activation. Table 28(b) exhibits the relationship between the concentrations of ycloastragenol and telomerase activation.

TABLE 28(a)

Cellular telomerase activity assay results

| Sample | Telomerase activity | | | |
|---|---|---|---|---|
| Conc (mg/ml) | Replicate 1 | Replicate 2 | Average | CV |
| 5.00 | 5097.83 | 5891.83 | 5494.83 | 10% |
| 2.50 | 2885.83 | 3722.83 | 3304.33 | 18% |
| 1.25 | 881.83 | 2576.83 | 1729.33 | 69% |
| 0.63 | 107.83 | 615.83 | 361.83 | 99% |
| 0.31 | 662.83 | 384.83 | 523.83 | 38% |
| 0.16 | −93.17 | 480.83 | 193.83 | 209% |

TABLE 28(b)

Cellular telomerase activity assay results

| Cycloastragenol | Telomerase activity | | | |
|---|---|---|---|---|
| Conc (µM) | Replicate 1 | Replicate 2 | Average | CV |
| 3.00 | 20995.83 | 22822.83 | 21909.33 | 6% |
| 1.00 | 15590.83 | 15521.83 | 15556.33 | 0% |
| 0.50 | 7834.83 | 7167.83 | 7501.33 | 6% |
| 0.25 | 5415.83 | 5631.83 | 5523.83 | 3% |
| 0.13 | 2080.83 | 1752.83 | 1916.83 | 12% |
| 0.06 | 925.83 | 1848.83 | 1387.33 | 47% |

Table 29 exhibits a concentration of half-maximal telomerase activation of an extract derived from sugar cane of the present disclosure in comparison to the assay control, cycloastragenol.

TABLE 29

Cellular telomerase activity assay results

| Cellular Telomerase Activity Assay | $EC_{50}$ |
|---|---|
| An extract derived from sugar cane | 2.94 mg/mL |
| Cycloastragenol | 0.79 µM (0.39 µg/mL) |

Figure 21A:
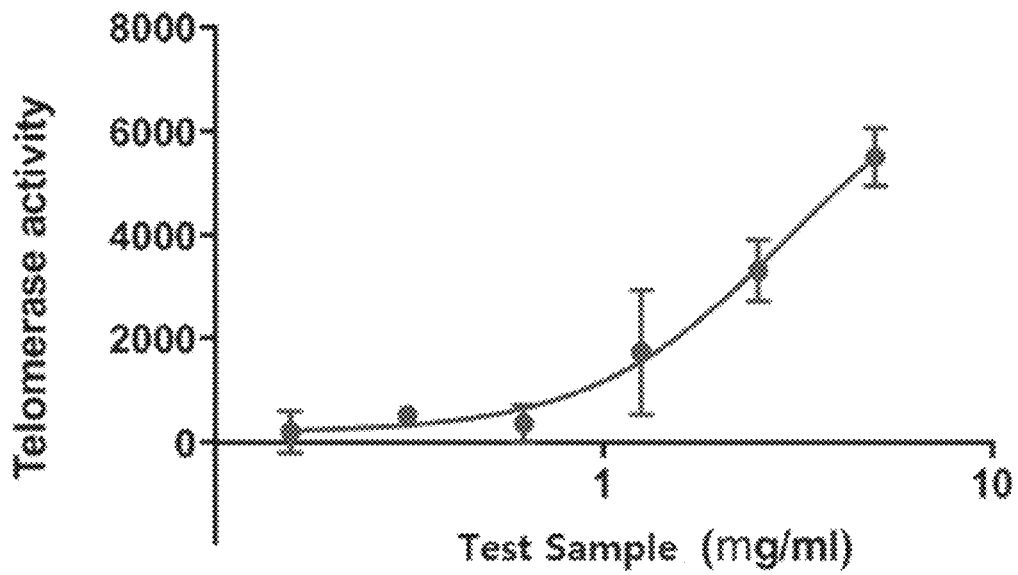
FIG. 21A exhibits the activation of telomerase by an extract derived from sugar cane of the present disclosure.

FIG. 21A exhibits the telomerase activation of an extract derived from sugar cane of the present disclosure. The $EC_{50}$ observed was 2.94 mg/mL.

Figure 21B:
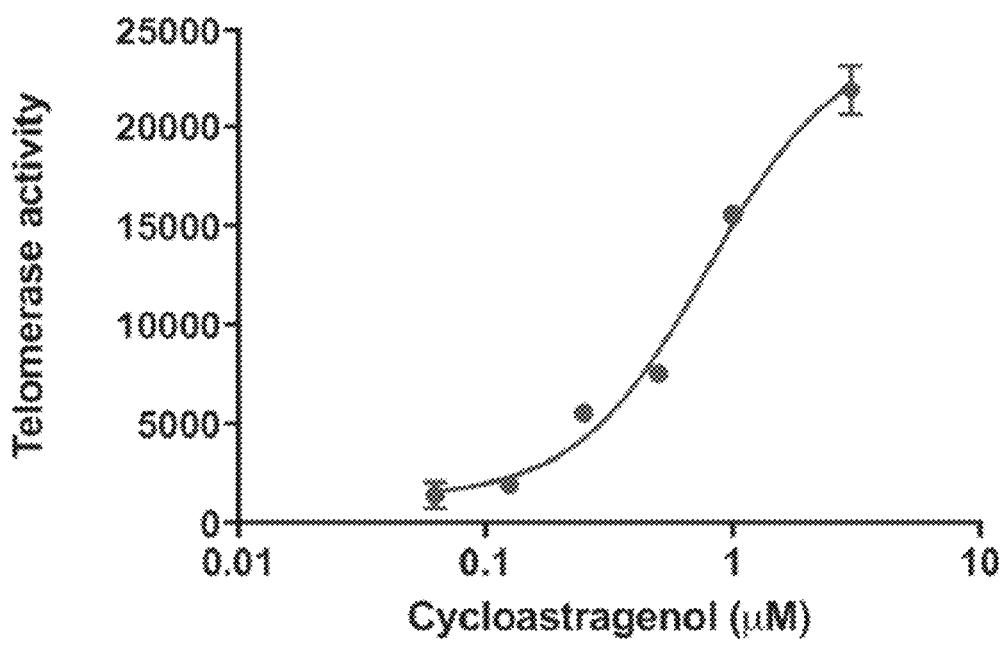
FIG. 21B exhibits the activation of telomerase by the control compound cycloastragenol.

FIG. 21B exhibits the telomerase activation of the control cycloastragenol. The $EC_{50}$ observed was 0.79 µM.

An extract derived from sugar cane of the present disclosure demonstrated telomerase enhancing activities. The $EC_{50}$ of the extract was 2.94 mg/mL.

Example 16. MMP-1 Inhibition Assay

As described above, when human skin experiences environmental stress such as UV irradiation, the skin cells undergo a number of changes including increased level of free radicals, sunburn inflammation (erythema), tanning, etc. At the molecular level, environmental stress causes DNA damage, increases pro-inflammatory cytokine levels (e.g. interleukins), and increases matrix metalloproteinases (MMPs) levels that cause excessive breakdown of connective tissue components and increased wrinkle appearance.

The UV protection function of an extract derived from sugar cane of the present disclosure on skin using human skin cells was investigated. MMP-1, one of the key matrix metalloproteinases (MMPs) that is viewed as an indicator for tissue integrity breakdown and wrinkle formation, was used as a biomarker for skin damage. MMP-1 inhibitors have been related to skin aging prevention and therapy.

An MMP-1 inhibition assay was performed to determine the MMP-1 inhibition potential of an extract derived from sugar cane of the present disclosure. Two batches (replicate 1 and replicate 2) of an extract derived from sugar cane of the present disclosure in a concentration of from 0.31 mg/mL to 5 mg/mL were tested for the ability to inhibit MMP-1 in human skin cells.

In order to determine the UV protection ability of a test sample of an extract derived from sugar cane of the present disclosure, human skin cells were treated with (and without) the test sample followed by UV irradiation. The treated cells were then disrupted by subjection to several freeze-thaw cycles, and the proteins were obtained by centrifugation. Using the collected lysate, zymography was used to determine the enzymatic activity of secreted MMP-1.

In the zymography, the proteins were separated by electrophoresis under denaturing (sodium dodecyl sulfate, SDS), nonreducing conditions. The separation occurred in a polyacrylamide gel containing a collagen substrate that was co-polymerized with the acrylamide. During electrophoresis, the SDS caused the MMPs to denature and become inactive. After electrophoresis, the gel was washed and subsequently incubated in an appropriate activation buffer. During this incubation, the concentrated, renatured MMPs in the gel digested the collagen substrate. After incubation, the gel was stained with Coomassie® Blue, and the MMPs were detected as clear bands against a blue background of undegraded substrate. The clear bands in the gel was quantified by densitometry.

Avobenzone, a known MMP-1 inhibitor, was used as an assay control. Two batches (replicate 1 and replicate 2) of avobenzone in a concentration from 0.31 μM to 10 μM were used in the control assay.

Table 30(a) exhibits the relationship between concentrations of an extract derived from sugar cane of the present disclosure and MMP-1 inhibition. Table 30(b) exhibits the relationship between the concentrations of avobenzone and MMP-1 inhibition.

TABLE 30(a)

MMP-1 inhibition assay results

| Sample | MMP-1 Inhibition (%) | | | |
|---|---|---|---|---|
| Conc (mg/mL) | Replicate 1 | Replicate 2 | Average | CV |
| 5.00 | 101.62% | 104.43% | 103.0% | 1.9% |
| 2.50 | 95.83% | 96.74% | 96.3% | 0.7% |
| 1.25 | 70.66% | 67.03% | 68.8% | 3.7% |
| 0.63 | 23.00% | 24.84% | 23.9% | 5.5% |
| 0.31 | 10.96% | | 11.0% | |

TABLE 30(b)

MMP-1 inhibition assay results

| Avobenzone | MMP-1 inhibition (%) | | | |
|---|---|---|---|---|
| Conc (%) | Replicate 1 | Replicate 2 | Average | CV |
| 10.00 | 95.44% | 99.52% | 97.5% | 3.0% |
| 5.00 | 85.34% | 96.03% | 90.7% | 8.3% |
| 2.50 | 77.44% | 82.22% | 79.8% | 4.2% |
| 1.25 | 56.96% | 39.99% | 48.5% | 24.8% |
| 0.63 | 22.51% | 65.72% | 44.1% | 69.3% |
| 0.31 | | 5.0% | 5.0% | |

Table 31 exhibits maximum degree of inhibition and concentration used in the assay and $EC_{50}$ (effective concentration at 50% of maximal inhibition) for an extract derived from sugar cane of the present disclosure in comparison to the assay control, avobenzone.

TABLE 31

MMP-1 inhibition assay results

| MMP-1 inhibition Assay | Maximum inhibition achieved | Concentration inducing the maximum inhibition | $EC_{50}$ |
|---|---|---|---|
| An extract derived from sugar cane | 103% | 5 mg/mL | 1.05 mg/mL |
| Avobenzone | 97.50% | 10% | 1.22% |

Figure 22A:
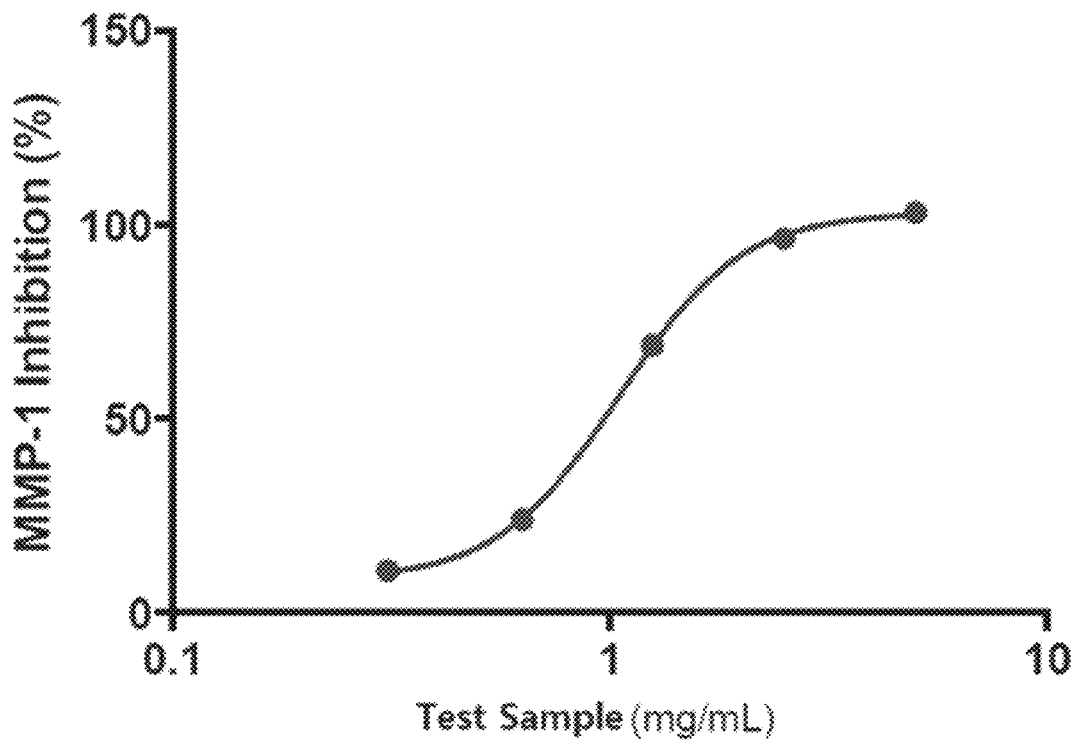
FIG. 22A exhibits the inhibition of MMP-1 by an extract derived from sugar cane of the present disclosure.

FIG. 22A exhibits the MMP-1 inhibition of an extract derived from sugar cane of the present disclosure. The $EC_{50}$ observed was 1.05 mg/mL.

Figure 22B:
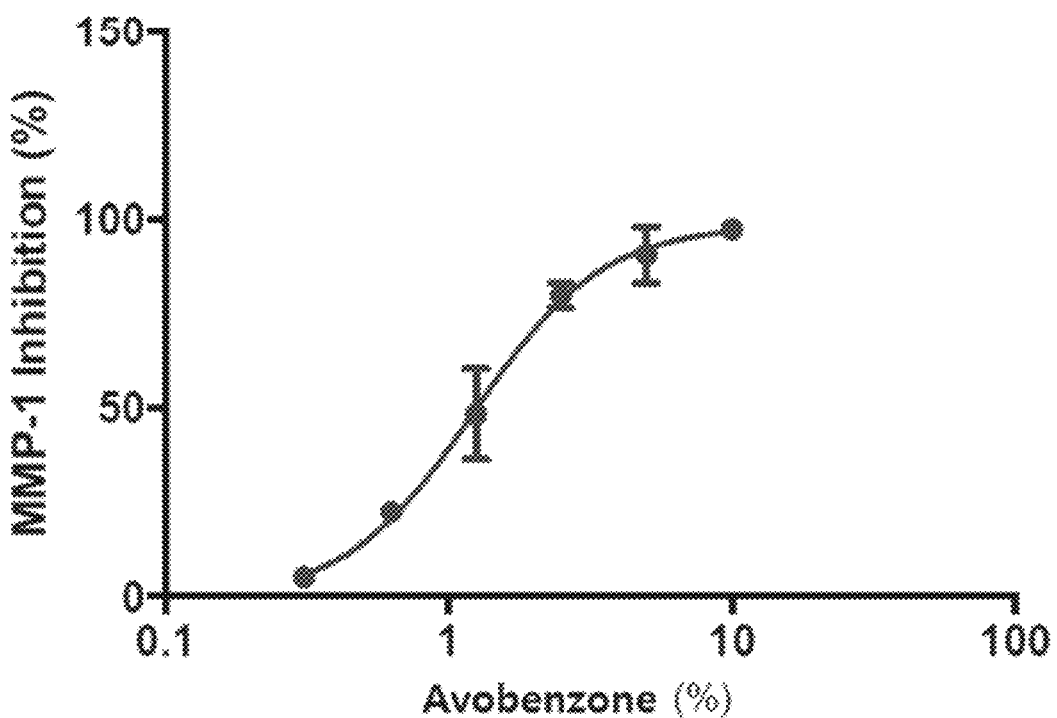
FIG. 22B exhibits the inhibition of MMP-1 by control compound avobenzone.

FIG. 22B exhibits the MMP-1 inhibition of the control compound avobenzone.

An extract derived from sugar cane of the present disclosure demonstrated MMP-1 inhibition activity. At a concentration of 5 mg/mL, an extract derived from sugar cane of the present disclosure has achieved maximum MMP-1 inhibition of 103%. The $EC_{50}$ of the extract was 1.05 mg/mL.

Example 17. Oxygen Radical Absorbance Capacity (ORAC)

Oxygen Radical Absorbance Capacity (ORAC) tests are among the most acknowledged methods that measure antioxidant scavenging activity against oxygen radicals that are known to be involved in the pathogenesis of aging and many common diseases. ORAC 6.0 consists of six types of ORAC assays that evaluate the antioxidant capacity of a material against six primary reactive oxygen species (ROSs, commonly called "oxygen radicals") found in humans: peroxyl radical, hydroxyl radical, superoxide anion, singlet oxygen, peroxynitrite, and hypochlorite. This is a comprehensive panel that evaluates the antioxidant capacity of a material against oxygen radicals.

The ORAC 6.0 tests are based on evaluating the capacity of an interested material to protect a probe (a fluorescent probe or chromagen) from its damage by ROSs. In all ORAC assays, an ROS inducer is introduced to the assay system. The ROS inducer triggers the release of a specific ROS, which would degrade the probe and cause its emission wavelength or intensity change. When an antioxidant material presents in the environment, the antioxidant absorbs the ROS and preserves the probe from degradation. The degree of probe preservation indicates the antioxidant capacity of the material.

An ORAC 6.0 test was performed on human skin cells to determine oxygen radical absorbance capacity of an extract derived from sugar cane of the present disclosure. An ROS inducer was introduced to an ORAC assay system. The ROS inducer triggered release of a specific ROS, which degraded the probe and caused its emission wavelength or intensity change. When an antioxidant material presents in a test sample, the antioxidant absorbs the ROS and preserved the probe from degradation. The degree of probe preservation indicated the antioxidant capacity of the material. Trolox was used as the reference standard. The test results were expressed as μmole Trolox equivalency per millilitre of a test sample.

Table 32 exhibits the results of an ORAC 6.0 test of an extract derived from sugar cane of the present disclosure. The results were expressed as μmole Trolox equivalency (μmole TE) per gram of a tested material.

TABLE 32

ORAC results for an extract derived from sugar cane of the present disclosure

| Analysis | Result | Units |
|---|---|---|
| ORAC against peroxyl radicals | 226.15 | μmole TE/milliliter |
| ORAC against hydroxyl radicals | 1015.09 | μmole TE/milliliter |
| ORAC against peroxynitrite | 11.45 | μmole TE/milliliter |
| ORAC against super oxide anion | 64.88 | μmole TE/milliliter |
| ORAC against singlet oxygen | 163.78 | μmole TE/milliliter |
| ORAC against hypochlorite | 186.92 | μmole TE/milliliter |
| ORAC 6.0 (sum of above) | 1668.27 | μmole TE/milliliter |

TABLE 33

ORAC results for 4 extracts derived from sugar cane of the present disclosure

| | Results | | | |
|---|---|---|---|---|
| Analysis | Extract A | Extract B | Extract C | Extract D |
| ORAC against peroxyl radicals | 303 | 258 | 265 | 2,336 |
| ORAC against hydroxyl radicals | 1,902 | 1,179 | 1,220 | 13,785 |
| ORAC against peroxynitrite | 25 | 32 | 34 | 255 |

TABLE 33-continued

ORAC results for 4 extracts derived from
sugar cane of the present disclosure

| Analysis | Results | | | |
|---|---|---|---|---|
| | Extract A | Extract B | Extract C | Extract D |
| ORAC against super oxide anion | 121 | 82 | 74 | 450 |
| ORAC against singlet oxygen | 348 | 279 | 263 | 2,011 |
| ORAC 5.0 (sum of above) | 2,699 | 1,830 | 1,856 | 18,837 |
| ORAC against hypochlorite | — | 94 | 107 | 620 |
| ORAC 6.0 (sum of above) | — | 1,924 | 1,963 | 19,457 |

The data in Table 33 demonstrates that the extracts of the present disclosure are efficient at scavenging 6 well-characterised and biologically relevant oxidants. The individual ORAC values against each oxidant and the combined total ORAC 6 value demonstrates that the extracts of the present disclosure are powerful antioxidants against a range of oxidant species of biological significance.

Example 18. Cellular Antioxidant Assay (CAA)

CAA analyses the capacity of a material to protect a fluorescent probe (as a marker) from damage by reactive oxygen species (ROS) in intracellular environment.

A CAA was performed to determine cellular antioxidant activity of an extract derived from sugar cane of the present disclosure. In the CAA, peroxyl radical was used as the ROS, and human skin cells was used as the cellular model. Quercetin, a known antioxidant, was used as the standard.

In this CAA, pre-treated human skin cells were incubated with a test sample of an extract derived from sugar cane of the present disclosure and a probe, such as 2',7'-dichlorofluorescin diacetate (DCFH-DA). After incubation for 1 hour, an exogenous source of peroxyl radicals, such as 2,2'-azobis(2-methylpropionamididine) dihydrochloride (ABAP) was added. In the presence of the peroxyl radical, the probe oxidised into a fluorescent product. Fluorescence of the product was monitored with emission at 538 nm and excitation at 485 nm at regular time points to determine the extent of oxidation, and CAA was calculated as follows:

$$CAA\ unit = 100 - (\int A_{sample} \div \int A_{control}) \times 100$$

Wherein, $\int A_{sample}$=integrated area under the fluorescence versus time curve for the test sample, and $\int A_{blank}$=integrated area under the fluorescence versus time curve for the blank.

Cells treated with samples that have antioxidant activity had lower fluorescence compared with cells that were not treated with antioxidants. Quercetin, a known antioxidant, was used as a reference standard, and the results were expressed as µmole quercetin equivalency per gram of the test sample.

Table 34 exhibits the results of CAA of an extract derived from sugar cane of the present disclosure. The results are expressed as µmole quercetin equivalency per gram of a tested material.

TABLE 34

CAA results for an extract derived from
sugar cane of the present disclosure

| Analysis | Result | Units |
|---|---|---|
| CAA | 13.84 | µmole QE/gram |

TABLE 35

CAA results for 5 extracts derived from
sugar cane of the present disclosure

| Sugar cane extract | Results (µmol QE/gram) |
|---|---|
| Extract I | 48.16 |
| Extract II | 56.21 |
| Extract III | 61.37 |
| Extract IV | 67.35 |
| Extract V | 229.12 |

CAA is used to observe the antioxidant capabilities of a substance in a living cellular context, rather than as an abstract chemical reaction. This technique is designed to give a detailed understanding of the mechanisms, bioavailability, uptake, and metabolism of the antioxidant compounds in a cell culture environment that reflects the complexity of a biological system. A high CAA value indicates that an antioxidant compound has been able to enter the cell which indicates bioavailability, without negatively affecting the cell which would indicate toxicity. As a reference, the Kakadu Plum (*Terminalia ferdinandiana*) has been suggested to have the highest Vitamin C concentration of any fruit in the world (Brand et al. 1982). Consequently, it is acknowledged to be an extremely efficient antioxidant. Kakadu Plum has been reported to return a CAA value of 71.5±11.3 QE/gram (Tan et al. 2011). The sugar cane extracts disclosed returned CAA values slightly lower, within or significantly higher than this range. This demonstrates that the sugar cane extracts of the present disclosure provide powerful antioxidant protection in both in vitro and in vivo contexts.

Example 19. Cellular Nrf2 Activation Assay

Cellular Nrf2 activation assay determines the potential of a test material stimulating the production of Nrf2 in human cells. Nrf2 serves as a biomarker for anti-oxidation and anti-inflammatory capacity. Nrf2 is a redox-sensitive transcription factor that binds to antioxidant response elements (ARE) to regulate the expression of antioxidant enzymes that protect against oxidative damage triggered by injury and inflammation. Activation of the Nrf2 pathway has been found to have a wide range of beneficial effects on skin, including reduced rates of skin cancers, protection from ultraviolet radiation, reduced inflammation, irritation and redness, reduction of wrinkles and improvement in skin tone, enhanced barrier function, and improved wound healing.

A cellular Nrf2 activation assay was performed to determine Nrf2 activation potential of an extract derived from sugar cane of the present disclosure. Two batches (replicate 1 and replicate 2) of an extract derived from sugar cane of the present disclosure in a concentration of from 15.625 µg/mL to 500 µg/mL were tested for the ability to activate Nrf2 in human cells.

In order to measure the effect of a test sample of an extract derived from sugar cane of the present disclosure on Nrf2 activity, a reporter gene assay was used. Human cells were transfected with an Nrf2/antioxidant response element (ARE) reporter gene. An ARE reporter comprises of tandem repeats of the ARE transcriptional response element (upstream of firefly luciferase) and a renilla luciferase plasmid under the control of the cytomegalovirus promoter, as an internal control. Transcriptional activity of Nrf2 was determined by measurement of luciferase activities in the transfected human cells as assessed using an appropriate reporter assay kit and a plate reader.

Table 36 exhibits the results of the cellular Nrf2 activation assay of an extract derived from sugar cane of the present disclosure.

TABLE 36

Cellular Nrf2 activation assay results

| Sample Conc. (µg/mL) | Nrf2 pathway activity | | | |
|---|---|---|---|---|
| | Replicate 1 | Replicate 2 | Average | Standard deviation |
| 500 | 73715.08 | 53623.08 | 63669.03 | 14207.189 |
| 250 | 20837.08 | 31168.08 | 26002.58 | 7305.120 |
| 125 | 12246.08 | 6352.08 | 9299.08 | 4167.687 |
| 62.5 | 2279.08 | 3046.08 | 2662.58 | 542.351 |
| 31.25 | 1466.08 | 1247.08 | 1356.58 | 154.856 |
| 15.625 | 1220.08 | 1072.08 | 1146.08 | 104.652 |

Figure 23:
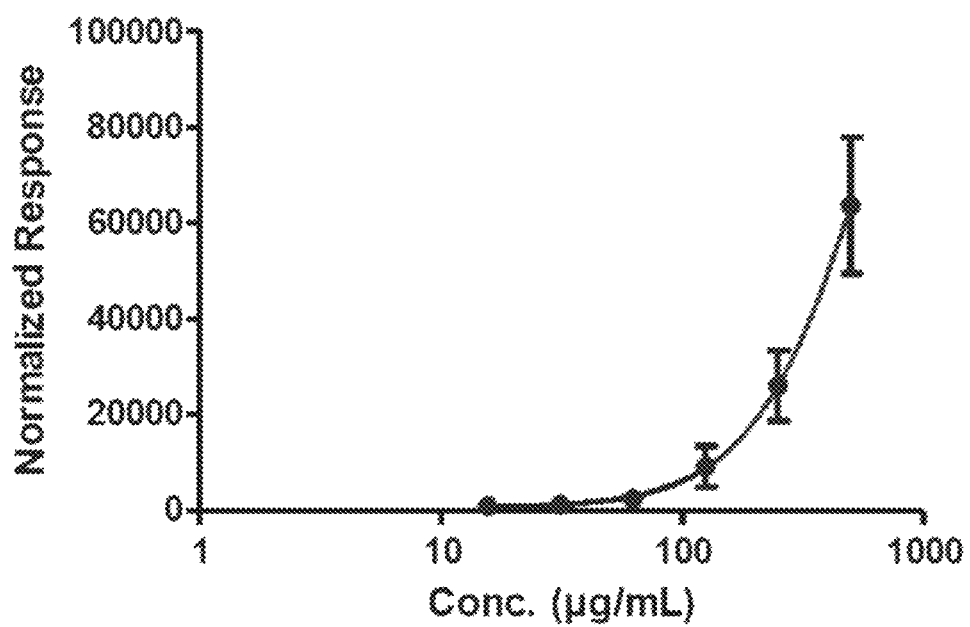
FIG. 23 exhibits the activation of Nrf2 by an extract derived from sugar cane of the present disclosure.

An extract derived from sugar cane of the present disclosure demonstrated Nrf2 activation activity as shown in FIG. 23. At a concentration of 500 µg/mL, an extract derived from sugar cane of the present disclosure has achieved Nrf2 activation of 63669. The $EC_{50}$ of the extract was 631.2 µg/mL. This data demonstrates that the extract derived from sugar cane of the present disclosure activates Nrf2 and therefore has anti-oxidation and anti-inflammatory capacity.

Example 20. Nuclear Factor κB Study

Description

Nuclear Factor κB (NF-κB) is a protein complex that is involved in cellular responses to stimuli such as stress and free radicals, ultraviolet irradiation, oxidized LDL, and bacterial or viral antigens. It plays a key role in regulating the immune response to infection and has been associated with inflammation and plays a major role in the skin aging process. Further, genomic studies have linked psoriasis with mediators in the NF-κB pathway.

Suppression of NF-κB limits the production of pro-inflammatory gene expression and reduces the level of inflammation. Therefore inhibition of NF-κB is used as an indicator of anti-inflammatory activity.

Methodology

The assay of NF-κB inhibition follows a procedure where a test material is absorbed into human cells. A proinflammatory cytokine is then introduced to the human cells to mimic cellular stress, which would normally induce NF-κB activation leading to inflammation. If an NF-κB inhibiting material is present in the cellular environment, the material inhibits NF-κB activation and the degree of inhibition can be monitored via NF-κB expression. NF-κB expression level of the human cells, treated with and without the test material, under the stressed condition are therefore monitored and compared to assess the NF-κB inhibition effect of a material.

Human cells were first treated with or without a representative powdered extract derived from sugar cane of the present disclosure (extract of Example 3) to allow for natural absorption of the extract into the cells. Maximum percentage of NF-κB expression inhibition induced by the powdered extract was reported as with the concentration used that induced the maximum inhibition of NF-κB expression. The half maximal inhibitory concentration ($EC_{50}$) was calculated. Assay results are shown in Table 37.

TABLE 37

Nuclear factor κB activation assay results

| Sugar cane extract of Example 3 | Inhibition (%) | | |
|---|---|---|---|
| Conc. (µg/mL) | Replicate 1 | Replicate 2 | Average |
| 178.13 | 92.04 | 104.19 | 98.12 |
| 89.06 | 66.45 | 76.33 | 71.39 |
| 44.53 | 53.73 | 58.42 | 56.08 |
| 22.27 | 12.37 | 15.49 | 13.93 |
| 11.13 | 7.96 | 14.00 | 10.98 |
| 5.57 | 4.83 | 13.86 | 9.35 |

Figure 24:
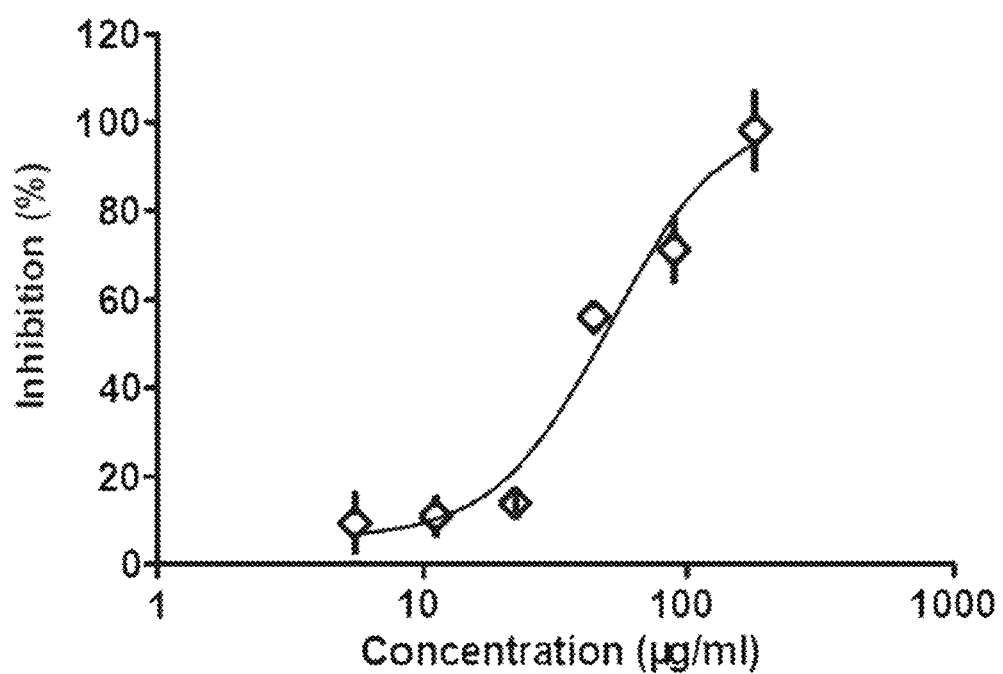
FIG. 24 exhibits a representative binding curve for an extract derived from sugar cane of the disclosure against nuclear factor κB (NF-κB).

The response curve for this data is shown in FIG. 24. A maximum inhibition of 98.12% was observed. The concentration that induced the maximum inhibition was 178 µg/mL. The calculated half-maximal response ($EC_{50}$) was calculated to be 632.1 µg/mL. This data demonstrates that the extract derived from sugar cane of the present disclosure inhibits NF-κB indicating anti-inflammatory activity.

Example 21. TNF-α Study

Description

Tumor necrosis factor (TNF)-α is a pro-inflammatory cytokine (small proteins that impact cell signalling) that triggers downstream cellular feedback loops governing inflammation. TNF-α has been identified as an inflammation trigger and precursor and is released quickly at wound tissues, initiating inflammation. Further, high levels of proinflammatory cytokines, including TNF-α have been detected in psoriatic skin lesions. Thus, TNF-α inhibitors have potential as anti-inflammatory agents for the skin.

Methodology

Human cells are first treated with or without powdered sugar cane extract (extract of Example 3) to allow for natural absorption of the material into the cells. Then, the cells are stressed with an inflammation inducer, which would normally stimulate TNF-α production then further develop into inflammation through series of cellular signalling. If a TNF-α inhibitor presents in the cellular environment, the material inhibits TNF-α production and the degree of inhibition is assessed by level of decreased TNF-α production. TNF-α production level of the human cells, treated with and without a test material, under the stressed condition is monitored and compared to assess the TNF-α inhibition effect of the test material. The maximum percentage of TNF-α expression inhibition induced by the tested sugar cane extracts was reported as was the concentration used that induced the maximum inhibition of TNF-α expression. Assay results are shown in Table 38.

TABLE 38

Cellular TNFα inhibition assay results

| Sugar cane extract of Example 3 | Inhibition (%) | | |
|---|---|---|---|
| Conc. (µg/mL) | Replicate 1 | Replicate 2 | Average |
| 178.13 | 99.20 | 94.80 | 97.00 |
| 89.06 | 92.36 | 92.66 | 92.51 |
| 44.53 | 59.36 | 59.94 | 59.65 |
| 22.27 | 20.00 | 30.35 | 25.18 |
| 11.13 | 13.65 | 10.63 | 12.14 |
| 5.57 | −3.73 | 5.06 | 0.66 |

Figure 25:
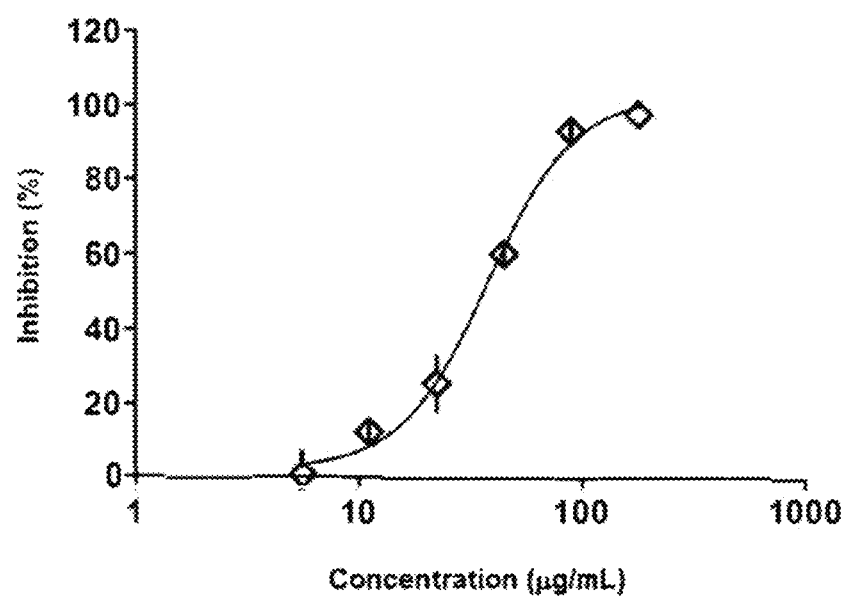
FIG. 25 exhibits a representative binding curve for an extract derived from sugar cane of the disclosure against tumor necrosis factor α (TNF-α).

The response curve for this data is shown in FIG. 25. A maximum inhibition of 97% was observed. The concentration that induced the maximum inhibition was 178 µg/mL. The calculated half-maximal response ($IC_{50}$) was calculated to be 36.31 µg/mL. This data demonstrates that the extract derived from sugar cane of the present disclosure inhibits TNF-α indicating anti-inflammatory activity.

Example 22. Prostaglandin $E_2$ ($PGE_2$) Study

Description $PGE_2$ is a primary product of arachidonic acid metabolism controlled by cyclooxygenase enzymes. It is a potent mediator of inflammation and plays a critical role in increasing vascular permeability, fever generation, tumor growth and wound healing. In particular, $PGE_2$ affects keratinocyte proliferation, differentiation and angiogenesis. Drugs used to inhibit $PGE_2$ synthesis have shown to control inflammation, pain and fever.

Assaying the inhibition of $PGE_2$ expression follows a procedure whereby a test material is absorbed into mammalian cells. Cells are stressed with an inflammation inducer, which would normally stimulate $PGE_2$ production that would further develop into inflammation through series of cellular signalling. However, if a $PGE_2$ inhibitor is presents in the cellular environment, the material inhibits $PGE_2$ production and the degree of inhibition is assessed by level of decreased $PGE_2$ production. $PGE_2$ production level in cells, treated with and without a test material, under the stressed condition is monitored and compared to assess the $PGE_2$ inhibition effect of the test material.

Methodology

Mammalian cells were first treated with or without powdered sugar cane extract (extract of Example 3) to allow for natural absorption of the material into the cells. The maximum percentage of $PGE_2$ expression inhibition induced by the powdered extract and the concentration used that induced the maximum inhibition of $PGE_2$ expression were reported. The half maximal effective concentration ($EC_{50}$) was calculated. The assay results are shown in Table 39.

TABLE 39

Cellular PGE2 inhibition assay results

| Conc. of powdered sugar cane extract of Example 3 (µg/mL) | Inhibition of PGE2 (%) |
|---|---|
| 183.13 | 58.29 |
| 91.56 | 44.08 |
| 45.78 | 45.72 |

TABLE 39-continued

Cellular PGE2 inhibition assay results

| Conc. of powdered sugar cane extract of Example 3 (µg/mL) | Inhibition of PGE2 (%) |
|---|---|
| 22.89 | 30.97 |
| 11.45 | 24.41 |
| 5.72 | −8.38 |

Figure 26:
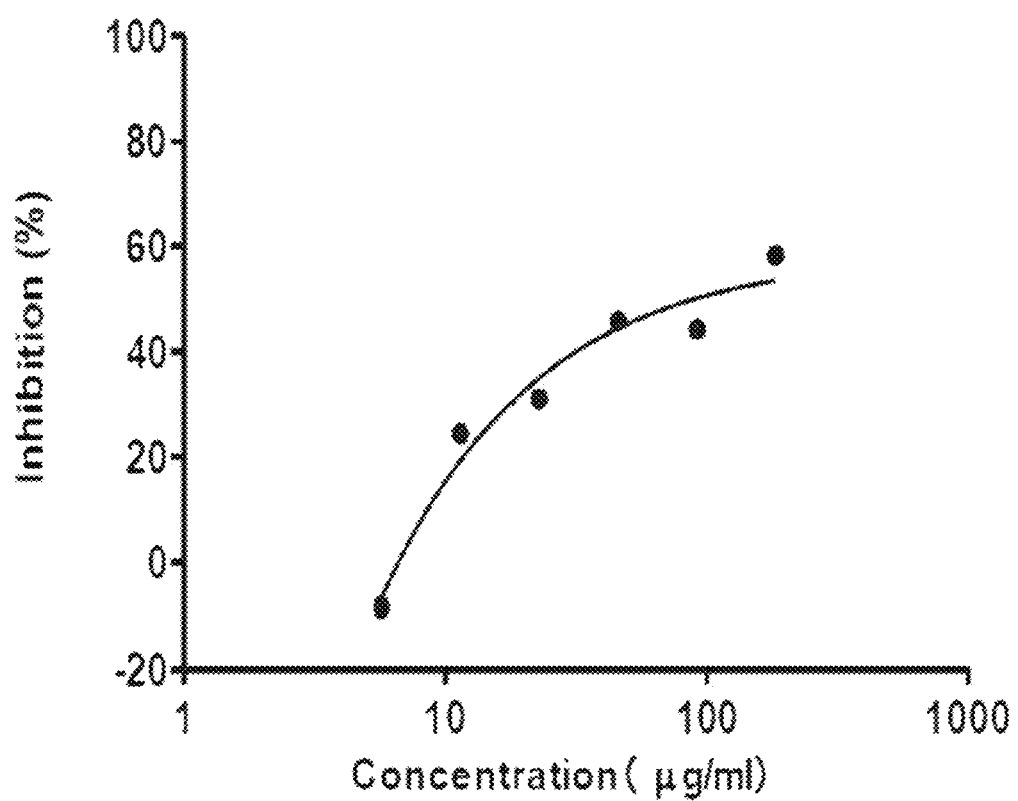
FIG. 26 exhibits a representative inhibition curve for an extract derived from sugar cane of the disclosure against prostaglandin E2 ($PGE_2$).

The response curve for this data is shown in FIG. 26. A maximum inhibition of 58.29% was observed. The concentration that induced the maximum inhibition was 183.13 µg/mL. The calculated half-maximal response ($IC_{50}$) was calculated to be 91.62 µg/mL. This data demonstrates that the extract derived from sugar cane of the present disclosure inhibits $PGE_2$ indicating anti-inflammatory activity.

Example 23. Cyclooxygenases-1 (COX-1) and Cyclooxygenases-2 (COX-2) Inhibition Assays Description Cyclooxygenases-1 (COX-1) inhibitors are among the important targets for treatment of inflammation related diseases. COX has two well-known isoforms, COX-1 and COX-2, which are similar in their amino-acid sequences and identity. COX-2 predominates at sites of inflammation and is involved in chronic inflammation observed in chronic lesions.

Methodology

COX-1 and COX-2 inhibition assays were used to assess the inhibition capability of representative powdered extracts derived from sugar cane of the present disclosure (extract of Example 3) by monitoring the extracts' impact on the activity of a specific COX enzyme. The assays compare the enzymatic activity of the target COX in the presence with and without the material of interest to determine the inhibition potential of the material. The results were expressed as the concentration of the tested material used to achieve 50% of COX inhibition ($IC_{50}$), if 50% of inhibition has been achieved. If the $IC_{50}$ value could not be calculated, the maximum percentage of COX inhibition achieved, and the concentration of the material used that induced the maximum inhibition were reported. COX-1 and COX-2 results are shown in Table 40 and Table 41 respectively.

TABLE 40

COX-1 assay results
COX-1 inhibition (%)

| Conc. (µg/mL) | Replicate 1 | Replicate 2 | Average | Standard deviation |
|---|---|---|---|---|
| 500.00 | 16.73 | 6.62 | 11.68 | 7.15 |
| 250.00 | −3.67 | 4.83 | 0.58 | 6.01 |
| 125.00 | 5.73 | −5.65 | 0.04 | 8.05 |
| 62.50 | 1.14 | 10.11 | 5.63 | 6.35 |
| 31.25 | 4.83 | 6.62 | 5.72 | 1.27 |
| 15.63 | 8.38 | 3.92 | 6.15 | 3.16 |

Figure 27A:
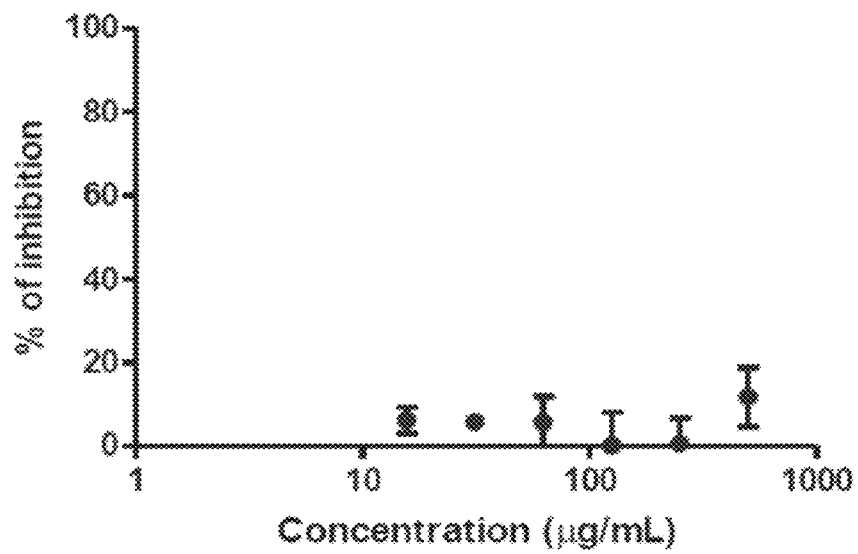
FIG. 27A exhibits representative inhibition curves for an extract derived from sugar cane of the disclosure against cyclooxygenase-1 (COX-1), FIG. 27B exhibits representative inhibition curves for an extract derived from sugar cane of the disclosure against cyclooxygenase-2 (COX-2).

The inhibition curve for the COX-1 data is shown in FIG. 27A. The maximum inhibition is 11.68% and the calculated effective concentration at maximum inhibition is 500.00 µg/mL.

TABLE 41

COX-2 assay results
COX-2 inhibition (%)

| Conc. (µg/mL) | Replicate 1 | Replicate 2 | Average | Standard deviation |
| --- | --- | --- | --- | --- |
| 500.00 | 46.52 | 44.98 | 45.70 | 1.02 |
| 250.00 | 25.78 | 30.20 | 27.99 | 3.13 |
| 125.00 | 18.97 | 26.43 | 22.70 | 5.27 |
| 62.50 | 11.56 | 9.99 | 10.78 | 1.10 |
| 31.25 | 13.09 | 9.99 | 11.54 | 2.19 |
| 15.63 | 9.20 | 6.79 | 8.00 | 1.71 |

Figure 27B:
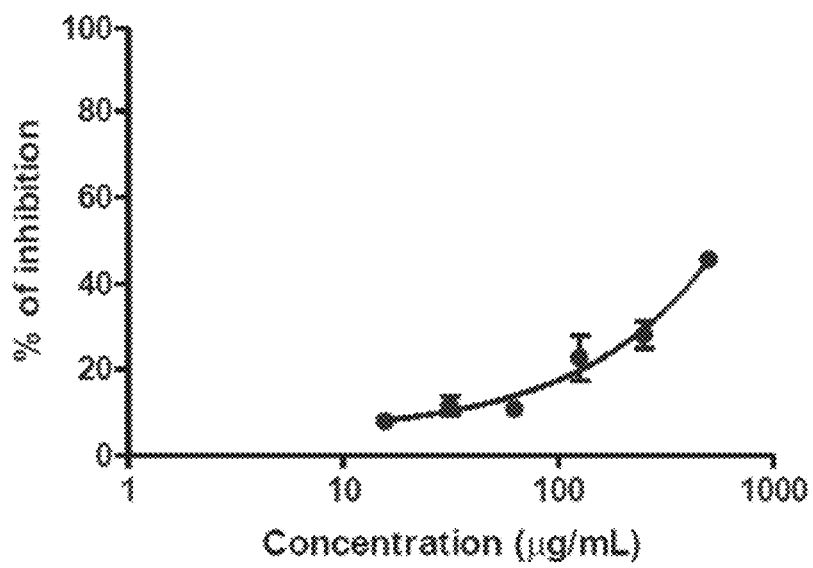

The inhibition curve for the COX-2 data is shown in FIG. 27B. The maximum inhibition was observed to be 47.70%. The calculated effective concentration at maximum inhibition was 500.00 µg/mL.

This demonstrates that the extract of sugar cane of the present disclosure was selective for COX-2 over COX-1. Further, this data demonstrates that the extract derived from sugar cane of the present disclosure inhibits COX-2 indicating anti-inflammatory activity.

Example 24. Inhibitory Effect of the Extracts on Microbial Growth

As described above, a variety of pathogenic microorganisms thrive in the skin. To measure the inhibitory potential of an extract derived from sugar cane of the present disclosure on microorganisms, a sample of an extract derived from sugar cane of the present disclosure was tested for its effectiveness as an anti-bacterial agent.

Bacterial Strains and Materials

Bacterial strains, *Staphylococcus aureus* ATC® 25923, *Staphylococcus epidermidis* ATC® 14990, *Streptococcus mutans* ATC® 25175 and *Escherichia coli* ATC® 25922 were purchased from In Vitro Technologies (Noble Park, VIC Australia). *Propionibacterium acnes* ATCC® 6919 was ordered from Thermo Scientific™ Culti-Loops™ (Waltham, MA USA). Tryptone soya agar with 5% horse blood plates, and, tryptone soya broth were purchased from Thermo Scientific™. Petri dishes (90×15 mm), loop inoculating PS blue, anaerobic jars (2.5 Litre) and anaerobic Gen Sachets were purchased from Thermo Scientific™. Penicillin-streptomycin was obtained from Sigma Aldrich (Castle Hill, NSW Australia).

Culturing and Growth Conditions

All strains used were in freeze dried form and transferred into enrichment sterilized tryptone soya broth (TSB) media. The cultures were propagated 3 times to optimize growth at 37° C. and at different incubation times, depending on the strain type; *Escherichia coli* was incubated for 24 hours (h), *Staphylococcus aureus*, *Staphylococcus epidermidis* and *Streptococcus mutans* were incubated for 48 h, and *Propionibacterium acnes* for 72 h. *Propionibacterium acnes* (loop form) was ready to culture directly into blood agar. There were no differences in the preparation of agar plates for disc and well diffusion assays. Briefly, 100 µL of a bacterial suspension was added into 6 mm wells/discs of tryptone soya agar plates with 5% horse blood (TSAB).

Extract Derived from Sugar Cane and Control Solutions

The extract derived from sugar cane was prepared according to the process of FIG. 1.

Stock solutions of the extract were prepared as previously described (Taguri et al., 2004) with small modifications. Briefly, the extract powder was dissolved in sterilized water and filtered through Advantec cellulose acetate filters (0.2 mm pore size; 25 mm diameter). The range of concentrations of extract solution was serially diluted in 14 stages (0.1, 0.5, 0.7, 0.8, 1, 2, 3, 4, 5, 6, 7, 8, 9, 10 mg/ml). The negative control used was sterilized water and the positive control was penicillin-streptomycin (consisting of 10,000 units/ml penicillin G sodium salt and 10 mg/ml streptomycin sulfate).

Antimicrobial Activity of the Extract

Antibacterial tests were carried out using the Oxford cup assay with minor modifications (Shang et al., 2014). After autoclaving, TSB media was cooled to 50° C. Susceptibility of the test organism to the extract was determined by employing the standard disk or well diffusion technique. Wells 6 mm in diameter were made in TSAB plates. The bacterial suspension in TSB was spread and plated on blood agar media. For the disk diffusion test, sterile paper discs (6 mm) were added of the test sample (100 µl) and placed onto the inoculated blood agar surface. After cultivation at 37° C. for (24, 48 or 72 h) under anaerobic conditions in an anaerobic jar containing AnaeroGen sachets to maintain anaerobic conditions, the resulting inhibition zone diameters were measured. Using the well (6 mm) diffusion technique, 100 µl/well of the sample was added and the size of the inhibition zone of growth was measured after 24 h or 48 h at 37° C. All experiments were repeated for each bacterial strain at least 3 times.

Statistical Analysis

Analysis of data (one-way ANOVA) was used to determine any significant differences ($p<0.05$) in the diameter of the inhibition zones, using Minitab 17 software. All data are expressed as the mean of triplicate±standard deviation.

The Extract Inhibits Growth of *Escherichia coli*

*Escherichia coli* is a gram-negative anaerobic bacteria mostly found in the intestine. Most strains of *Escherichia coli* are harmless and constitute part of the normal gut flora and are involved in vitamin K synthesis. However, some *Escherichia coli* serotypes are often responsible for food poisoning and disease (i.e. gastroenteritis, hemorrhagic colitis, Crohn's disease, travellers' diarrhea, urinary tract infections, sepsis, pneumonia) and wound infections. Antibiotics are used to treat *Escherichia coli* infections and to decrease the course of illness, though, the rate of bacterial resistance to commonly used antibiotics is increasing and antibiotics are more commonly not recommended.

Figure 28A:
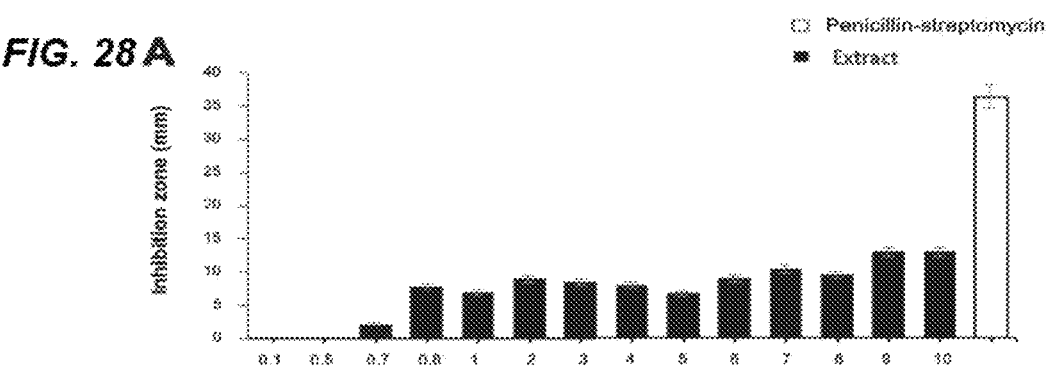
FIGS. 28A, 28B, 28C, 28D, and 28E exhibit the antibacterial efficacy testing of the sugar cane extracts of the present disclosure at different concentrations (0.1-10 mg/ml) (black bars) against the growth of (FIG. 28A) *Escherichia coli*, (FIG. 28B) *Staphylococcus epidermidis*, (FIG. 28C) *Staphylococcus aureus*, (FIG. 28D) *Staphylococcus mutans* and (FIG. 28E) *Propionibacterium acnes*, in blood agar following 24-72 h incubation at 37° C. Positive control penicillin-streptomycin is shown as white bars. Error bars represent standard deviation of the means, using well and disc methods.
Figure 29A:
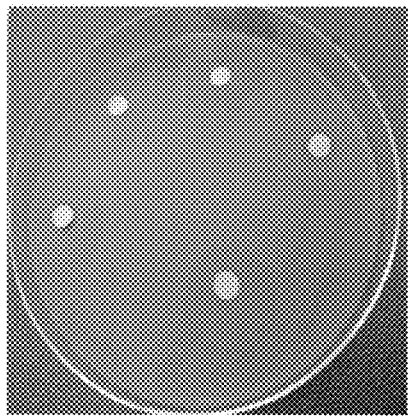
FIGS. 29A, 29B, 29C, 29D, 29E and 29F exhibit representative examples of bacterial growth zones of inhibition caused by different concentrations of the sugar cane extracts of the present disclosure (0.1-10 mg/ml) on tryptone soya blood agar plates; disc or well methods are shown. Inhibition by sugar cane extracts of the present disclosure for (FIG. 29A) *Escherichia coli*, (FIG. 29B) *Staphylococcus epidermidis*, (FIG. 29C) *Staphylococcus aureus*, (FIG. 29D) *Staphylococcus mutans*, (FIG. 29E) *Propionibacterium acnes* and (FIG. 29F) Bacterial growth inhibition in the presence of penicillin-streptomycin.

Growth of *Escherichia coli* was evaluated in TSAB plates containing a series of wells/discs loaded with a range of concentrations of the extract at 37° C. following 24 h incubation period. The diameters of the inhibition zone around the wells/discs increased gradually with increasing concentrations of the extract, starting at 0.7 mg/ml and up to 10 mg/ml ($p<0.05$, compared to negative control). The lowest growth inhibition zone was 1.5 mm with at 0.7 mg/ml concentration of the extract whilst the highest inhibition zone was 10.6 mm at concentrations 9 mg/ml and 10 mg/ml (FIGS. 28A and 29A). The inhibition zone of the positive control penicillin-streptomycin reached 35 mm and the negative control showed no inhibition zone.

The Extract Inhibits Growth of *Staphylococcus epidermidis*

*Staphylococcus epidermidis* is a gram-positive anaerobic bacterium part of the normal skin flora which is non-pathogenic although those with compromised immune systems are at risk of developing infection. In addition, *Staphylococcus epidermidis* is commonly hospital acquired infection, in addition to drug users and those patients needing catheters and prosthetic heat valves; hand washing has been used in hospitals to reduce *Staphylococcus epidermidis* contamination and spread. Due to it being part of the normal skin flora, *Staphylococcus epidermidis* has developed resistance to commonly used antibiotics. Of interest, *Staphylococcus epidermidis* is often present in affected acne vulgaris pores together with *Propionibacterium acnes*.

Figure 28B:
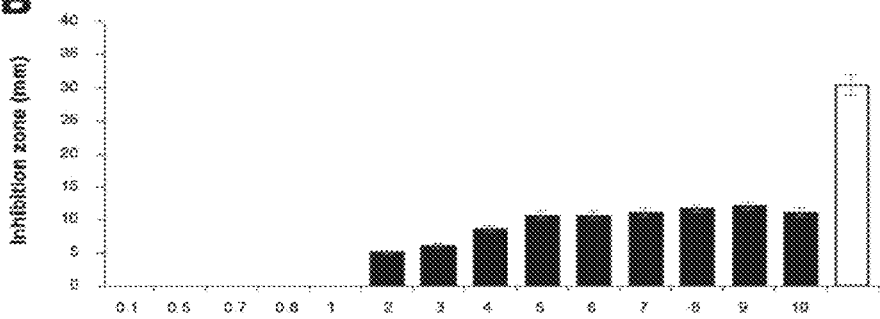
Figure 29B:
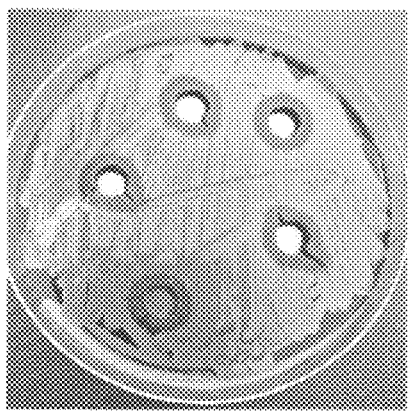

*Staphylococcus epidermidis* was grown on TSAB plates containing a series of wells loaded with a fixed amount of the extract (100 µl/well or disc) with increasing concentrations of the extract from 0.1-10 mg/ml. After 48 h of incubation at 37° C., the diameters of the growth inhibition zone were measured. In general, the inhibition zone diameters gradually increased from 5 mm to 10.4 mm between 2-5 mg/ml (p<0.05) after which there was a plateau from 5-10 mg/ml concentration of the extract (FIGS. 28B, 29B). The inhibition zone of the positive control penicillin-streptomycin reached 30 mm and the negative control and doses of the extract less than 2 mg/ml showed no inhibition zones.

The Extract Inhibits Growth of *Staphylococcus aureus*

*Staphylococcus aureus* (gram-positive bacterium) part of the normal flora of the skin, nose and respiratory tract, is not commonly pathogenic but can cause minor to severe life threatening infections. *Staphylococcus aureus* infects wounds and causes impetigo and septicaemia. With the emergence of antibiotic resistant *Staphylococcus aureus* strains this has become a problem worldwide and accounts up to 50,000 deaths each year in the USA alone.

Figure 28C:
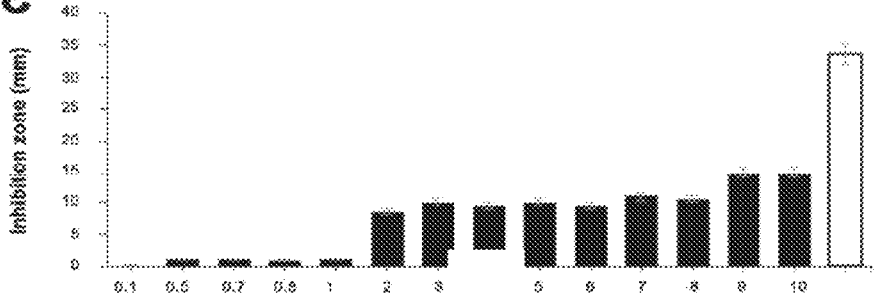
Figure 29C:
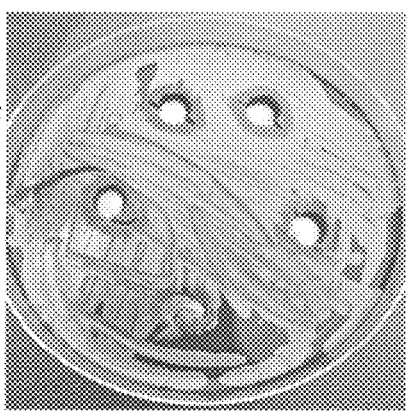

*Staphylococcus aureus* was cultured for 48 h on TSAB plates at 37° C. with a series of wells/discs containing different concentrations of the extract. Antibacterial activity at varying concentrations are shown in FIG. 28C. The diameters of bacterial growth inhibition zones around the wells/discs were clearly inhibited between 2-10 mg/ml of the extract, with weak and unclear inhibition between 0.5-1 mg/ml concentrations of the extract. There were no significant differences in zone inhibition between concentration 2-8 mg/ml but were significant compared to 0.5-1 mg/ml concentrations (p<0.05). The highest diameters of *Staphylococcus aureus* growth inhibition zones were at concentration 9-10 mg/ml of approximately 10.8 mm which was significantly higher than that at <8 mg/ml (p<0.05) (FIGS. 28C and 29C). The inhibition zone of the positive control penicillin-streptomycin reached 35 mm and the negative control and doses of the extract less than 0.5 mg/ml showed no inhibition zones.

The Extract Inhibits Growth of *Streptococcus mutans*

*Streptococcus mutans* (gram positive anaerobic bacterium) mostly found in the oral cavity plays a crucial role in tooth decay, oral diseases and certain cardiovascular diseases. *Streptococcus mutans* are also part of the normal oral flora in humans and in canines and contribute to infections of wounds caused by bites. Increased use of fluoride based toothpastes and oral rinses in recent years in order to decrease *Streptococcus mutans* growth has resulted in the emergence of *Streptococcus mutans* resistant strains.

Figure 28D:
Figure 29D:
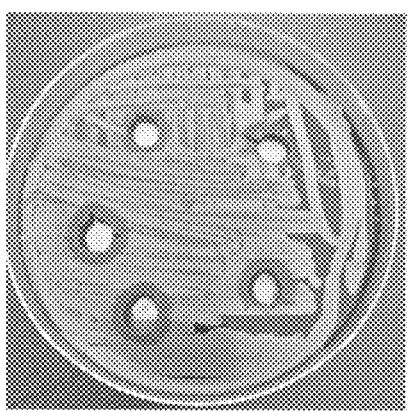

*Streptococcus mutans* was added to wells in TSAB plates at 37° C. for 48 h. When inhibition zones were examined in relation to a range of concentrations of the extract, no *Streptococcus mutans* bacterial inhibition zones were observed at concentrations less than 6 mg/ml. However, at concentrations between 7-10 mg/ml of the extract, significant inhibition zones were noted (p<0.05) with concentrations 9-10 mg/ml being most significant of about 15 mm (FIGS. 28D and 29D). In comparison to positive control penicillin-streptomycin the bacterial inhibition zone was 30 mm and the negative control and doses of the extract less than 7 mg/ml showed no inhibition zones.

The Extract Inhibits Growth of *Propionibacterium acnes*

*Propionibacterium acnes*, also a gram-positive anaerobic bacterium is closely linked to acne, blepharitis and atopic dermatitis, and is susceptible to a vast number of antibiotics, natural anti-microbials (i.e. tea tree oil, citrus oil, honey) and over the counter anti-bacterial chemicals. However, in recent years there has been an emergence of antibiotic resistant *Propionibacterium acnes* strains which has resulted in a problem worldwide.

Figure 28E:
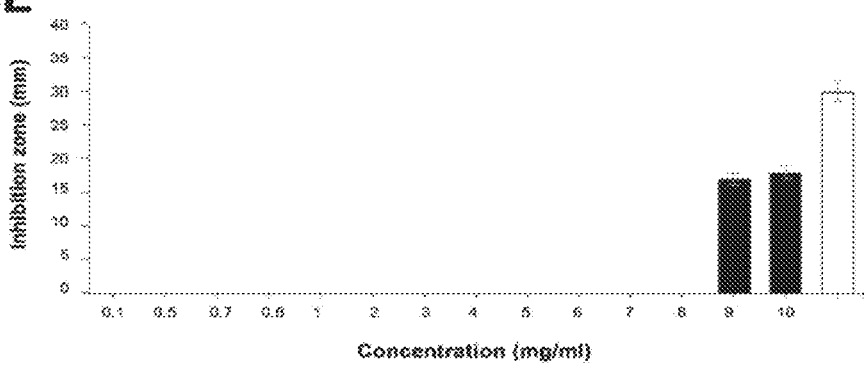
Figure 29E:
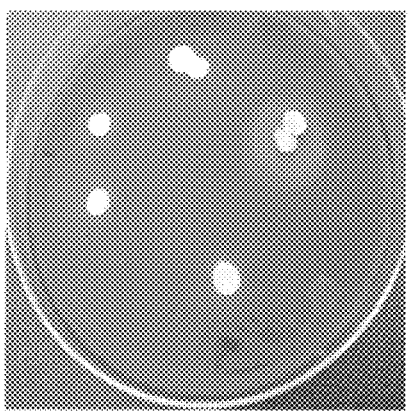
Figure 29F:
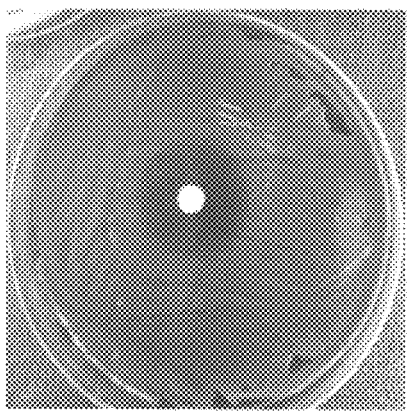

The anti-bacterial growth of *Propionibacterium acnes* in the presence of different concentrations of the extract was examined at 37° C. and 72 h of incubation. Zones of inhibition showed that concentrations of the extract had good growth inhibition activity (17-18 mm) only at concentrations 9-10 mg/ml (FIGS. 28E and 29E). The inhibition zone of the positive control penicillin-streptomycin (FIG. 29F) was in the order of 30 mm and the negative control and doses of the extract less than 9 mg/ml showed no inhibition zones.

Example 25

Example 25 provides illustrative and non-limiting examples of compositions comprising extracts derived from sugar cane of the present disclosure.

| Hand cream | |
|---|---|
| Ingredient | Ingredient Quantity |
| Vegesorb Cream Base* (ex. Vegesorb) | 948.250 grams |
| Extract derived from sugar cane of the present disclosure | 50.000 grams |
| White Peony Fragrance (ex. ABP (Perfumis)) | 1.750 grams |

*Vegesorb Cream Base contains purified water, Glycerin (plant derived), glyceryl monosterate (plant derived), almond oil (plant derived), apricot oil (plant derived), PEG-20 sterate (plant derived), cetostearyl alcohol (plant derived), stearic acid (plant derived), cetostearyl octanoate (plant derived), Vitamin E (plant derived), phenoxyethanol (purpose designed water soluble preservative), diazolidinylurea (purpose designed water soluble preservative), methyl hydroxybenzoate (purpose designed water soluble preservative).

The hand cream contains 5% of an extract derived from sugar cane of the present disclosure.

The hand cream was prepared by the following method:
1. Add the Vegesorb base to main vessel;
2. Add the extract derived from sugar cane and mix well;
3. Add the White Peony fragrance and mix well; and
4. Pack in appropriate packaging.

| Face cream | |
|---|---|
| Ingredient | Ingredient Quantity |
| Vegesorb Cream Base* (ex. Vegesorb) | 948.500 grams |
| Extract derived from sugar cane of the present disclosure | 50.000 grams |
| Lily of the Valley Fragrance (ex. ABP Perfumis) | 1.500 grams |

*Vegesorb Cream Base contains purified water, Glycerin (plant derived), glyceryl monosterate (plant derived), almond oil (plant derived), apricot oil (plant derived), PEG-20 sterate (plant derived), cetostearyl alcohol (plant derived), stearic acid (plant derived), cetostearyl octanoate (plant derived), Vitamin E (plant derived), phenoxyethanol (purpose designed water soluble preservative), diazolidinylurea (purpose designed water soluble preservative), methyl hydroxybenzoate (purpose designed water soluble preservative).

The face cream contains 5% of an extract derived from sugar cane of the present disclosure.

The face cream was prepared by the following method:
1. Add the Vegesorb base to main vessel;
2. Add the extract derived from sugar cane and mix well;
3. Add the Lilly of the Valley fragrance and mix well; and
4. Pack in appropriate packaging.

Frangipani face cream

| Ingredient | Ingredient Quantity (%) |
| --- | --- |
| Frangipani Fragrance | 0.15 |
| Extract derived from sugar cane of the present disclosure | 5.0 |
| Vegesorb Cream Base* | 94.85 |

*Vegesorb Cream Base contains purified water, Glycerin (plant derived), glyceryl monosterate (plant derived), almond oil (plant derived), apricot oil (plant derived), PEG-20 sterate (plant derived), cetostearyl alcohol (plant derived), stearic acid (plant derived), cetostearyl octanoate (plant derived), Vitamin E (plant derived), phenoxyethanol (purpose designed water soluble preservative), diazolidinylurea (purpose designed water soluble preservative), methyl hydroxybenzoate (purpose designed water soluble preservative).

The face cream was prepared using a similar method to that described above.

BB face cream

| Ingredient | Ingredient Quantity (%) |
| --- | --- |
| Extract derived from sugar cane of the present disclosure | 2.0 |
| Medium skin tone BB cream* | 94.85 |

*BB Cream contains water, dimethicone, glycerin, prunus armeniaca kernel oil/apricot kernel oil, oryza sativa bran oil/ricebran oil, propanediol, ethylhexyl methoxycinnamate, stearic acid, butyrospermum parkii butter/shea butter, palmitic acid, peg-100 stearate, glyceryl stearate, peg-20 stearate, stearyl alcohol, cera alba/beeswax, acrylamide/sodiumacryloyldimethyltaurate copolymer, phenoxyethanol, parfum/fragrance, tocopheryl acetate, isohexadecane, hydroxypropyltetrahydropyrantriol, caprylyl glycol, propylene glycol, dimethiconol, vigna aconitifolia/vigna aconitifolia seed extract, polysorbate 80, pentaerythrityl tetra-di-t-butyl hydroxyhydrocinnamate, sodium cocoyl glutamate, disodium edta, hydrolyzed soyprotein, linalool, benzyl salicylate, limonene, cinnamic acid, phloroglucinol trimethyl ether, benzyl alcohol, geraniol, citral, titanium dioxide and iron oxides.

The face cream was prepared using a similar method to that described above.

Face mask

| Ingredient | Ingredient Quantity (%) |
| --- | --- |
| Facial Serum Base* | 69.75 |
| Chamomile Floral Water | 25 |
| Extract derived from sugar cane of the present disclosure | 5 |
| Pink Grapefruit Fragrance | 0.25 |

*Facial Serum Base contains purified water, glycerine, aloe vera leaf juice, xanthan gum, phenoxyethanol, butylene glycol, caprylyl glycol, polysorbate 20, hydrolyzed marine collagen, carbomer, triethanolamine, rosehip oil, evening primrose oil, jojoba oil, apple fruit extract, melon fruit extract, sorbitol, ethylhexylglycerin, beta-glucan, potassium sorbate, sodium benzoate, portulaca extract, seaweed extract, green tea leaf extract, citric acid, 1,2-hexanediol, grapefruit seed extract, benzoic acid, Vitamin C.

The face mask was prepared using a similar method to that described above.

Aloe Vera soap

| Ingredient | Ingredient Quantity |
| --- | --- |
| Aloe Vera Natural Melt & Pour Soap Base* (ex. Aussie Soap Supplies) | 965.00 grams |
| Extract derived from sugar cane of the present disclosure | 25.000 grams |
| Wildflower Honey Fragrance (ex. Aussie Soap Supplies) | 10.00 grams |

*Aloe Vera Natural Melt & Pour Soap Base contains coconut oil, palm oil, safflower oil, glycerine (Kosher, of vegetable origin), aloe vera gel, purified water, sodium hydroxide, sorbitol, propylene glycol (made from vegetable glycerine), sorbitan oleate, oat protein.

The soap contains 2.5% of an extract derived from sugar cane of the present disclosure.

The soap was prepared by the following method:
1. Weigh the required amount of soap and gently melt;
2. Once Soap is melted, add the extract derived from sugar cane and Fragrance, slowly mix, but do not let boil;
3. Pour into selected moulds, and set at ambient temp. Do not move while base is resetting; and
4. Remove from mould. Cut to selected size and wrap.

Wildflower and honey soap

| Ingredient | Ingredient Quantity (%) |
| --- | --- |
| Frangipani Fragrance | 1.0 |
| Extract derived from sugar cane of the present disclosure | 2.5 |
| Aloe vera soap base* | 96.5 |

*Aloe Vera Soap Base contains coconut oil, palm oil, safflower oil, glycerine (Kosher, of vegetable origin), aloe vera gel, purified water, sodium hydroxide, sorbitol, propylene glycol (made from vegetable glycerine), sorbitan oleate, oat protein.

The soap was prepared using a similar method to that described above.

After sun care lotion

| Ingredient | Ingredient Quantity |
| --- | --- |
| Aloe Vera Gel Base* (ex. New Directions) | 873.950 grams |
| Extract derived from sugar cane of the present disclosure | 25.000 grams |
| 50:50 Xanthan:Acacia Blend | 0.0500 grams |
| Glycerine | 100.000 grams |
| Aloe and Cucumber Fragrance (ex. ABP Perfumis) | 1.000 grams |

*Aloe Vera Gel Base contains water, phenoxyethanol, Carbomer, ethylhexylglycerin, sodium hydroxide, glycerin, aloe barbadensis leaf juice powder, disodium EDTA.

The after sun care lotion contains 2.5% of an extract derived from sugar cane of the present disclosure.

The after sun care lotion was prepared by the following method:
1. Weigh the Aloe Vera Gel Base;
2. Add Glycerine to the base and mix well;
3. Add the extract derived from sugar cane to the mix and mix well;
4. Add xanthan and acacia blend to the blend and mix well until the product thickens;
5. Add fragrance to the base mix well; and
6. Pack into appropriate packaging.

Shower gel

| Ingredient | Ingredient Quantity |
| --- | --- |
| Hand and Body Wash Base* (ex. Aussie Soap Supplies) | 941.300 grams |
| Extract derived from sugar cane of the present disclosure | 30.000 grams |
| Energy Fragrance (ex. Aussie Soap Supplies) | 28.700 grams |

*Hand and Body Wash Base contains aqua, organic potassium cocoate, organic potassium oleate, lauryl betaine, organic glycerine from organic sunflower oil, benzyl alcohol, decyl glucoside, potassium citrate.
The shower gel contains 3% of an extract derived from sugar cane of the present disclosure.

The shower gel was prepared by the following method:
1. Add the unscented Hand and Body Wash Base to main vessel;
2. Add the extract derived from sugar cane and mix well.
3.3 Add the fragrance and mix well.
3.4 Pack in to appropriate packaging.

| Lemon Verbena Shower gel | |
|---|---|
| Ingredient | Ingredient Quantity (%) |
| Lemon Verbena Fragrance | 2.87 |
| Extract derived from sugar cane of the present disclosure | 3.0 |
| Shower Gel Base* | 94.13 |

*Shower Gel Base contains aqua, organic potassium cocoate, organic potassium oleate, lauryl betaine, organic glycerine from organic sunflower oil, benzyl alcohol, decyl glucoside, potassium citrate.

The shower gel was prepared using a similar method to that described above.

| Energy Shower gel | |
|---|---|
| Ingredient | Ingredient Quantity (%) |
| Energy Fragrance | 2.87 |
| Extract derived from sugar cane of the present disclosure | 3.0 |
| Shower Gel Base* | 94.13 |

*Shower Gel Base contains aqua, organic potassium cocoate, organic potassium oleate, lauryl betaine, organic glycerine from organic sunflower oil, benzyl alcohol, decyl glucoside, potassium citrate.

The shower gel was prepared using a similar method to that described above.

| Shampoo—conditioning | |
|---|---|
| Ingredient | Ingredient Quantity |
| Shampoo—Conditioning Base* (ex. Aussie Soap Supplies) | 973.00 grams |
| Extract derived from sugar cane of the present disclosure | 25.000 grams |
| Bamboo and Lily Fragrance (ex. ABP Perfumis) | 2.000 grams |

*Shampoo—Conditioning Base contains aqua, sodium lauroyl methyl isethionate, cocamidopropyl betaine, lauryl glucoside, sodium chloride, sodium methyl isethionate, phenoxyethanol, sodium lauroyl isethionate, sodium benzoate, trisodium sulfosuccinate, polyquaternium 10, lauric acid, zinc dilaurate, trisodium ethylenediamine disuccinate, sodium laurate.

The shampoo—conditioning contains 2.5% of an extract derived from sugar cane of the present disclosure.

The shampoo—conditioning was prepared by the following method:
1. Add the Unscented Shampoo—Conditioning base to main vessel;
2. Add the extract derived from sugar cane and mix well;
3. Add the fragrance and mix well; and
4. Pack in to appropriate packaging.

| Dual action extra strength heat gel | |
|---|---|
| Ingredient | Ingredient Quantity (%) |
| Dencorub base | 95 |
| Extract derived from sugar cane of the present disclosure | 5.0 |

The heat gel was prepared using a similar method to that described above.

| Face cream |
|---|
| Ingredient |
| Extract derived from sugar cane of the present disclosure aqua |
| cetearyl alcohol |
| cetyl alcohol |
| glycerin |
| α-arbutin |
| ceteareth-20 |
| isononyl isononanoate |
| phenoxy ethanol |
| niacinamide |
| tocopheryl acetate |
| disodium EDTA |
| BHT |

It will be appreciated by one of ordinary skill in the art that numerous variations and/or modifications may be made to the above-described embodiments, without departing from the broad general scope of the present disclosure. The present embodiments are, therefore, to be considered in all respects as illustrative and not restrictive.

REFERENCES

Brand, J. C, Cherikoff, V. and Lee, A. (1982). An Outstanding Food Source of Vitamin C. Lancet 2(8303):873.
Physicians' Desk Reference (PDR).
Remington's Pharmaceutical Sciences, Mack Publishing Co., Easton Pa., 22$^{nd}$ edition, 2012.
Shang, R. F., Wang, G. H., Xu, X. M., Liu, S. J., Zhang, C., Yi, Y. P., Liu, Y. (2014). Synthesis and biological evaluation of new pleuromutilin derivatives as antibacterial agents. Molecules, 19(11), 19050-19065. doi: 10.3390/molecules191119050.
Taguri, T., Tanaka, T., & Kouno, I. (2004). Antimicrobial Activity of 10 Different Plant Polyphenols against Bacteria Causing Food-Borne Disease. Biological and Pharmaceutical Bulletin, 27(12), 1965-1969. doi: 10.1248/bpb.27.1965.
Tan, A. C., Konzac, I., Ramzan, I., Zabaras D., Sze D. M. (2011). Potential antioxidant, antiinflammatory, and proapoptotic anticancer activities of Kakadu plum and Illawarra plum polyphenolic fractions. Nutr Cancer, 63(7):1074-84. doi: 10.1080/01635581.2011.596646.

The invention claimed is:
1. A method for treating a skin condition of fine lines in skin of a subject, the method comprising topically administering a composition comprising:
  from about 0.05 wt % to about 50 wt % of an extract produced from molasses to the subject, the extract being produced by contacting molasses with an amount of ethanol to form a precipitate, removing the precipitate to form a supernatant, and removing the ethanol from the supernatant, such that the extract comprises from about 10 catechin equivalent (CE) g/L to about 50 CE g/L of polyphenols or from about 100 CE mg/g to about 500 CE mg/g of polyphenols, and from about 1 catechin equivalent (CE) g/L to about 15 CE g/L of flavonoids or from about 10 CE mg/g to about 150 CE mg/g of flavonoids, 1-3 µg/g sinapic acid, 1-4 µg/g vanillin, 3-8 µg/g swertisin and has a brix value of 70-75; and
  a cosmetically acceptable carrier.
2. The method of claim 1, wherein the composition comprises from about 0.05 wt % to about 10 wt % of the extract.

3. The method of claim 2, wherein the composition comprises from about 0.05 wt % to about 5 wt % of the extract.

4. The method of claim 1, wherein the skin condition being treated further includes wrinkles.

5. The method of claim 1, wherein the treatment provides fine line reduction, wrinkle reduction, or wrinkle depth reduction.

6. The method of claim 1, wherein the composition is administered twice daily.

7. The method of claim 1, wherein the composition is administered once daily.

8. The method of claim 1, wherein the skin is on the face, neck, hands, back, or combinations thereof.

9. The method of claim 8, wherein the skin is on the face.

10. The method of claim 1, wherein the composition is in the form of a cream, serum, or gel.

11. The method of claim 1, wherein the extract comprises from about 15 CE g/L to about 40 CE g/L of polyphenols or about 150 CE mg/g to about 400 CE mg/g of polyphenols.

12. The method of claim 11, wherein the extract comprises from about 20 CE g/L to about 30 CE g/L of polyphenols or from about 200 CE mg/g to about 300 CE mg/g of polyphenols.

13. The method of claim 1, wherein the composition further comprises lactic acid, glycolic acid, or both.

* * * * *